United States Patent
Klee et al.

(10) Patent No.: US 10,512,594 B2
(45) Date of Patent: Dec. 24, 2019

(54) DENTAL COMPOSITION

(71) Applicant: DENTSPLY SIRONA Inc., York, PA (US)

(72) Inventors: Joachim E. Klee, Radolfzell (DE); Florian Szillat, Constance (DE); Maximilian Maier, Constance (DE); Helmut Ritter, Wuppertal (DE); Jacques Lalevee, Mulhouse (FR); Jean Pierre Fouassier, Hippolyte (FR); Fabrice Morlet-Savary, Pfastatt (FR); Celine Dietlin, Mulhouse (FR); Mariem Bouzrati-Zerelli, Mulhouse (FR); Christoph P Fik, Schonenberg a.d. Thur (CH)

(73) Assignee: DENTSPLY SIRONA Inc., York, PA (US)

( * ) Notice: Subject to any disclaimer, the term of this patent is extended or adjusted under 35 U.S.C. 154(b) by 12 days.

(21) Appl. No.: 15/766,397

(22) PCT Filed: Oct. 10, 2016

(86) PCT No.: PCT/EP2016/074223
§ 371 (c)(1),
(2) Date: Apr. 6, 2018

(87) PCT Pub. No.: WO2017/060527
PCT Pub. Date: Apr. 13, 2017

(65) Prior Publication Data
US 2018/0289592 A1    Oct. 11, 2018

(30) Foreign Application Priority Data

Oct. 8, 2015 (EP) .................................. 15188969
May 19, 2016 (EP) .................................. 16170375

(51) Int. Cl.
*C08F 2/46* (2006.01)
*C08F 2/50* (2006.01)
*C08G 61/04* (2006.01)
*A61K 6/083* (2006.01)
*A61K 6/00* (2006.01)

(52) U.S. Cl.
CPC ............ *A61K 6/083* (2013.01); *A61K 6/0017* (2013.01); *A61K 6/0052* (2013.01)

(58) Field of Classification Search
CPC .... A61K 6/083; A61K 6/0052; A61K 6/0017; A61K 6/0023; C08L 33/08; C08L 33/10; C08L 33/26

USPC ............ 522/28, 7, 6, 189, 184, 1, 71; 520/1
See application file for complete search history.

(56) References Cited

U.S. PATENT DOCUMENTS

| | | | |
|---|---|---|---|
| 2007/0129458 A1 | 6/2007 | Walz | |
| 2008/0277814 A1 | 11/2008 | Moszner | |
| 2009/0239967 A1 | 9/2009 | Moszner | |
| 2015/0080490 A1 | 3/2015 | Burtscher | |
| 2018/0303722 A1* | 10/2018 | Klee | A61K 6/0073 |
| 2019/0117522 A1* | 4/2019 | Klee | A61K 6/0038 |
| 2019/0117523 A1* | 4/2019 | Fik | C09D 4/00 |

FOREIGN PATENT DOCUMENTS

| | | | |
|---|---|---|---|
| EP | 0076102 A1 | 4/1983 | |
| EP | 1234543 A1 | 8/2002 | |
| EP | 1905415 A1 | 4/2008 | |
| EP | 2103297 A1 | 9/2009 | |
| EP | 2604247 A1 | 6/2013 | |
| EP | 3153150 A1 | 4/2017 | |
| EP | 2895138 B1 | 11/2017 | |
| EP | 3246001 A1 | 11/2017 | |
| WO | 2007079070 A1 | 7/2007 | |
| WO | 2008015646 A2 | 2/2008 | |
| WO | 2009058843 A2 | 5/2009 | |
| WO | 2013153166 A1 | 10/2013 | |
| WO | 2014040729 A1 | 3/2014 | |
| WO | WO-2014040729 A1 * | 3/2014 | A61K 6/0044 |
| WO | 2015144579 A1 | 10/2015 | |
| WO | 2017060527 A1 | 4/2017 | |

OTHER PUBLICATIONS

Sekiguchi et al, Dye-Sensitized Photooxidation of Silyl Diazo Compounds. Intramolecular Oxygen Transfer of Carbonyl Oxides, 1982, J. Org. Chem., 47, 2900-2903 (Year: 1982).*

* cited by examiner

Primary Examiner — Jessica Whiteley
(74) Attorney, Agent, or Firm — DENTSPLY SIRONA Inc.

(57) ABSTRACT

The present invention relates to a dental composition comprising an initiator system comprising a sensitizer compound having an acylsilyl- or acylgermyl-group and a specific coinitiator compound. The present invention also relates to an initiator system consisting essentially of the sensitizer compound having an acylsilyl- or acylgermyl-group and a coinitiator compound wherein a C—H bond dissociation energy is less than 95 Kcal/mol. Furthermore, the present invention relates to the use of this initiator system for the preparation of a dental composition.

14 Claims, 9 Drawing Sheets

DENTAL COMPOSITION

FIELD OF THE INVENTION

The present invention relates to a dental composition comprising an initiator system comprising a sensitizer compound having an acylsilyl- or acylgermyl-group and a specific coinitiator compound. The present invention also relates to an initiator system consisting essentially of the sensitizer compound having an acylsilyl- or acylgermyl-group and a coinitiator compound wherein a C—H bond dissociation energy is less than 95 Kcal/mol. Furthermore, the present invention relates to the use of this initiator system for the preparation of a dental composition.

BACKGROUND OF THE INVENTION

The restoration of teeth commonly involves a light curable dental composition containing free-radically polymerizable resins. Light curing of a dental composition involves a photoinitiator system generating free radicals upon exposure to visible light. Free radicals may be typically produced by either of two pathways:
(1) the photoinitiator compound undergoes excitation by energy absorption with subsequent decomposition of the compound into one or more radicals (Norrish type I), or
(2) the photoinitiator compound undergoes excitation and the excited photoinitiator compound interacts with a second compound by either energy transfer or a redox reaction to form free radicals from any of the compounds (Norrish type II).

In order for a photoinitiator to be useful for use in a dental composition, the quantum yields indicating the conversion of light radiation to radical formation needs to be high since absorption or shielding of light by further components of the dental composition limit the amount of energy available for absorption by the photoinitiators. Accordingly, only about 70 percent conversion of the polymerizable groups may be expected in a polymerization of a typical dental composition initiated for example by a camphor quinone (CQ)/amine photoinitiator system, whereby the mechanical strength of the polymerized dental composition is less than optimal and unreacted monomers may leach out of the polymerized dental composition. The leaching monomers may have detrimental effects. In order to alleviate this problem, multifunctional monomers are frequently used which are more likely to be included in the polymer network.

In addition, photoinitiators are required to have a high acid resistance, solubility (e. g. for adhesives), thermal stability, and storage stability when incorporated into a dental composition.

Finally, given that dental compositions usually contain (meth)acrylate or (meth)acrylamide monomers, free radical photocuring may be inhibited by the presence of oxygen. Oxygen inhibition is due to the rapid reaction of propagating radicals with oxygen molecules to yield peroxyl radicals which are not as reactive towards carbon-carbon unsaturated double bonds and therefore do not initiate or participate in any photopolymerization reaction. Oxygen inhibition may lead to premature chain termination and, therefore, incomplete photocuring. Nevertheless, a certain degree of oxygen inhibition on the top surface of the adhesive layer is required for the bonding to the adjacent restorative.

Accordingly, the polymerization initiator system has a critical influence on the quality of the dental material. Conventionally, camphor quinone in combination with a tertiary amine and optionally with a diphenyliodonium (DPI) salt or 2,4,6-trimethylbenzoylphenyl phosphinate (Irgacure® TPO) are frequently used as photoinitiator system. However, the presence of amines in acrylate-containing compositions can cause yellowing in the resulting photo-cured composition, and soften the cured composition. Moreover, the use of aromatic amines might give rise to toxicological concerns.

Furthermore, it is desirable that the light activating the photoinitiator system has a long wavelength in order to avoid damage of soft tissue during polymerization of the dental composition in the patient's mouth. Accordingly, the photoinitiator system is required to contain a chromophoric group efficiently absorbing light of the desired wavelength in a range of from 400 to 800 nm. Accordingly, it is important to find a photoinitiator system with a sufficiently high absorption coefficient. However, the absorbtion coefficient must not be excessively high, because an excessively high absorption coefficient of the photoinitiator system increases the coloration of the photoinitiator system and thereby the coloration of the dental composition before light curing. In any case, it is necessary that the chromophoric groups are efficiently destroyed during polymerization so that the coloration of the initiator system disappears in the polymerized dental composition, the so-called "photo-bleaching". A destruction of the chromophoric groups during polymerization may also be useful in increasing the depth of cure of the dental composition since activating light is not shielded from unpolymerized layers of the dental composition by the photoinitiator system present in polymerized layers covering the unpolymerized layers.

EP 0 076 102 A1 discloses a photopolymerizable composition comprising an epoxy compound, a curing catalyst including at least one aluminium compound having at least one organic radical directly bonded to the aluminum atom, at least one α-ketosilyl compound and at least one photosensitizer selected from the group consisting of benzophenone compounds and thioxanthone compounds. The photopolymerizable composition may be used in the field of electrical equipment, e.g. for producing an insulating material, or as a photoresist material.

EP 1 905 415 A1 discloses dental compositions comprising a polymerizable binder and a photoinitiator containing an acylgermanium compound.

EP 2 103 297 A1 discloses compositions, among others dental compositions, which comprise at least a polymerizable binder and a polymerization initiator comprising at least an acylgermanium compound. The acylgermanium compound comprises 2 to 100 acylgermanium moieties, which are linked via a bond or a branched or linear aliphatic, aromatic or aliphatic-aromatic hydrocarbon residue having a valency corresponding to the number of acylgermanium moieties. As a reference example, a dental composition is disclosed comprising a polymerization initiator system consisting of benzoyltrimethylgermane, and the polymerizable compounds UDMA and triethyleneglycoldimethacrylate.

US 2015/0080490 A1 discloses a polymerizable dental composition comprising a photoinitiator mixture which contains at least one diacylgermanium compound such as bis-(4-methoxybenzoyl)diethylgermanium, at least one α-diketon such as camphor quinone, and an accelerator.

WO 2015/144579 A1 discloses a polymerizable dental composition comprising a photoinitiator mixture that contains an α-diketone photoinitiator compound having a light absorption maximum in the range from 300 to 500 nm such as camphor quinone, and a coinitiator in the form of a hydride of silicium or germanium.

El-Roz M. et al., Current Trends in Polymer Science, 2011, vol. 15, pages 1 to 13 discloses free radical photopolymerisation of an epoxy acrylate monomer in the presence of a photoinitiator system consisting of isopropylthioxanthone as photoinitiator in combination with acylsilane compounds, among others methyl(trimethylsilyl)methanone and methyl(triphenylsilyl)methanone. This document does not disclose dental compositions. In the above described conventional dental compositions comprising silicium or germanium containing organic compounds as photoinitiator, typically, a coinitiator is contained. For example, EP 1 905 415 A1 and US 2015/0080490 A1 disclose ethyl N,N-dimethylaminobenzoate (EDB) as coinitiator.

SUMMARY OF THE INVENTION

It is the problem of the present invention to provide an improved dental composition comprising an initiator system comprising a sensitizer compound having an acylsilyl- or acylgermyl-group, which composition provides
improved polymerization efficiency including a high conversion and good curing rate which may be adapted to provide a suitable working time of the composition,
improved depth of cure, and
absence of discoloration problems.

Moreover, it is the problem of the present invention to provide a specific initiator system and a use of the initiator system for the preparation of a dental composition.

The present invention provides a dental composition comprising
(a) an initiator system comprising:
(a1) a sensitizer compound of the following formula (I):

wherein
X is a group of the following formula (II):

wherein
M is Si or Ge;
$R^1$ represents a substituted or unsubstituted hydrocarbyl or hydrocarbylcarbonyl group;
$R^2$ represents a substituted or unsubstituted hydrocarbyl or hydrocarbylcarbonyl group;
$R^3$ represents a substituted or unsubstituted hydrocarbyl group; and
R (i) has the same meaning as X, whereby the sensitizer compound of formula (I) may be symmetrical or unsymmetrical; or
(ii) is a group of the following formula (III):

wherein
Y represents a single bond, an oxygen atom or a group NR', wherein R' represents a substituted or unsubstituted hydrocarbyl group;
$R^4$ represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group; or
(iii) when M is Si, R may be a substituted or unsubstituted hydrocarbyl group, and
(a2) a coinitiator compound of the following formula (IV):

$$X'\text{-}L\text{-}X'' \quad (IV)$$

wherein
X' represents a group of the following formula (V) or (VI):

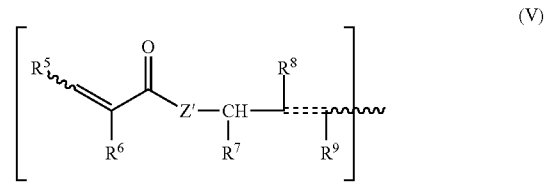

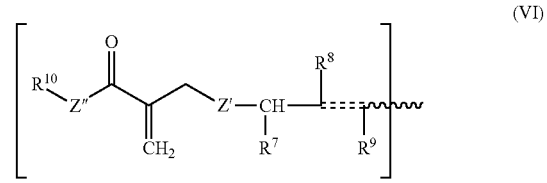

wherein
the dotted lines represent
a double bond or a triple bond, whereby in case a triple bond is present, $R^8$ and $R^9$ are absent;
the jagged line(s) indicate(s) that formula (V) and (VI) include any (E) or (Z) isomer,
Z' and Z" which may be the same or different, independently represent an oxygen atom, a sulfur atom or >N—R°, wherein
R° is a hydrogen atom, a straight-chain, branched or cyclic alkyl or alkenyl group which group may be substituted by an alkoxy or acidic group, or a group of the following formula (VII):

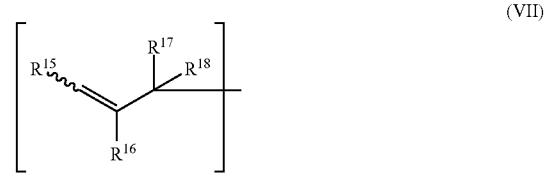

wherein
the jagged line indicates that formula (VII) includes any (E) or (Z) isomer,
$R^{15}$ and $R^{16}$,
which may be the same or different, independently represent a hydrogen atom or a straight-chain, branched or cyclic alkyl or alkenyl group, which group may be substituted by an alkoxy group or acidic group;

$R^{17}$ and $R^{18}$,
which may be the same or different, independently represent a hydrogen atom or a straight-chain, branched or cyclic alkyl or alkenyl group, which group may be substituted by an alkoxy or acidic group, or $R^{17}$ and $R^{18}$ represent together an oxygen atom forming a carbonyl group together with the adjacent carbon atom;

$R^5$ and $R^6$,
which may be the same or different, independently represent a hydrogen atom or a straight-chain, branched or cyclic alkyl or alkenyl group, which group may be substituted by at least one moiety selected from the group consisting of a hydroxyl group, an alkoxy group and an acidic group;

$R^7$ represents a hydrogen atom or a straight-chain, branched or cyclic alkyl or alkenyl group, which group may be substituted by an alkoxy or acidic group;

$R^8$ and $R^9$
which may be the same or different, independently represent a hydrogen atom, a straight-chain, branched or cyclic alkyl or alkenyl group, which group may be substituted by an alkoxy or acidic group;

$R^{10}$ represents a hydrogen atom or a straight-chain, branched or cyclic alkyl or alkenyl group, which group may be substituted by an alkoxy group;

X" represents a moiety selected from the group consisting of a hydroxyl group, a thiol group, an alkoxy group and an acidic group, or a moiety of the following formula (VIII) or (IX):

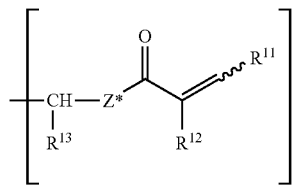

(VIII)

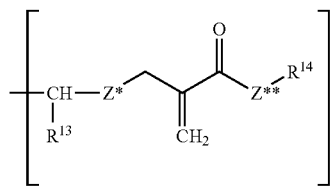

(IX)

wherein
the jagged line indicates that formula (VIII) includes any (E) or (Z) isomer, Z* and Z**, which may be the same or different, independently represent an oxygen atom, a sulfur atom or >N—R˙, wherein
R˙ is a hydrogen atom, a straight-chain, branched or cyclic alkyl or alkenyl group which group may be substituted by an alkoxy or acidic group, or R˙ independently is a group of the formula (VII) as defined for R°;

$R^{11}$ and $R^{12}$
which may be the same or different, independently represent a hydrogen atom, a straight-chain, branched or cyclic alkyl or alkenyl group, which group may be substituted by at least one moiety selected from the group consisting of a hydroxyl group, a thiol group, an alkoxy group and an acidic group;

$R^{13}$ represents a hydrogen atom or a straight-chain, branched or cyclic alkyl or alkenyl group, which group may be substituted by an alkoxy or acidic group;

$R^{14}$ represents a hydrogen atom or a straight-chain, branched or cyclic alkyl or alkenyl group, which group may be substituted by an alkoxy group;

or alternatively,
any two residues of $R^5$, $R^6$, $R^7$, $R^8$, $R^9$, $R^{10}$, R°, $R^{11}$, $R^{12}$, $R^{13}$, $R^{14}$, R˙, and if present, $R^{15}$, $R^{16}$, $R^{17}$ and $R^{18}$ may represent together an alkylene or alkenylene group, which may be substituted by an alkoxy group, an acidic group or a —NR▲R▼ group wherein R▲ and R▼ independently from each other represent a hydrogen atom or an alkyl group; or any two residues of $R^5$, $R^6$, $R^7$, $R^8$, $R^9$, $R^{10}$, R°, $R^{11}$, $R^{12}$, $R^{13}$, $R^{14}$, R˙, and if present, $R^{15}$, $R^{16}$, $R^{17}$ and $R^{18}$, which are not geminal or vicinal groups, may represent together a single bond,
wherein said single bond or said optionally substituted alkylene or alkenylene group form together with the bridging atoms to which the residues are linked a 3- to 8-membered saturated or unsaturated ring, wherein the coinitiator compound of formula (IV) may comprise one or more of said 3- to 8-membered saturated or unsaturated ring(s); and L, which may be present or absent, represents, when present, a divalent linker group, and when absent X' and X" are bonded directly by a single bond.

Furthermore, the present invention provides an initiator system consisting essentially of
(a1) a sensitizer compound of the formula (I) as described above, and
(a2) a coinitiator wherein a C—H bond dissociation energy is less than 95 Kcal/mol.

Finally, the present invention provides a use of the aforementioned initiator system for the preparation of a dental composition.

The present invention is based on the recognition that a dental composition according to the present invention comprising an initiator system comprising (a1) the sensitizer compound of formula (I) and (a2) the coinitiator compound of formula (IV) provides improved polymerization efficiency and high curing speed, and does not give rise to discoloration problems of a dental composition. Accordingly, a relatively large amount of the dental composition can be photocured with reduced exposure to radiation. Due to the high efficiency of the initiator system (a), the presence of oxygen, or oxygen inhibition, is not a serious detriment during photocuring of a dental composition according to the present invention.

BRIEF DESCRIPTION OF THE FIGURES

FIG. 5 shows the IR-spectra of BAABE with 2% w/w CQ, and FIG. 6 shows the IR-spectra of BAABE with 2% w/w DKSi, wherein the two different allylic C—H are indicated in the structural formula of BAABE by encirclement. In FIGS. 5 and 6, spectrum (1) was recorded before polymerization, and spectrum (2) was recorded after polymerization.

FIG. 7: sample thickness 20 µm;
and
  FIG. 8: sample thickness 250 µm.

FIG. 10 shows the IR-spectra of the polymerization with DKSi, and FIG. 11 shows the IR-spectra of the polymerization with CQ, wherein spectrum (1) was recorded before polymerization, and spectrum (2) was recorded after polymerization.

DETAILED DESCRIPTION OF PREFERRED EMBODIMENTS

Figure 1:
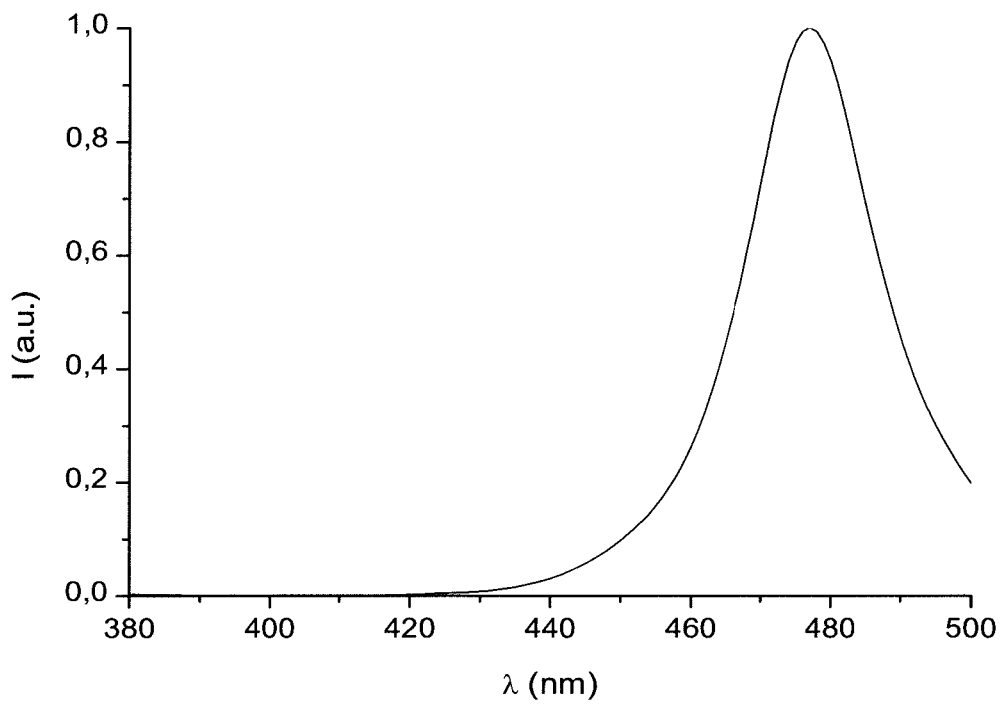
FIG. 1 shows the emission spectra of the irradiation source used for the irradiation of the photocurable samples, namely a blue dental LED centred at 477 nm (SmartLite® Focus from Dentsply, about 1000 mW/cm²).

The term "polymerization" relates to the combining by covalent bonding of a large number of smaller molecules, such as monomers, to form larger molecules, that is, macromolecules or polymers. The monomers may be combined to form only linear macromolecules or they may be combined to form three-dimensional macromolecules, commonly referred to as crosslinked polymers. For example, monofunctional monomers form linear polymers, whereas monomers having at least two functional groups form crosslinked polymers also known as networks. In case of a higher conversion rate of the polymerizable monomer, the amount of multifunctional monomers may be reduced or the leaching problem may be alleviated.

The terms "curing" and "photocuring" mean the polymerization of functional oligomers and monomers, or even polymers, into a crosslinked polymer network. Curing is the polymerization of unsaturated monomers or oligomers in the presence of crosslinking agents.

The terms "photocurable" and "curable" refer to a dental composition that will polymerize into a crosslinked polymer network when irradiated for example with actinic radiation such as ultraviolet (UV), visible, or infrared radiation.

The term "quantum yield" is used herein to indicate the efficiency of a photochemical process. More particularly, quantum yield is a measure of the probability of the excitation of a particular molecule after absorption of a light quantum. The term expresses the number of photochemical events per photon absorbed.

"Actinic radiation" is any electromagnetic radiation that is capable of producing photochemical action and can have a wavelength of at least 150 nm and up to and including 1250 nm, and typically at least 300 nm and up to and including 750 nm.

The term "polymerizable double bound" as used herein in connection with compound(s) (a4) and compound(s) (b) means any double bond capable of radical polymerization, preferably a carbon-carbon double bond. Examples of the polymerizable double bond include vinyl, conjugated vinyl, allyl, acryl, methacryl and styryl. More preferably, the polymerizable double bound is selected from the group consisting of acryl, methacryl and styryl. Acryl and methacryl may be (meth)acryloyl or (meth)acrylamide. Most preferably, for the compound(s) (b), the polymerizable double bound is acryl or methacryl, and for the compound (a4), the polymerizable double bond with which groups $R^5$, $R^6$ Ar and L may be substituted is styryl.

The term "initiator system" refers to a system comprising at least (a1) a sensitizer compound of formula (I) and (a2) a coinitiator compound of formula (IV). Optionally, the initiator system may further comprise at least one compound selected from the group consisting of (a3) an iodonium salt, a sulfonium salt and a phosphonium salt, (a4) an aromatic tertiary phosphine compound, and (a5) an additional coinitiator.

The term "coinitiator" refers to a molecule that produces a chemical change in another molecule such as a photoinitiator in a photochemical process, or to a photoinitiator other than compound of formula (I). The coinitiator may be a compound of formula (IV) or the (a5) an additional coinitiator in the form of an electron donor or an additional sensitizer other than the sensitizer compound of formula (I).

The term "sensitizer" as used herein means any chemical compound that forms free radicals when activated, e. g. by exposure to light or interaction with a coinitiator in a photochemical process. For example, the compound of formula (I) represents a sensitizer.

The term "electron donor" as used herein means a compound which is capable of donating electrons in a photochemical process. Suitable examples include organic compounds having heteroatoms with electron lone pairs.

The ordinate axis label "O.D." in FIGS. 5, 6, 10 and 11 means optical density, which is an arbitrary unit.

The present invention relates to a dental composition. The dental composition may be a dental restorative or dental prosthetic composition. More preferably, the dental composition is selected from the group consisting of a dental adhesive composition, a dental composite composition, a resin modified dental cement, a pit and fissure sealer, a desensitizer and a varnish. The dental composition may be cured by irradiation of actinic radiation.

(a) The Initiator System

The dental composition comprises (a) an initiator system comprising (a1) a sensitizer compound of formula (I). The dental composition may comprise one or more sensitizer compound(s) of formula (I).

The sensitizer compound (a1) has the following formula (I):

X—R          (I).

In formula (I), X is an acylsilyl or acylgermyl group of the following formula (II):

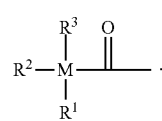

(II)

In formula (II), M is Si or Ge, $R^1$ and $R^2$ independently from each other represent a substituted or unsubstituted hydrocarbyl or hydrocarbylcarbonyl group, and $R^3$ represents a substituted or unsubstituted hydrocarbyl group.

R of formula (I) may (i) have the same meaning as X, whereby the sensitizer compound of formula (I) may be symmetrical or unsymmetrical, (ii) be a group of formula (III), or (iii) when M is Si, R may be a substituted or unsubstituted hydrocarbyl group.

The group of formula (III) has the following structural formula:

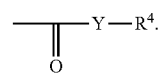

(III)

In the group of formula (III), Y represents a single bond, an oxygen atom or a group NR', wherein R' represents a substituted or unsubstituted hydrocarbyl group. $R^4$ represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group.

It was surprisingly found that sensitizer compounds of formula (I) represent sensitizers which are particularly suitable for dental compositions. With sensitizer compounds of formula (I), a high polymerization efficiency is attained, and no discoloration problems occur, or in a polymerization system comprising a conventional photoinitiator such as camphor quinone, coloration is efficiently suppressed. Furthermore, sensitizer compounds of formula (I) have a light absorption within the wavelength range typically applied in dental application, they are compatible with the ingredients of dental compositions and besides, they are considered toxicologically acceptable.

In connection with sensitizer compound of formula (I), the term "substituted" as used herein means that $R^1$, $R^2$, $R^3$, $R^4$ and R' may be substituted by a substituent selected from the group consisting of halogen atoms, a nitro group, a cyano group, a hydroxy group, an amino group, $C_{1-6}$ alkyl groups, $C_{1-6}$ alkoxy groups and a —$NR^xR^y$ group wherein $R^x$ and $R^y$ independently from each other represent a $C_{1-6}$ alkyl group. Here, illustrative of the halogen atoms can be fluorine, chlorine, bromine and iodine. The $C_{1-6}$ alkyl groups are, for example, methyl, ethyl, n-propyl, isopropyl and n-butyl. Illustrative of the $C_{1-6}$ alkoxy groups are, for example, methoxy, ethoxy and propoxy. The alkyl moieties in these substituents may be linear, branched or cyclic. Preferably, the substituent is selected from a chlorine atom, a nitro group, a $C_{1-4}$ alkoxy group and a —$NR^xR^y$ group wherein $R^x$ and $R^y$ independently from each other represent a $C_{1-4}$ alkyl group.

If $R^1$, $R^2$ and $R^3$ are substituted, then it is preferred that they are substituted with 1 to 3 substituents, more preferably with 1 substituent.

In the sensitizer compound of formula (I), moieties $R^1$, $R^2$ and $R^3$ may be defined as follows:

$R^1$ and $R^2$ independently from each other represent a substituted or unsubstituted hydrocarbyl or hydrocarbylcarbonyl group, and $R^3$ represents a substituted or unsubstituted hydrocarbyl group.

The hydrocarbyl group may be an alkyl group, a cycloalkyl group, a cycloalkylalkyl group, an arylalkyl group or an aryl group.

An alkyl group may be straight-chain or branched $C_{1-20}$ alkyl group, typically a $C_{1-8}$ alkyl group. Examples for a $C_{1-6}$ alkyl group can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl.

A cycloalkyl group may be a $C_{3-20}$ cycloalkyl group, typically a $C_{3-8}$ cycloalkyl group.

Examples of the cycloalkyl group can include those having 3 to 6 carbon atoms, for example, cyclopropyl, cyclobutyl, cyclopentyl and cyclohexyl.

A cycloalkylalkyl group may have 4 to 20 carbon atoms and may include a combination of a linear or branched alkyl group having 1 to 6 carbon atoms and a cycloalkyl group having 3 to 14 carbon atoms. Examples of the cycloalkylalkyl(-) group can for example, include methylcyclopropyl(-) methylcyclobutyl(-), methylcyclopentyl(-), methylcyclohexyl(-), ethylcyclopropyl(-), ethylcyclobutyl(-), ethylcyclopentyl(-), ethylcyclohexyl(-), propylcyclopropyl(-), propylcyclobutyl(-), propylcyclopentyl(-), propylcyclohexyl(-).

An arylalkyl(-) group may be a $C_{7-20}$ arylalkyl(-) group, typically a combination of a linear or branched alkyl group having 1 to 6 carbon atoms and an aryl(-) group having 6 to 10 carbon atoms. Specific examples of an arylalkyl(-) group are a benzyl(-) group or a phenylethyl(-) group.

An aryl group can include aryl groups having 6 to 10 carbon atoms. Examples of the aryl group are phenyl and naphtyl.

The hydrocarbylcarbonyl groups of $R^1$ and $R^2$ represent acyl groups ($R_{org}$—(C=O)—) in which the organic residue $R_{org}$ is a hydrocarbyl residue as defined above.

Sensitizer compound of formula (I) may contain one or two hydrocarbylcarbonyl groups, that is either one of $R^1$ or $R^2$ is a hydrocarbylcarbonyl group, or both $R^1$ and $R^2$ are hydrocarbylcarbonyl groups. Preferably, sensitizer compound of formula (I) contains one hydrocarbylcarbonyl group.

Preferably, the hydrocarbylcarbonyl group is an arylcarbonyl group, more preferably a benzoyl group.

Preferably, $R^1$ and $R^2$ are independently selected from the group consisting of a straight chain or branched $C_{1-6}$ alkyl group, and a phenyl or benzoyl group which may optionally be substituted by one to three substitutents selected from halogen atoms, a nitro group, a $C_{1-4}$ alkoxy group and a —$NR^xR^y$ group wherein $R^x$ and $R^y$ independently from each other represent a $C_{1-4}$ alkyl group, and $R^3$ is a straight chain or branched $C_{1-6}$ alkyl group or a phenyl group.

Most preferably, $R^1$ and $R^2$ are independently selected from the group consisting of a straight chain or branched $C_{1-4}$ alkyl group, and a phenyl or benzoyl group which may optionally be substituted with one substituent selected from the group consisting of selected from a halogen atom, a nitro group, a $C_{1-4}$ alkoxy group and a —$NR^xR^y$ group wherein $R^x$ and $R^y$ independently from each other represent a $C_{1-4}$ alkyl group, and $R^3$ is a straight chain or branched $C_{1-4}$ alkyl group.

In the sensitizer compound of formula (I), R may have the same meaning as X, whereby the sensitizer compound of formula (I) may be symmetrical or unsymmetrical. Alternatively, R may represent a substituted or unsubstituted hydrocarbyl group, or a group of formula (III). Preferably, if R has the same meaning as X, then sensitizer compound of formula (I) is unsymmetrical. If R represents a substituted or unsubstituted hydrocarbyl group, then the hydrocarbyl group has the same meaning as defined above for $R^1$ and is independently selected therefrom.

In the group of formula (III) of sensitizer compound of formula (I), $R^4$ represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group.

If $R^4$ of formula (III) is a trihydrocarbylsilyl group, a mono(hydrocarbylcarbonyl)-dihydrocarbylsilyl group or a di(hydrocarbylcarbonyl)monohydrocarbylsilyl group, each of the hydrocarbyl and hydrocarbylcarbonyl groups has the same meaning as defined for $R^1$, $R^2$ and $R^3$ and is independently selected therefrom.

In formula (III), R' has the same meaning as defined for $R^3$ and is independently selected therefrom.

If M is Si in sensitizer compound of formula (I), R may be also be a substituted or unsubstituted hydrocarbyl group, wherein the hydrocarbyl group has the same meaning as defined above for $R^3$ and is independently selected therefrom.

For example, sensitizer compounds of formula (I) wherein R has the same meaning as X and which are symmetrical may be have the following structural formulae:

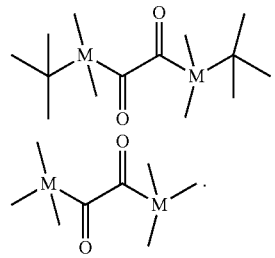

For example, sensitizer compounds of formula (I) wherein R represents a group of formula (III) wherein Y is a bond, an oxygen atom or a NR' group, and $R^4$ represents a substituted or unsubstituted hydrocarbyl group may have the following structural formulae:

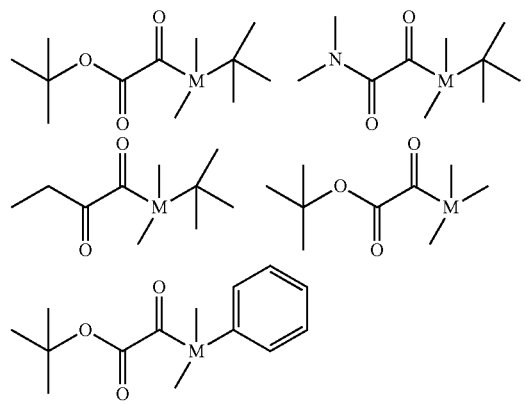

-continued

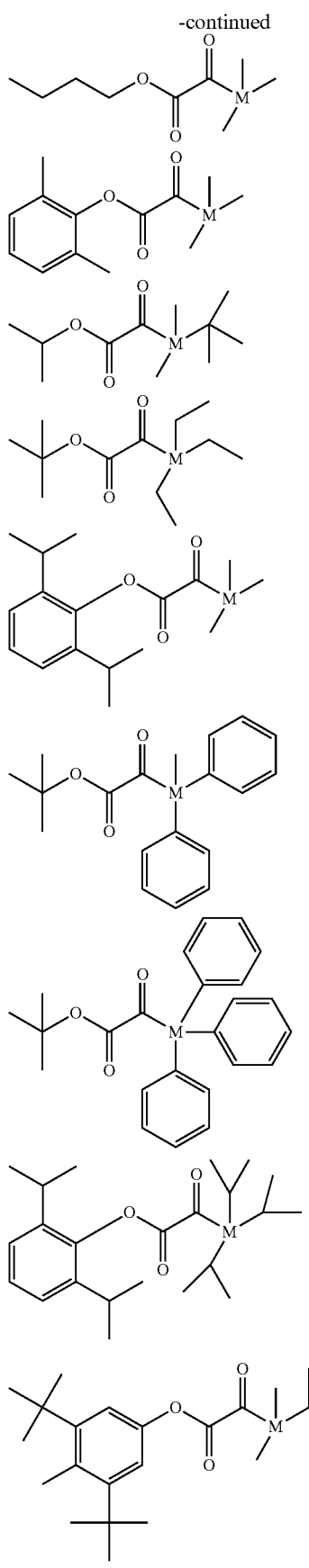

For example, sensitizer compounds of formula (I) wherein R represents a group of formula (III) wherein $R^4$ represents a trihydrocarbylsilyl group have the following structural formulae:

For example, (a1) the sensitizer compounds of formula (I) wherein M is Si and R represents a substituted or unsubstituted hydrocarbyl group, may have the following structural formulae:

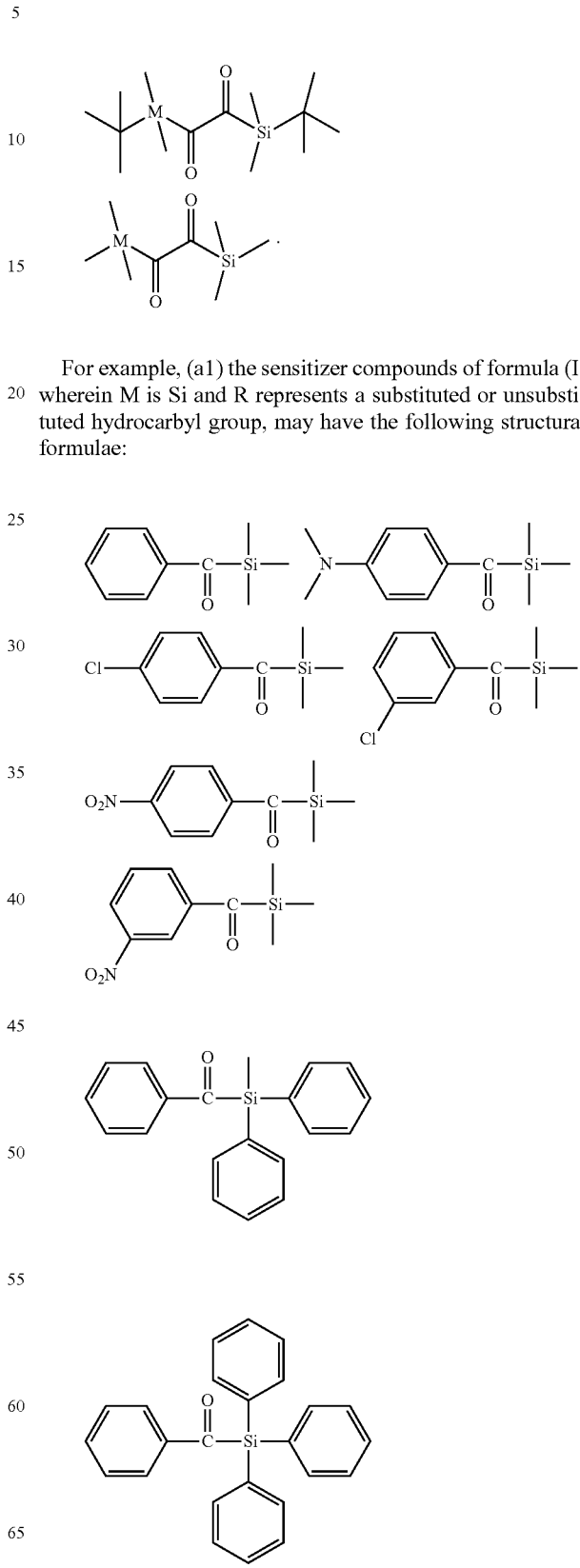

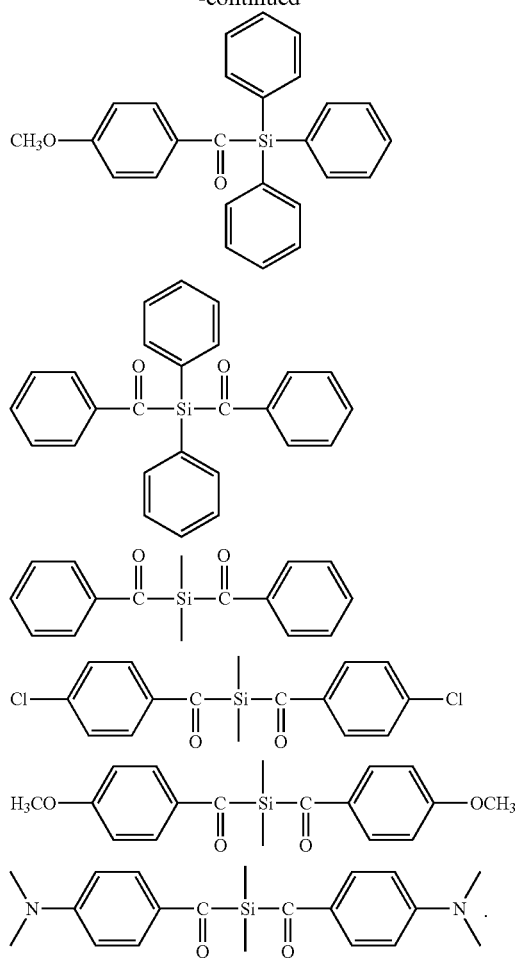

Preferably, (a1) the sensitizer compound of formula (I) is selected from the group consisting of:

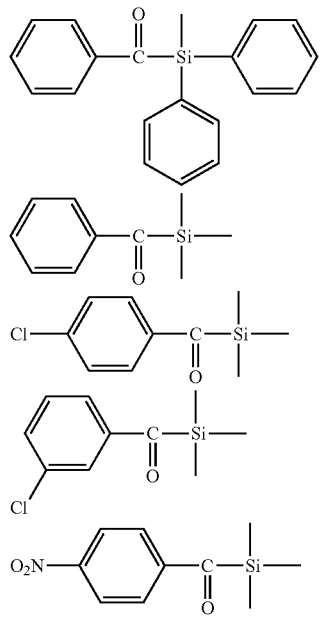

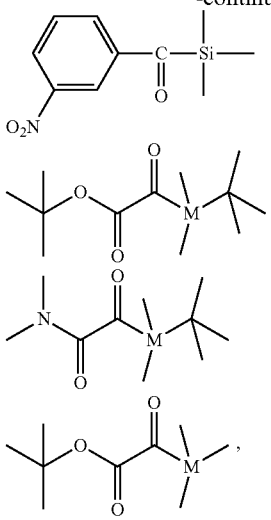

wherein sensitizer compounds of formula (I) with M=Si are particularly preferred.

More preferably, (a1) the sensitizer compound of formula (I) is selected from the group consisting of:

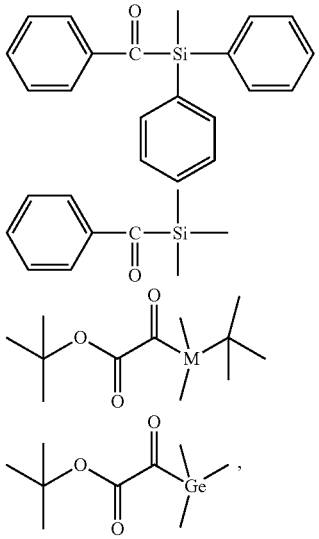

wherein it is particularly preferred that M=Si.

Most preferably, (a1) the sensitizer compound of formula (I) is tert-butyl (tert-butyldimethylsilyl)glyoxylate (DKSi). DKSi has the following structural formula:

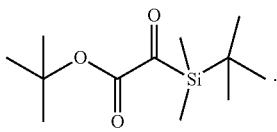 [SMILES: CC(C)(C)OC(=O)C(=O)[Si](C)(C)C(C)(C)C]

In case the dental composition is an acidic composition having a pH of less than 7, depending on the composition's pH level, it is preferred to select sensitizer compounds of formula (I) with the proviso that they do not contain ester groups, or at least only ester groups which do not significantly hydrolyze in aqueous media at pH 3 at room temperature within one month. Thereby, an advantageous stability of an acidic dental composition, that is a composition having a pH of less than 7, in terms of shelf-life stability of the uncured dental composition as well as stability after curing in the mouth of a patient is ensured. Therefore, for acidic dental compositions, particularly preferred are sensitizer compounds of formula (I) excluding R being a group of formula (III) in which Y is an oxygen atom.

Furthermore, since the acylsilyl moiety (—C(=O)—Si—) might be sensitive to basic conditions, that is a pH higher than 7, it is preferred to suitably select a pH value of the composition being higher than 7 with the proviso that the acylsilyl moiety is not cleaved in aqueous media at the selected basic pH at room temperature within one month.

The compound of the formula (I) may be a known compound which is commercially available or a may be prepared according to published procedures.

The sensitizer compound of formula (I) wherein M is Si and R represents a substituted or unsubstituted hydrocarbyl group may for example be readily prepared by means of a one-step Pd-catalyzed reaction with a disilane as described e.g. by Yamamoto K. et al., *J. Tetrahedron Lett.*, 1980, vol. 21, pages 1653 to 1656:

Scheme 1: Preparation of acylsilanes

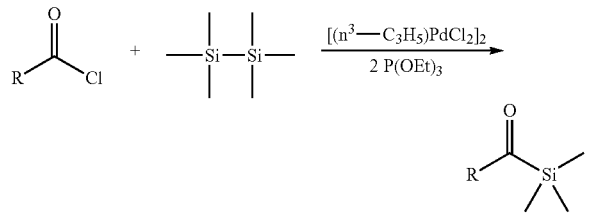

In Scheme 1, the reaction is exemplary depicted with hexamethylsilan as the disilane, whereby a sensitizer compound of formula (I) wherein $R^1$, $R^2$ and $R^3$ represent a methyl group is obtained. It is understood that $R^1$, $R^2$ and $R^3$ can be varied by applying disilanes having hydrocarbon substituents other than methyl.

The sensitizer compound of formula (I) wherein M of X is Si, R represents a group of formula (III) in which Y is an oxygen atom and $R^4$ represents a hydrocarbyl group may for example be prepared by a three-step synthesis as described by Nicewicz D. A. et al. in *Org. Synth.*, 2008, 85, pages 278 to 286. In this three-step synthesis, an acetoacetate is converted to an azide compound, which is then reacted with a trihydrocarbylsilyltrifluoromethane-sulfonate to obtain a trihydrocarbylsilyldiazoacetate, which is finally reacted with potassium peroxymonosulfate to arrive at the target compound:

Scheme 2: Preparation of silylglyoxylates

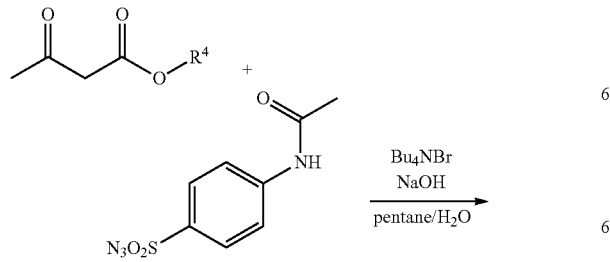

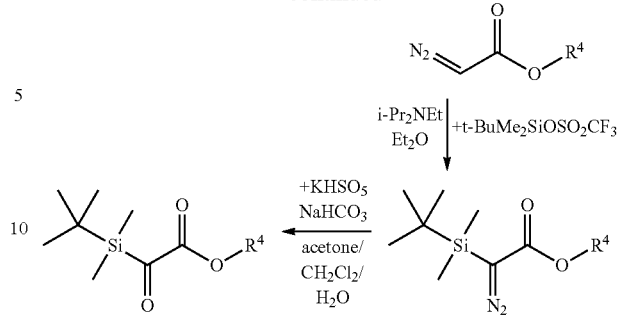

In Scheme 2, the reaction is exemplary depicted for obtaining a sensitizer compound of formula (I) wherein in X of formula (II), $R^1$ and $R^2$ represent a methyl group, and $R^3$ represents a tert-butyl group. It is understood that $R^1$, $R^2$ and $R^3$ can be varied by applying a trihydrocarbylsilyltrifluoromethane-sulfonate other than t-BuMeSiOSO$_2$CF$_3$.

Alternatively, sensitizer compounds of formula (I) wherein M of X is Si, R represents a group of formula (III) and Y represents an oxygen atom may be prepared by a single-pot three-component coupling reaction of a silylglyoxylate, a terminal alkyne and an aldehyde in the presence of ZnI$_2$ and Et$_3$N as described by Nicewicz D. A. in *J. Am. Chem. Soc.*, 2005, 127 (17), pages 6170 to 6171. Further syntheses of silylglyoxylate compounds are described e.g. by Boyce G. R. et al. in *J. Org. Chem.*, 2012, 77 (10), pages 4503 to 4515 and Boyce G. R. et al. in *Org. Lett.*, 2012, 14 (2), pages 652 to 655.

The sensitizer compound of formula (I) wherein M of X is Ge and R represents a group of formula (II) in which Y is an oxygen atom and $R^4$ represents a hydrocarbyl group may for example be prepared by a two step synthesis starting from a trihydrocarbylgermyltrifluoromethane-sulfonate such as trimethylgermane triflate. Such trimethylgermane triflate may be prepared starting from commercially available chlorotrimethylgermane as described by S. P. Mallela et al. in J. Fluorine Chem., 1989, vol. 44, issue 2, pages 309 to 328. As shown in Scheme 3 below, the trihydrocarbylgermyltrifluoromethane-sulfonate and an azide compound are reacted to obtain a trihydrocarbylgermyldiazoacetate, which is reacted with oxone (potassium peroxymonosulfate) to arrive at the target compound:

Scheme 3: Preparation of germylglyoxylates

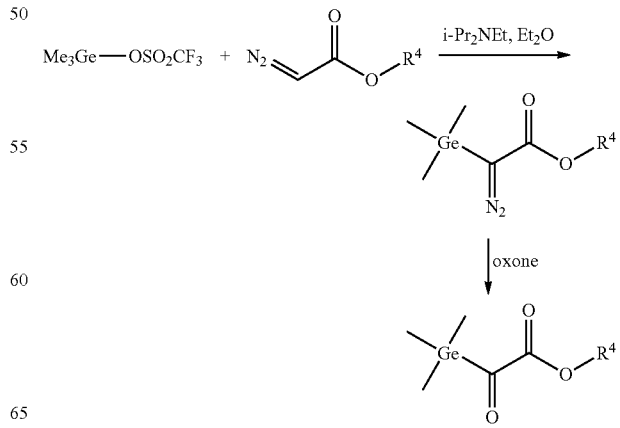

In Scheme 3, the reaction is exemplary depicted for obtaining a sensitizer compound of formula (I) wherein in X of formula (II), $R^1$, $R^2$ and $R^3$ represent a methyl group. It is understood that $R^1$, $R^2$ and $R^3$ can be varied by applying a trihydrocarbylgermyltrifluoromethane-sulfonate other than $Me_3Ge$—$OSO_2CF_3$.

For example, the following sensitizer compounds of formula (I) are known and commercially available, and their Chemical Abstracts (CAS) No. is given in brackets: benzoyltriphenylsilane (1171-49-9), benzoyltrimethylsilan (5908-41-8), 1-[(trimethylsilyl) carbonyl]-naphthalene (88313-80-8), 1-methoxy-2-[(trimethylsilyl)-carbonyl]-benzene (107325-71-3), (4-chlorobenzoyl) (triphenyl) silane (1172-90-3), (4-nitrobenzoyl) (triphenyl) silane (1176-24-5), (methyldiphenylsilyl)phenyl-methanone (18666-54-1), (4-methoxybenzoyl) triphenylsilan (1174-56-7) and tert-butyl (tert-butyldimethylsilyl)glyoxylate (852447-17-7).

All sensitizer compounds of formula (I) comprise the group of formula (II)

$$R^2-\underset{\underset{R^1}{|}}{\overset{\overset{R^3}{|}}{M}}-\overset{O}{\overset{\|}{C}}-, \qquad (II)$$

wherein M, $R_1$, $R_2$ and $R_3$ are defined as above. Depending on the selection of M, the group of formula (II) represents an acylsilane or acylgermane group. Upon exposure to UV-VIS-light, the bond between M and the acyl group may be cleaved, whereby a silyl/germyl and an acyl radical is formed as a polymerization initiating structure, but in competition to the cleavage into to radicals, a carbene structure might be formed:

Scheme 4: carbene formation versus radical formation

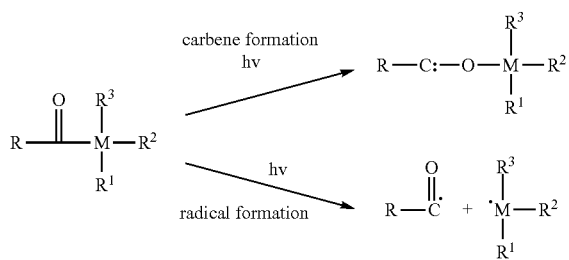

This competition between the formation of polymerization initiating radicals and carbene formation is described for acylsilanes by El-Roz, M. et al. in Current Trends in Polymer Science, 2011, vol. 15, pages 1 to 13.

Besides, in case in sensitizer compound of formula (I) wherein R has the same meaning as X or is a group of formula (III), the C—C bond of the 1,2-diketone moiety (—C(=O)—C(=O)—) may be cleaved upon exposure to UV-VIS-light into two acyl radicals. This cleavage is exemplary shown for sensitizer compound of formula (I) wherein R is a group of formula (III) and Y is an oxygen atom, that is for a glyoxylate (—O—C(=O)—C(=O)—) compound:

Scheme 5: cleavage of -O-C(=O)-C(=O)- moiety of a glyoxylate

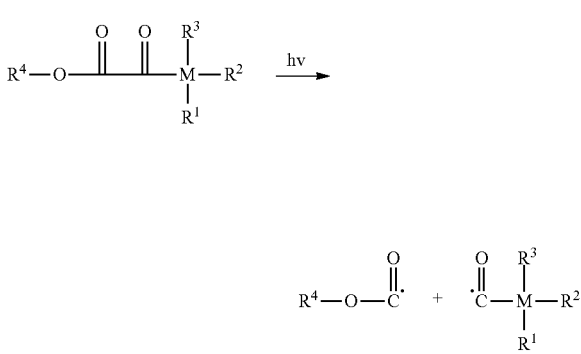

Besides, in sensitizer compound of formula (I), there is a third possibility for a radical cleavage in case R is a compound of formula (III) wherein Y is an oxygen atom and $R^4$ is a substituted or unsubstituted hydrocarbyl group. Namely, an intra- or intermolecular hydrogen abstraction might occur, where a hydrogen radical is abstracted:

Scheme 6: hydrogen abstraction (intra- or intermolecular)

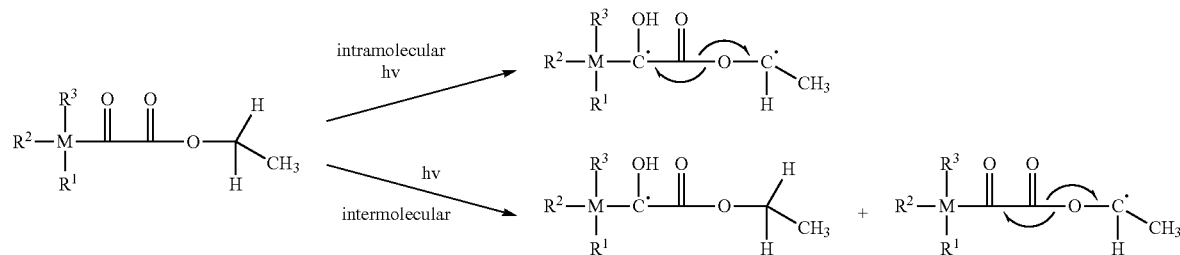

Both the cleavage of a glyoxylate group and the hydrogen abstraction mechanism is known for photoinitiators which do not contain silicium or germanium, such as ethyl phenylglyoxylate (Irgacure® MBF).

For sensitizer compounds of formula (I) wherein R has the same meaning as X or is a group of formula (III), the present inventors carried out molecular modelling calculations from which it appears that a Si—C or Ge—C bond cleavage can be ruled out, since the C—C bond of the —C(=O)—C(=O)— moiety is weaker than the Si—C or Ge—C bond.

The sensitizer compounds of formula (I) represent photoinitiators. Specifically, they may act as Norrish type I photoinitiators. However, in the presence of a coinitiator such as the compounds of formula (IV), the sensitizer compounds of formula (I) may partially act as Norrish type II photoinitiators.

The dental composition further comprises (a2) a coinitiator compound. The dental composition may comprise one or more coinitiator(s) compound(s).

The coinitiator compound has the following formula (IV):

X'-L-X"  (IV).

In formula (IV), X' is a specific polymerizable group which is linked by L representing a divalent linker group or a single bond, to a group X". The group X" may be polymerizable.

According to the present invention, X' is a group of the following formula (V) or (VI):

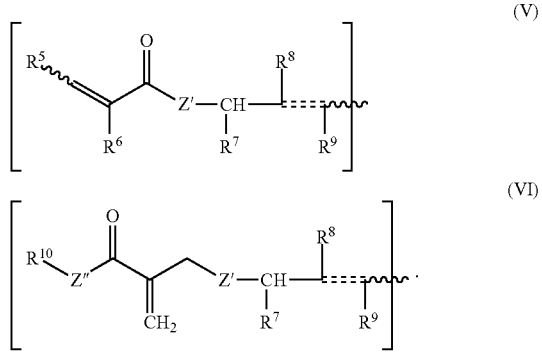

In formula (V) an (VI), the dotted lines represent a double bond or a triple bond, preferably a double bond. In case a triple bond is present, $R^8$ and $R^9$ are absent.

The jagged line(s) indicate(s) that formula (V) and (VI) include any (E) or (Z) isomer. In case the dotted lines in formula (VI) represent a triple bond, then there is no (E) or (Z) isomerism at the moiety $CR^8=CR^9$.

Specifically, in formula (V) and (VI), $R^5$ may be in (E) or (Z) configuration, for example relative to the carbonyl group. Further, if the bond between $CR^8$ and $CR^9$ is a double bond, then the jagged line/line may be in (E) or (Z) configuration, for example relative to the moiety —$CHR^7$—. Preferably, $R^5$ is in (E) configuration relative to the substituent at the adjacent carbon atom of the carbon-carbon double bond having the highest priority according to the Cahn-Ingold-Prelog priority rules, which is either $R^6$ or the carbonyl group. Further, if the bond between $CR^8$ and $CR^9$ is a double bond, then it is preferred that the substituent bonded to the carbon-carbon double bond by the jagged line/bond has a higher priority than substituent $R^8$, and the jagged line/bond is in (E) configuration relative to the substituent at the adjacent carbon atom of the carbon-carbon double bond having the highest priority according to the Cahn-Ingold-Prelog priority rules, which is either $R^8$ or the moiety —$CHR^7$—.

Accordingly, any coinitiator compound of formula (IV) is characterized by a (meth)acryl group of formula (V) and/or (VIII) or inverse (meth)acryl group of formula (VI) and/or (IX), and a double or triple bond imparting C—H acidity to the hydrogen atom of the adjacent moiety —$CHR^7$—. Without wishing to be bound to theory, it is believed that this C—H acidity, in combination with the polymerizable C=C double bond of the (inverse) (meth)acryl group provides for the particularly advantageous polymerization enthalpy and viscosity of compound of formula (IV). In addition, owing to the above described C—H acidity, the coinitiator compound of formula (IV) provides an advantageous maximum rate of polymerization and desirable mechanical characteristic such as flexural strength.

C—H acidity may be impaired by internal and external N-allyl groups. It was surprisingly found that the C—H acidity of the hydrogen atom of the moiety —$CHR^7$— is less prone to impairment by internal and external N-allyl groups e.g. when the double or triple bond represented together by $CR^8$ and $CR^9$ is located between $Z'=N—R°$ and $Z*=N—R^*$. Therefore, in order to provide an advantageous CH-acidity, in present formula (IV), the aforementioned double or triple bond is located between $Z'$ and $Z^*$ which may form an N-allyl group when representing N—$R°$ and $Z^*=N—R^*$.

It was surprisingly found that with the C—H acidic hydrogen atom of the moiety —$CHR^7$— in formulae (V) and (VI), a C—H bond is provided having an advantageous C—H bond dissociation energy (BDE). Besides of the aforementioned C—H bond, the allylic hydrogen of formula (VII) may optionally additionally provide a C—H bond having and advantageous BDE.

Preferably, the coinitiator compound of formula (IV) has a C—H bond having a C—H bond dissociation energy (BDE) of less than 95 Kcal/mol, more preferably less than 90 Kcal/mol, even more preferably less than 84 Kcal/mol, yet even more preferably less than 82 Kcal/mol, most preferably less than 80 Kcal/mol. In the present invention, BDE was determined by molecular modelling with the reference software Gaussian 09.

Since the compounds of formula (IV) have a C—H bond with an advantageously low BDE, they can readily donate protons and/or electrons, e.g. in a photochemical process. For this reason, compounds of formula (IV) represent highly efficient coinitiators for an initiator system.

From prior art EP 2 895 138 A1 it is known that N-substituted acrylic acid amide compounds having a linker group in the form of a divalent $C_1$ to $C_{20}$ alkylene group optionally containing a carbon-carbon double bond, may be used as a polymerizable compound for dental compositions. As a specific example of such polymerizable compound, this document discloses N,N'-diallyl-1,4-bisacrylamido-(2E)-but-2-en (BAABE). However, in EP 2 895 138 A1, there is no general teaching for the position of the C—C double bond in the linker of the polymerizable compound described therein, since the above explained effect of the C—H acidity and C—H bond having an advantageous low BDE was not recognized. Instead, EP 2 895 138 A1 teaches that an ally group has to be mandatory bonded to the nitrogen of a polymerizable (meth)acrylamide unit for rendering possible an advantageous cyclopolymerization reaction.

Hence, in view of EP 2 895 138 A1, it was surprisingly found that compounds of formula (IV), such as BAABE, do not only represent advantageous polymerizable compounds for dental compositions. Rather, compounds of formula (IV) also represent highly efficient coinitiator compounds, in particular for an initiator system comprising a Si or Ge sensitizer compound of formula (I).

$R^5$ and $R^6$ of formula (V) and (VI) may be the same or different, and independently represent a hydrogen atom or a straight-chain, branched or cyclic alkyl or alkenyl group, which group may be substituted by at least one moiety selected from the group consisting of a hydroxyl group, an alkoxy group and an acidic group.

$R^7$ of formula (V) and (VI) represents a hydrogen atom or a straight-chain, branched or cyclic alkyl or alkenyl group, which group may be substituted by an alkoxy or acidic group.

$R^8$ and $R^9$ of formula (V) and (VI) may be the same or different, and independently represent a hydrogen atom, a straight-chain, branched or cyclic alkyl or alkenyl group, which group may be substituted by an alkoxy or acidic group.

$R^{10}$ of formula (V) and (VI) represents a hydrogen atom or a straight-chain, branched or cyclic alkyl or alkenyl group, which group may be substituted by an alkoxy group.

Z' and Z", which may be the same or different, independently represent an oxygen atom, a sulfur atom or >N—R°, wherein R° is a hydrogen atom, a straight-chain, branched or cyclic alkyl or alkenyl group which group may be substituted by an alkoxy or acidic group.

Alternatively, R° is a group of the following formula (VII):

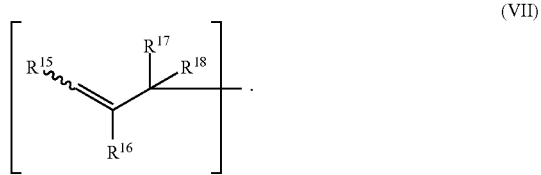

(VII)

Preferably, Z' and/or Z" represent >N—R° wherein R° represents a group of formula (VII), most preferably a group of formula (VII) wherein $R^{15}$, $R^{16}$, $R^{17}$ and $R^{18}$ represent hydrogen atoms, that is group (VII) is an unsubstituted allyl group. Because, said group of formula (VII) or allyl group may take part together with the polymerizable carbon-carbon double bond of the (meth)acryl group of formula (V) or the inverse (meth)acryl group of formula (VI) in a cyclopolymerization reaction according to the following Scheme 7:

Scheme 7: Intramolecular cyclopolymerization of coinitiator compound of formula (IV) wherein X' = group of formula (V) in which Z' = >N-R° with R° = group of formula (VII) wherein $R^{15} = R^{16} = R^{17} = R^{18}$ = hydrogen atom.

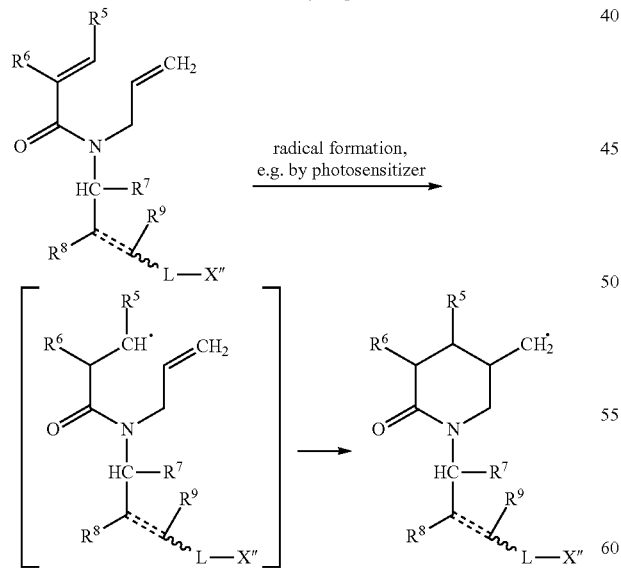

The formation of rings by means of the above cyclopolymerization can be verified for example by means of infrared spectroscopy (IR) alone or in combination with a further analytical method, for example nuclear magnetic resonance spectroscopy (NMR).

The intramolecular cyclopolymerization of N-allylacrylamides is known in the field of chemistry and described e.g. by L. Trossarelli et al., "Free Radical Polymerization of Unconjugated Dienes: III. N-Allylacrylamide in Methanol", *Die Makromolekulare Chemie,* 1967, vol. 100, pages 147 to 155, or by W. Fukuda, "Cyclopolymerization of N-Alkyl-N-allylacrylamides", *Polymer Journal,* 1988, vol. 20, no. 4, pages 337 to 344.

Without wishing to be bound to theory, the above described cyclopolymerization may result in the formation of a reduced number of polymeric network points, that is a reduced crosslinking density, compared to coinitiator compounds of formula (IV) having no group R° in the form of an alkylene group such as the group of formula (VII). This in turn may provide for a reduced polymerisation stress as compared with comparable coinitiator compounds of formula (IV) having identical molar mass and identical amount (s) of polymerizable double bond(s), but no group Z' and/or Z" being >N—R° wherein R represents a group of formula (VII), specifically an allyl group.

The jagged line indicates that formula (VII) includes any (E) or (Z) isomer. Specifically, $R^{15}$ may be in (Z) or (E) configuration, for example relative to the moiety $CR^{17}R^{18}$. Preferably, $R^{15}$ is in (E) configuration relative to the substituent at the adjacent carbon atom of the carbon-carbon double bond having the highest priority according to the Cahn-Ingold-Prelog priority rules, which may either be $R^{16}$ or the moiety $CR^{17}R^{18}$.

$R^{15}$ and $R^{16}$ of formula (VII) may be the same or different and independently represent a hydrogen atom or a straight-chain, branched or cyclic alkyl or alkenyl group, which group may be substituted by an alkoxy group or acidic group.

$R^{17}$ and $R^{18}$ of formula (VII), which may be the same or different, independently represent a hydrogen atom or a straight-chain, branched or cyclic alkyl or alkenyl group, which group may be substituted by an alkoxy or acidic group. Alternatively, $R^{17}$ and $R^{18}$ of formula (VII) represent together an oxygen atom forming a carbonyl group together with the adjacent carbon atom.

In formula (IV), X" represent a moiety selected from the group consisting of a hydroxyl group, a thiol group, an alkoxy group and an acidic group, or a moiety of the following formula (VIII) or (IX):

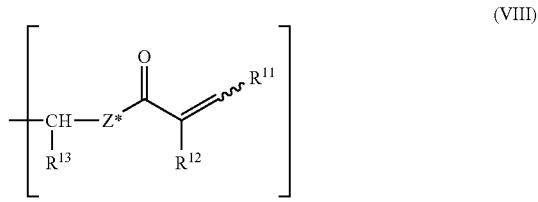

(VIII)

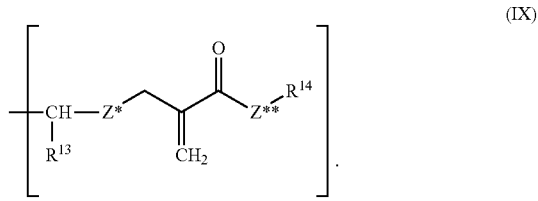

(IX)

The jagged line indicates that formula (VIII) includes any (E) or (Z) isomer. Specifically, in formula (VIII), $R^{11}$ may be in (Z) or (E) configuration relative to the substituent at the adjacent carbon atom of the carbon-carbon double bond having the highest priority according to the Cahn-Ingold-Prelog priority rules, which may either be $R^{12}$ or the carbonyl group.

$R^{11}$ and $R^{12}$ of formula (VIII) and (IX) may be the same or different, and independently represent a hydrogen atom, a straight-chain, branched or cyclic alkyl or alkenyl group, which group may be substituted by at least one moiety selected from the group consisting of a hydroxyl group, a thiol group, an alkoxy group and an acidic group.

$R^{13}$ of formula (VIII) and (IX) represents a hydrogen atom or a straight-chain, branched or cyclic alkyl or alkenyl group, which group may be substituted by an alkoxy or acidic group.

$R^{14}$ of formula (VIII) and (IX) represents a hydrogen atom or a straight-chain, branched or cyclic alkyl or alkenyl group, which group may be substituted by an alkoxy group.

Z* and Z** of formula (VIII) and (IX), which may be the same or different, independently represent an oxygen atom, a sulfur atom or >N—R˙, wherein R˙ is a hydrogen atom, a straight-chain, branched or cyclic alkyl or alkenyl group which group may be substituted by an alkoxy or acidic group. Alternatively, R˙ is a group of the formula (VII) as defined for R° of Z' and Z" of formula (V) and (VI), and is independently selected from R° of Z' and Z" of formula (V) and (VI). Preferably, formula (VII) of R˙ of formula (VIII) and (IX) is identical with formula (VII) of R° of formula (V) and (VI).

Preferably, Z* and/or Z** represent >N—R˙ wherein R˙ represents a group of formula (VII), most preferably a group of formula (VII) wherein $R^{15}$, $R^{16}$, $R^{17}$ and $R^{18}$ represent hydrogen atoms, that is group (VII) is an unsubstituted allyl group. Because, said group of formula (VII) or allyl group may take part together with the polymerizable carbon-carbon double bond of the methacryl group of formula (VII) or the inverse methacryl group of formula (VIII) in a cyclopolymerization reaction as described above in connection with Z' and Z".

The groups ">N—R°" and ">N—R˙" defined for Z'/Z" and Z*/Z** denote a tertiary amine group wherein a residue R° or R˙ is bonded to the nitrogen atom which is incorporated in formula (V), (VI), (VIII) and (IX) via two bonds/valencies indicated by ">". Alternatively, instead of ">N—R°" and ">N—R˙", the denotations "—N(—R°)—" and "—N(—R˙)—" may be used.

The "straight-chain, branched or cyclic alkyl or alkenyl group" for $R^5$, $R^6$, $R^7$, $R^8$, $R^9$, $R^{10}$, $R°$, $R^{15}$, $R^{16}$, $R^{17}$, $R^{18}$ of formula (V) and (VI), and $R^{11}$, $R^{12}$, $R^{13}$, $R^{14}$, $R^{15}$, $R^{16}$, $R^{17}$, $R^{18}$, R˙ of formula (VIII) and (IX) is not particularly limited. Preferably, this "straight-chain, branched or cyclic alkyl or alkenyl group" represents a straight chain $C_{1-16}$ or branched or cyclic $C_{3-8}$ alkyl group or a straight chain $C_{2-16}$ or branched or cyclic $C_{3-8}$ alkenyl group, more preferably a straight chain $C_{1-8}$ or branched or cyclic $C_{3-6}$ alkyl group or a straight chain $C_{2-8}$ or branched or cyclic $C_{3-6}$ alkenyl group, most preferably a straight chain $C_{1-4}$ or branched or cyclic $C_{4-6}$ alkyl group or a straight chain $C_{2-4}$ or branched or cyclic $C_{4-6}$ alkenyl group.

Illustrative examples for straight chain or branched alkyl groups are methyl, ethyl, n-propyl, i-propyl, n-butyl, isobutyl, tert-butyl, sec-butyl, pentyl or hexyl, and for the straight chain or branched alkenyl group ethenyl, n-propenyl, i-propenyl, n-butenyl, isobutenyl, tert-butenyl sec-butenyl, pentenyl or hexenyl.

The term "alkenyl" as used herein in connection with $R^5$, $R^6$, $R^7$, $R^8$, $R^9$, $R^{10}$, $R°$, $R^{15}$, $R^{16}$, $R^{17}$, $R^{18}$ of formula (V) and (VI) and $R^{11}$, $R^{12}$, $R^{13}$, $R^{14}$, $R^{15}$, $R^{16}$, $R^{17}$, $R^{18}$, R˙ of formula (VIII) and (IX) means a monovalent group derived from a hydrocarbon having the above defined carbon number. This alkenyl group preferably contains at least one carbon-carbon double bond, more preferably 1 to 3 carbon-carbon double bonds, even more preferably 1 or 2 carbon-carbon double bonds, most preferably one carbon-carbon bond. Furthermore, it is preferred that at least one carbon-carbon double bond of the alkenyl group is located between second and third carbon atoms adjacent to a first carbon which attaches the alkenyl group to compound of formula (IV).

The most preferred alkenyl groups for $R^5$, $R^6$, $R^7$, $R^8$, $R^9$, $R^{10}$, $R°$, $R^{15}$, $R^{16}$, $R^{17}$, $R^{18}$ of formula (V) and (VI) and $R^{11}$, $R^{12}$, $R^{13}$, $R^{14}$, $R^{15}$, $R^{16}$, $R^{17}$, $R^{18}$, R˙ of formula (VIII) and (IX), which may be the same or different, are independently selected from the group consisting of allyl, 1 cyclopropane-1-yl, 2-cyclopropane-1-yl, 1-cyclobutane-1-yl, 2-cyclobutane-1-yl, 1-cyclopentane-1-yl, 2-cyclopentane-1-yl, 3-cyclopentane-1-yl, 1,3-cyclopentadiene-1-yl, 2,4-cyclopentadiene-1-yl, 1-cycloxene-1-yl, 2-cycloxene-1-yl, 3-cycloxene-1-yl, 1,3-cycloheadiene-1-yl and 2,5-cyclohexadiene-1-yl.

The "alkoxy group" defined for $R^5$, $R^6$, $R^7$, $R^8$, $R^9$, $R^{10}$, $R°$, $R^{15}$, $R^{16}$, $R^{17}$, $R^{18}$ of formula (V) and (VI) and $R^{11}$, $R^{12}$, $R^{13}$, $R^{14}$, $R^{15}$, $R^{16}$, $R^{17}$, $R^{18}$, R˙ of formula (VII) and (IX) is not particularly limited. Preferably, said alkoxy group is a straight chain $C_{1-16}$ or branched or cyclic $C_{3-8}$ alkoxy group, more preferably a straight chain $C_{1-8}$ or branched or cyclic $C_{3-6}$ alkoxy group, most preferably a straight chain $C_{1-4}$ or branched or cyclic $C_{4-6}$ alkoxy group. Illustrative examples for $C_{1-6}$ alkoxy groups are methoxy, ethoxy, propoxy, isopropyloxy, cyclopropyloxy, cyclobutyloxy, cyclopentyloxy and cyclohexyloxy.

The term "acidic group" as used herein in connection with $R^5$, $R^6$, $R^7$, $R^8$, $R^9$, $R^{10}$, $R°$, $R^{15}$, $R^{16}$, $R^{17}$, $R^{18}$ of formula (V) and (VI) and $R^{11}$, $R^{12}$, $R^{13}$, $R^{14}$, $R^{15}$, $R^{16}$, $R^{17}$, $R^{18}$, R˙ of formula (VIII) and (IX) means any group imparting acidity in terms of proton donation capability to the compound of formula (IV). Preferably, this acidic group is independently selected from a carboxylic acid group, a sulfonic acid group, a phosphonic acid group and a phosphoric acid monoester group (—O—P(=O)(OH)$_2$).

The following are preferred groups of formula (V) and (VI), wherein R° and $R^7$ are defined as above:

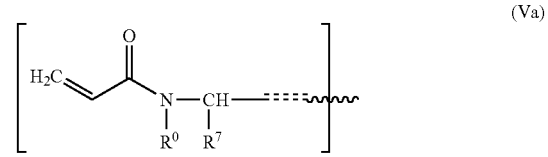

(Va)

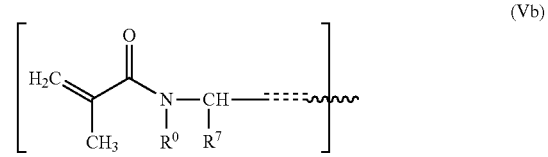

(Vb)

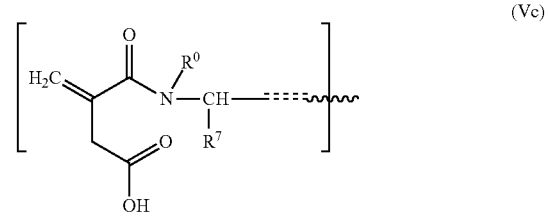

(Vc)

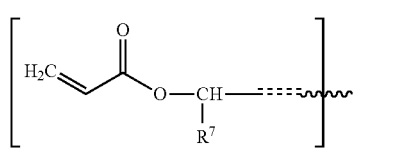
(Vd)

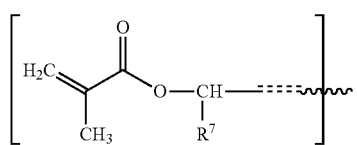
(Ve)

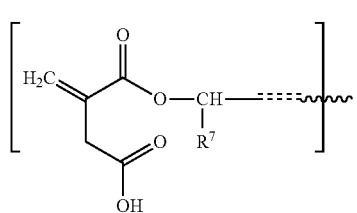
(Vf)

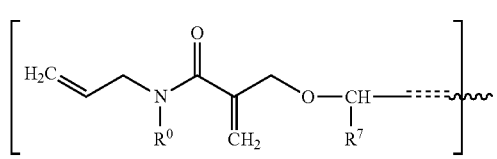
(VIa)

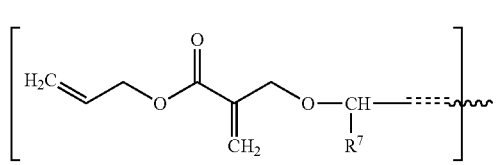
(VIb)

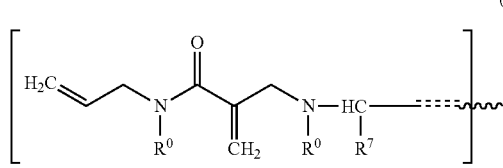
(VIc)

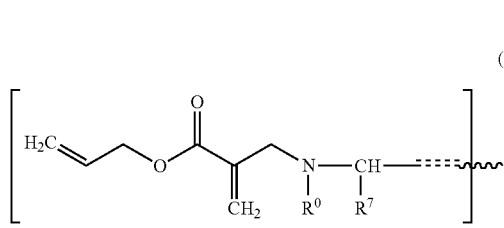
(VId)

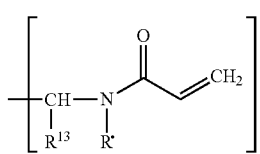
(VIIIa)

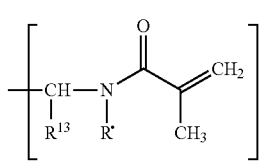
(VIIIb)

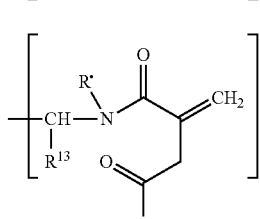
(VIIIc)

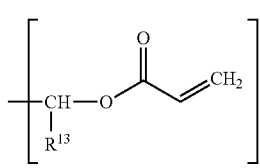
(VIIId)

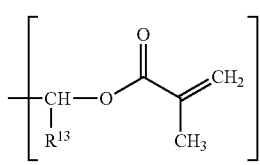
(VIIIe)

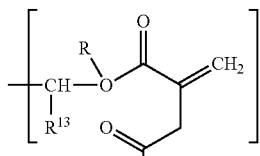
(VIIIf)

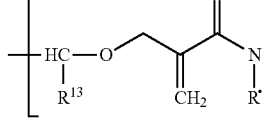
(IXa)

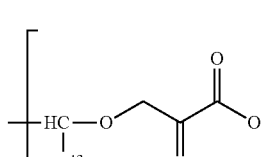
(IXb)

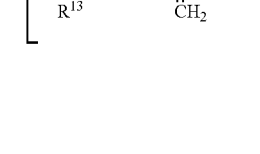
(IXc)

In formula (Va), (Vb), (Vc), (Vd), (Ve), (Vf), (VIa), (VIb), (VIc), (VId), $R^7$ preferably represents a hydrogen atom, and $R°$ preferably represents a hydrogen atom, methyl, ethyl or n-propyl which may optionally be substituted with an acidic group, allyl, 2-cyclopropane-1-yl, 2-cyclobutane-1-yl, 2-cyclopentane-1-yl, 2,4-cyclopentadiene-1-yl, 2-cycloxene-1-yl and 2,5-cyclohexadiene-1-yl.

The groups of formula (Va) and (Via) are particularly preferred.

The following are preferred groups of formula (VIII) and (IX), wherein $R˙$ and $R^{13}$ are defined as above:

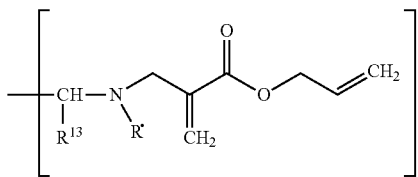

(IXd)

In formula (VIIIa), (VIIIb), (VIIIc), (VIIId), (VIIIe), (VIIIf), (IXa), (IXb), (IXc) and (IXd), $R^{13}$ preferably represents a hydrogen atom, and R˙ preferably represents a hydrogen atom, methyl, ethyl or n-propyl which may optionally be substituted with an acidic group, allyl, 1-cyclopropene-3-yl, 1-cyclobutene-3-yl, 1-cyclopentene-3-yl, 1,3-cyclopentadiene-5-yl, 1-cycloxene-3-yl and 1,4-cyclohexadiene-6-yl.

The groups of formula (VIIIa) and (IXa) are particularly preferred.

Preferably, if X' of the coinitiator compound of formula (IV) represents a group of formula (V), then X" represents a group of formula (VIII), and if X' represents a group of formula (VI), then X" represents a group of formula (IX).

It is preferred that $R^{17}$ and $R^{18}$ in R° of formula (V) and (VI) and/or R' of formula (VIII) and (IX) represent together an oxygen atom forming a carbonyl group together with the adjacent carbon atom.

In formula (IV), alternatively to the above definitions for residues $R^5$, $R^6$, $R^7$, $R^8$, $R^9$, $R^{10}$, R°, $R^{11}$, $R^{12}$, $R^{13}$, $R^{14}$, R˙, $R^{15}$, $R^{16}$, $R^{17}$ and $R^{18}$, any two of these residues may form a ring together with the bridging atoms to which the residues are linked. Specifically, any two residues of $R^5$, $R^6$, $R^7$, $R^8$, $R^9$, $R^{10}$, R°, $R^{11}$, $R^{12}$, $R^{13}$, $R^{14}$, R˙, and if present, $R^{15}$, $R^{16}$, $R^{17}$ and $R^{18}$ may represent together an alkylene or alkenylene group which may be substituted by an alkoxy group, and acidic group or a —NR▲ R▼ group wherein R▲ and R▼ independently from each other represent a hydrogen atom or an alkyl group.

Alternatively, any two residues of $R^5$, $R^6$, $R^7$, $R^8$, $R^9$, $R^{10}$, R°, $R^{11}$, $R^{12}$, $R^{13}$, $R^{14}$, R˙, and if present, $R^{15}$, $R^{16}$, $R^{17}$ and $R^{18}$, which are not geminal or vicinal groups, may represent together a single bond.

The above described single bond or the above described optionally substituted alkylene or alkenylene group may form together with the bridging atoms to which the residues are linked a 3- to 8-membered saturated or unsaturated ring, wherein the coinitiator compound of formula (IV) may comprise one or more of said 3- to 8-membered saturated or unsaturated ring(s).

In connection with the above described ring formation of any two of residues $R^5$, $R^6$, $R^7$, $R^8$, $R^9$, $R^{10}$, R°, $R^{11}$, $R^{12}$, $R^{13}$, $R^{14}$, R˙, $R^{15}$, $R^{16}$, $R^{17}$ and $R^{18}$, the "alkoxy group" with which the alkylene or alkenylene group formed by two of these residues may be substituted is preferably a $C_{1-6}$ alkoxy group, more preferably a $C_{1-3}$ alkoxy group such as methoxy, ethoxy, n- or iso-propoxy, and the "alkyl group" of the "—NR▲ R▼ group" is preferably a $C_{1-6}$ alkyl group, more preferably a $C_{1-3}$ alkyl group, such as methyl, ethyl, n- or iso-propyl.

The phrase "if present, $R^{15}$, $R^{16}$, $R^{17}$ and $R^{18}$" as used herein means that if Z' or Z" represent >N—R° with R° being formula (VII) and/or for Z* or Z** represent >N—R˙ with R˙ being formula (VII), then residues $R^{15}$, $R^{16}$, $R^{17}$ and $R^{18}$ of formula (VII) may form a ring as described above with any one of $R^5$, $R^6$, $R^7$, $R^8$, $R^9$, $R^{10}$, R°, $R^{11}$, $R^{12}$, $R^{13}$, $R^{14}$, R˙. However, it is readily understood that R° represented by formula (VII) cannot form a ring with itself, i.e. with its residues $R^{15}$, $R^{16}$, $R^{17}$ and $R^{18}$. This likewise applies for R˙ represented by formula (VII).

The term "geminal groups" as used herein means that two residues are bound to the same atom.

The term "vicinal groups" as used herein means that two residues are respectively bound to adjacent atoms.

Preferably, in formula (V) or (VI) of compound of formula (IV), any two residues of $R^5$, $R^6$, $R^7$, $R^8$, $R^9$, $R^{10}$, R° may represent together an alkylene or alkenylene group forming together with the bridging atoms to which they are linked a 3- to 8-membered saturated or unsaturated ring, wherein the alkylene or alkenylene group may be substituted by an alkoxy group, an acidic group or a —NR▲ R▼ group wherein R▲ and R▼ independently from each other represent a hydrogen atom or an alkyl group.

Likewise, it is preferred for formula (VIII) or (IX) of coinitiator compound of formula (IV) that any two residues of $R^{11}$, $R^{12}$, $R^{13}$, $R^{14}$, R˙ may represent together an alkylene or alkenylene group forming together with the bridging atoms to which they are linked a 3- to 8-membered saturated or unsaturated ring wherein the alkylene or alkenylene group may be substituted by an alkoxy, an acidic group or a —NR▲ R▼ group wherein R▲ and R▼ independently from each other represent a hydrogen atom or an alkyl group.

Besides of the above preferred ring formations for formula (V) or (VI) and (VIII) or (IX), residues which are not geminal or vicinal groups may represent together a single bond forming together with the bridging atoms to which the residues are linked a 3- to 8-membered saturated or unsaturated ring. Specifically, residues $R^5$, $R^6$ or $R^{10}$ together with any one of residues $R^7$, $R^8$, $R^9$ and R° of Z', residues $R^{11}$, $R^{12}$ or $R^{14}$ together with $R^{13}$ or R˙ of Z*, or residues $R^7$ and $R^{14}$, $R^8$ and $R^{13}$, $R^{15}$ and $R^{17}$ or $R^{18}$ may form together a single bond forming together with the bridging atoms to which they are linked a 3- to 8-membered saturated or unsaturated ring.

More preferably, in formula (IV), one or more rings are formed within formula (V)/(VI) and/or formula (VIII)/(IX), wherein it is preferred that one ring is formed in formula (V) or (VI) and one ring is formed in formula (VIII) or (IX). Specifically, any two residues $R^5$, $R^6$, $R^7$, $R^8$, $R^9$, $R^{10}$, R° in formula (V) or (VI) and/or any two residues of $R^{11}$, $R^{12}$, $R^{13}$, $R^{14}$, R˙ in formula (VIII) or (IX) may represent together an alkylene or alkenylene group forming together with the bridging atoms to which they are linked a 3- to 8-membered saturated or unsaturated ring, wherein the alkylene or alkenylene group may be substituted by an alkoxy group, an acidic group or a —NR▲ R▼ group wherein R▲ and R▼ independently from each other represent a hydrogen atom or an alkyl group.

Furthermore, alternatively or in addition to the above described more preferred ring formations within formula (V)/(VI) and formula (VIII)/(IX), rings may be formed between residues of formula (V)/(VI) and residues of formula (VIII)/(IX). Specifically, residue $R^5$, $R^6$ or $R^{10}$ may represent together with any one of residues $R^7$, $R^8$, $R^9$ and R° of Z' a single bond or an optionally substituted alkylene or alkenylene group as described above, wherein said residues form together with the bridging atoms to which they are linked a 3- to 8-membered saturated or unsaturated ring.

In the compound of formula (IV), L may be present or absent. When present, L represents a divalent linker group, and when absent X' and X" are bonded directly by a single bond.

Preferably, in the coinitiator compound of formula (IV), L is a group of the following formula (X):

In formula (X), m, n and o, which may be the same or different are integers of from 0 to 3; and p is 0, 1 or 2. Preferably, p is 0 or 1. Further, it is preferred that n is 0. For m and o, it is preferred that m or o is 0. Preferably, in formula (X) m is 0, n is 0 or 1 and o is 0 to 3, more preferably m is 0, n is 0 or 1 and o is 0 or 1. Most preferably, in formula (X), m=n=o=0, that is L is absent and X' and X" are bonded directly by a single bond.

The coinitiator compound of formula (IV) may for example be readily prepared by means of a synthesis route as shown in Scheme 8:

Scheme 8: Exemplary synthesis route for preparing coinitiator compound of formula (IV)

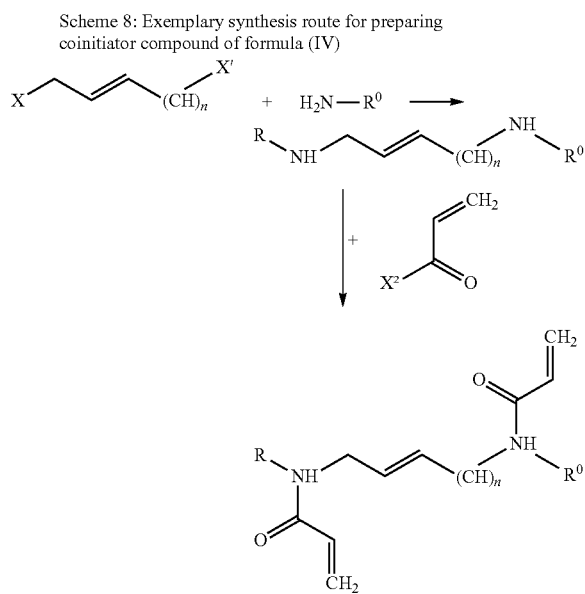

In Scheme 8, the synthesis route is exemplary depicted for the preparation of a coinitiator compound of formula (IV) wherein X' represents a group of formula (V) wherein $R^5$, $R^6$, $R^7$, $R^8$ and $R^9$ are hydrogen atoms, X" represents a group of formula (VIII) wherein $R^{11}$, $R^{12}$ and $R^{13}$ are hydrogen atoms, R' and R° are identical, and L is a single bond. X and X' represent suitable leaving groups which may for example be halogens such as Cl, Br, I, alkoxy, hydroxyl, alkyl- or aryl-sulfonic acid esters such as mesylate, tosylate and triflate, and X" may be a halogen atom such as Cl, Br and I. It is understood that instead of groups $R^5$, $R^6$, $R^7$, $R^8$, $R^9$, $R^{11}$, $R^{12}$ and $R^{13}$ representing hydrogen atoms, these groups can be varied and may also represent residues other than a hydrogen atom, namely such as defined above for said groups. Furthermore, it is understood that for obtaining coinitiator compounds of formula (IV) wherein $R^5$ is different from $R^{11}$ and/or $R^7$ is different from $R^{12}$ and/or R° is different from R', one of the leaving groups X and X' may be suitably protected or two leaving groups X and X' having different reactivity may be provided. Then, after subsequent reaction with a first amine compound of formula $H_2N$—R° and a first (meth)acrylic acid derivative X"—C(=O)—$CR_2$=$CHR_1$, the protected leaving group X or X' may be deprotected or alternatively, the less reactive, substantially unreacted leaving group X or X' is reacted with a second amine compound of formula $H_2N$—R' and a second (meth)acrylic acid derivative X"—C(=O)—$CR^{12}$=$CHR^{11}$. The protecting group of a(n) (optionally) protected leaving group X or X' or protecting groups having different reactivity are not particularly limited and may be any conventional protecting group, for example, described in P.G.M. Wuts and T. W. Greene, Greene's Protective Groups in Organic Synthesis, $4^{th}$ Edition, John Wiley and Sons Inc., 2007.

It is particularly preferred that in compounds of formula (IV), L represents a single bond and the dotted line between $CR^8$ and $CR^9$ represents a double bond, while X' represents a group of formula (V) and X" represents a group of formula (VIII), or X' represents a group of formula (VI) and X" represents a group of formula (IX). Furthermore, it is preferred that in such compound of formula (IV), Z represents a group N—R and Z' represents a group N—R'. Most preferably, in compound of formula (IV), the selection of $R^5$, $R^6$, $R^7$, $R^8$, $R^9$, $R^{10}$, $R^{15}$, $R^{17}$, $R^{18}$, $R^{18}$, Z', Z" of formula (V) and (VI) is identical with the selection of $R^{11}$, $R^{12}$, $R^{13}$, $R^{14}$, $R^{15}$, $R^{16}$, $R^{17}$, $R^{18}$, Z*, Z** of formula (VIII) and (IX).

Preferably, residues R° and $R^8$ and/or residues R' and $R^9$ may represent together a single bond, an alkylene group or an alkenylene group forming together with the bridging atoms to which they are linked a 3- to 6-membered saturated or unsaturated ring. This ring may be in the form of 1H-azirine-1,3-diyl, 1-azetine-1,3-diyl, 1-pyrolin-1,4-diyl, 1-pyrolin-1,4-diyl, 2-pyrolin-1,4-diyl, 1,2-diyhdropyridine-1,5-diyl, 2,3-diyhdropyridine-1,5-diyl or 3,4-diyhdropyridine-1,5-diyl, more preferably 1-pyrolin-1,4-diyl, 2-pyrolin-1,4-diyl, 1,2-diyhdropyridine-1,5-diyl, 2,3-diyhdropyridine-1,5-diyl or 3,4-diyhdropyridine-1,5-diyl. Preferred rings are in the form of 4- to 6-membered saturated or unsaturated rings in the form of 1-pyrolin-1,4-diyl, 1-pyrolin-1,4-diyl, 2-pyrolin-1,4-diyl, 1,2-diyhdropyridine-1,5-diyl, 2,3-diyhdropyridine-1,5-diyl or 3,4-diyhdropyridine-1,5-diyl, more preferably 1-pyrolin-1,4-diyl, 2-pyrolin-1,4-diyl, 1,2-diyhdropyridine-1,5-diyl, 2,3-diyhdropyridine-1,5-diyl or 3,4-diyhdropyridine-1,5-diyl. Most preferred is 3,4-diyhydropyridine-1,5-diyl. Furthermore, it is preferred that the rings formed by residues R° and $R^8$ as well as residues $R^1$ and $R^9$ together with the bridging atoms to which they are linked are identical.

Alternatively to the above described ring formation of residues R° and $R^8$ and/or residues $R^1$ and $R^9$, in formula (IV), residues $R^7$ and $R^{13}$ or residues $R^8$ and $R^{13}$ may represent together a single bond, an alkylene or alkenylene group forming together with the bridging atoms to which they are linked a 3- to 8-membered saturated or unsaturated ring, wherein it is preferred that 3- to 6-membered unsaturated rings are formed having one or two carbon-carbon-double bonds. Preferably, residues $R^7$ and $R^{13}$ or residues $R^8$ and $R^{13}$ form together with L representing a single bond or an alkylene or alkenylene group an unsaturated ring selected from the group consisting of cyclobutene-diyl, cyclopentene-diyl, cyclohexene-diyl and cyclohexadiene-diyl, wherein $R^8$ and $R^{13}$ may also form a three-membered ring in the form of cyclopropene-diyl.

Alternatively or additionally to the above described ring formations of residues R° and $R^8$, residues R' and $R^9$, residues $R^7$ and $R^{13}$ and residues $R^8$ and $R^{13}$, if present, any two residues of $R^5$, $R^{16}$, $R^{17}$ and $R^{18}$ may form a ring. Preferably, $R^{15}$ may represent together with $R^{17}$ or $R^{18}$ a single bond or an alkylene or alkenylene group forming together with the bridging atoms to which they are linked a 3- to 8-membered saturated or unsaturated ring, wherein it is preferred that 3- to 6-membered unsaturated rings are formed having one or two carbon-carbon-double bonds. Most preferably, $R^{15}$ together with $R^{17}$ or $R^{18}$ form with the bridging atoms to which they are linked a 1-cyclopropene-3-yl, 1-cyclobutene-3-yl, 1-cyclopentene-3-yl, 1,3-cyclopentadiene-5-yl, 1-cycloxene-3-yl and 1,4-cyclohexadiene-6-yl.

For example, coinitiator compounds of formula (IV) may have the following structural formulae, wherein $R^7$, $R^{10}$, $R^{13}$, $R^{14}$, $R°$, $R'$, $Z'$, $Z''$, $Z^*$, $Z^{**}$ and o have the same meaning as defined above:

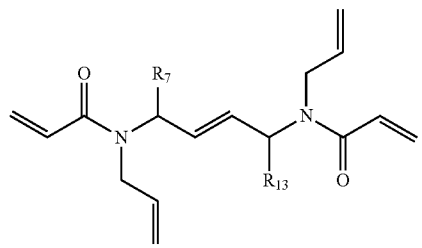

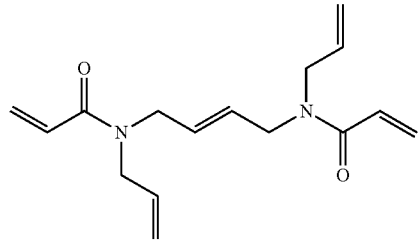

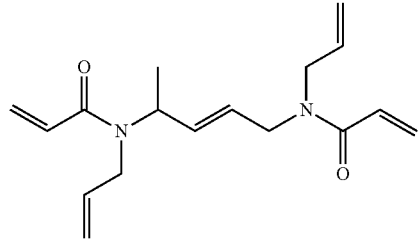

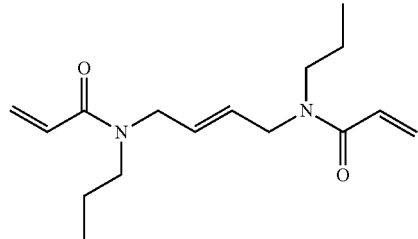

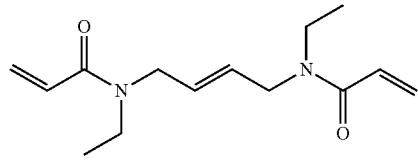

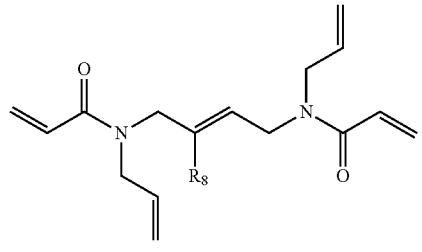

-continued

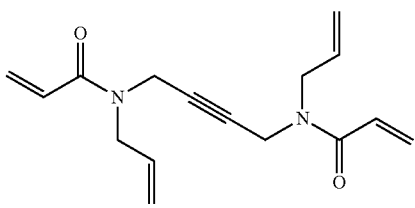

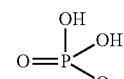

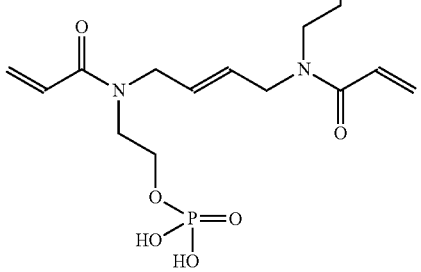

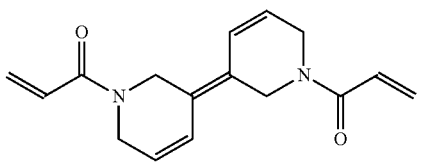

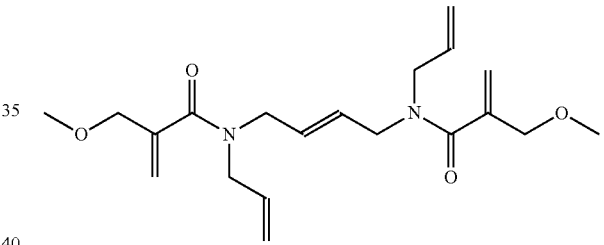

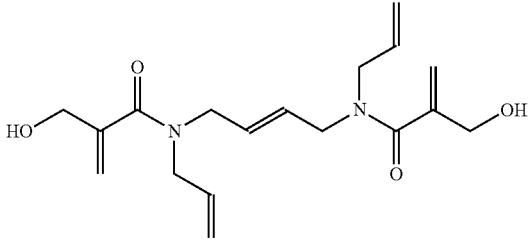

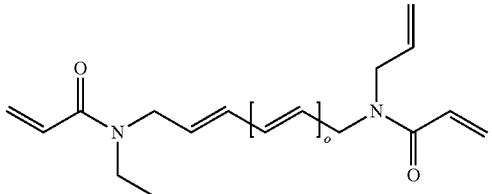

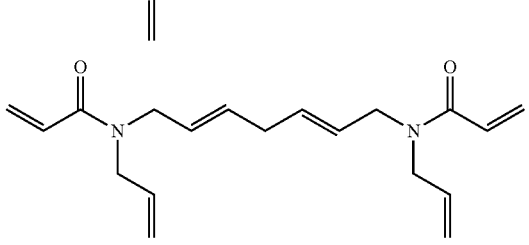

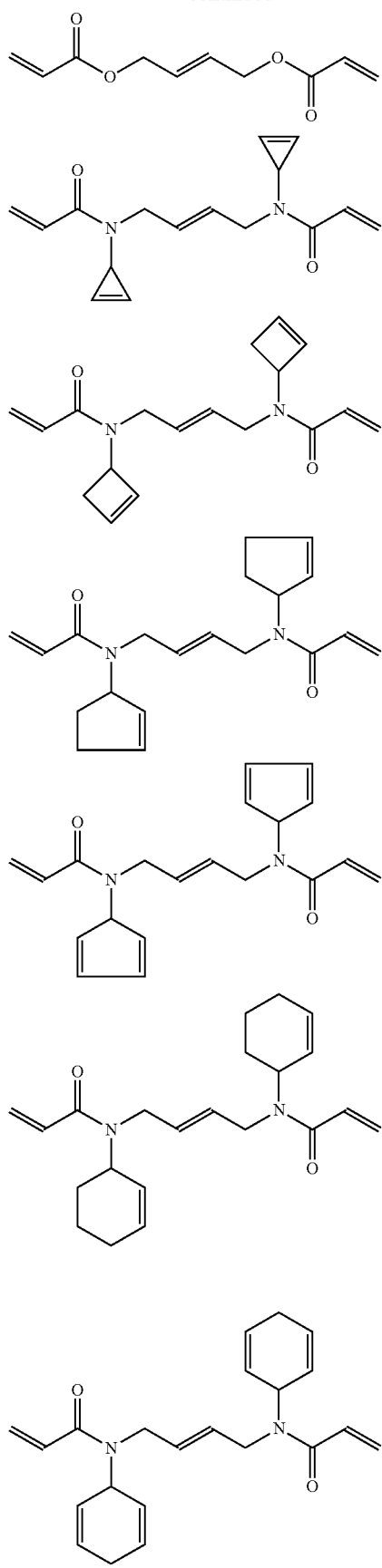
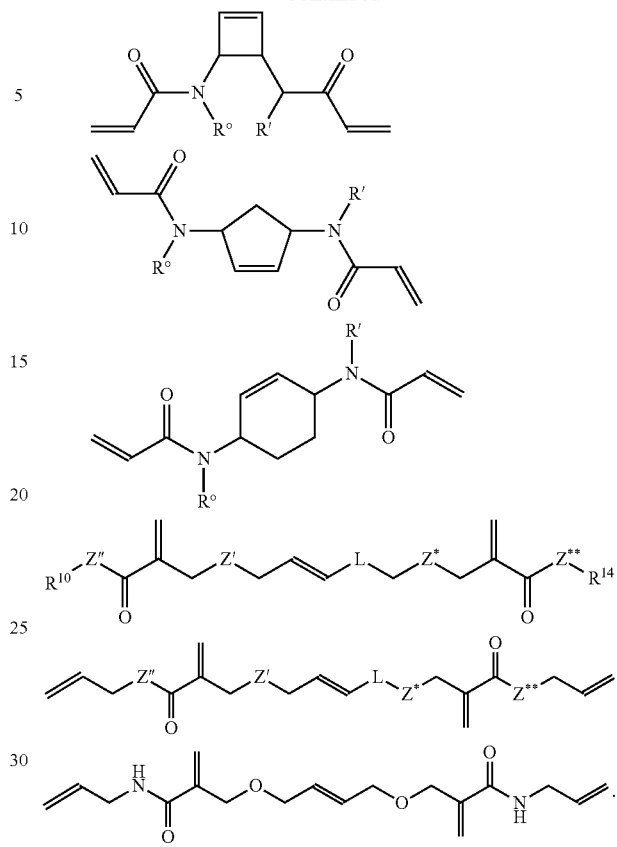
Preferably, coinitiator compounds of formula (IV) have the following structural formulae:
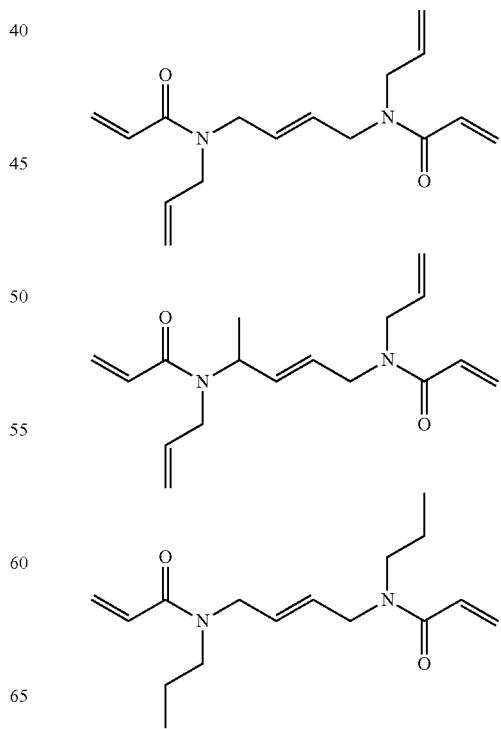

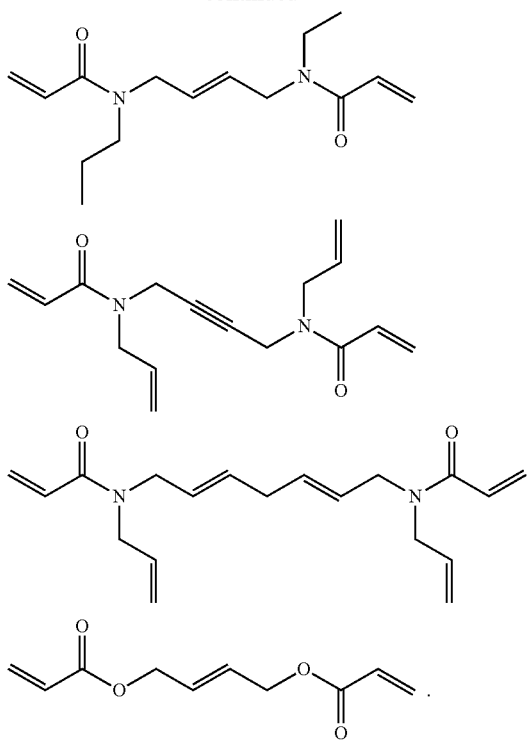

More preferably, coinitiator compounds of formula (IV) have the following structural formulae:

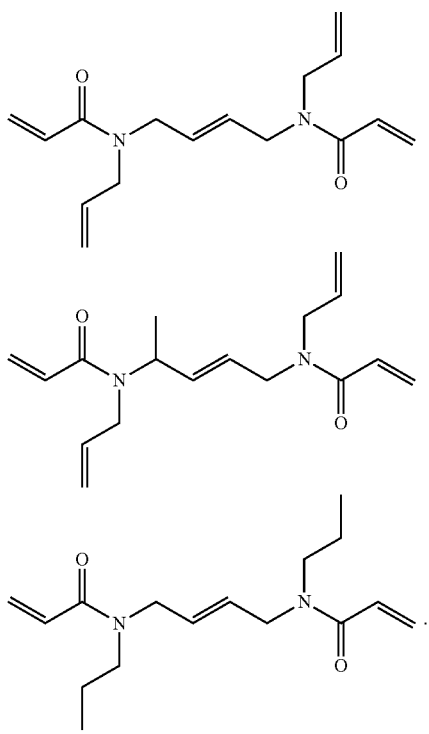

Most preferably, coinitiator compound of formula (IV) is N,N'-diallyl-1,4-bisacrylamido-(2E)-but-2-en (BAABE). BAABE has the following structural formula:

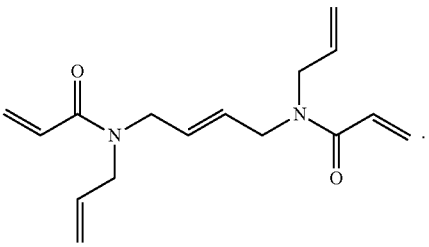 [SMILES: C=CCN(C/C=C/CN(CC=C)C(=O)C=C)C(=O)C=C]

Preferably, the coinitiator compound of formula (IV) has a refractive index in the range of from 1.500 to 1.580.

The initiator system may further comprise one or more components selected from (a3) an iodonium salt, a sulfonium salt and a phosphonium salt.

Preferably, the iodonium, sulfonium and phosphonium salts are selected from the following group:

(1) an iodonium compound of the following formula (XIII):

wherein
$R^{23}$ and $R^{24}$
which are independent from each other, represent an organic moiety, and
$A^-$ is an anion;

(2) a sulfonium compound of the following formula (XIV):

wherein
$R^{25}$, $R^{26}$ and $R^{27}$
which are independent from each other, represent an organic moiety or wherein any two of $R^{25}$, $R^{26}$ and $R^{27}$ form a cyclic structure together with the sulfur atom to which they are bound, and
$A^-$ is an anion;

(3) a phosphonium compound of the following formula (XV):

wherein
$R^{28}$, $R^{29}$ and $R^{30}$
which are independent from each other, represent an organic moiety, and
$A^-$ is an anion.

In the iodonium compounds of formula (XIII), $R^{23}$ and $R^{24}$ preferably represent an aromatic, an aliphatic or an alicyclic group. An aromatic group may be a phenyl group. The phenyl group may be substituted by one or more straight chain or branched alkyl groups having 1 to 6 carbon atoms, straight chain or branched alkoxy groups having 1 to 6 carbon atoms, aromatic groups such as aryl groups or aryloxy groups, alicyclic groups having 3 to 6 carbon atoms, halogen atoms, hydroxyl groups, or amino groups. The aliphatic group may be a straight chain or branched alkyl groups having 1 to 6 carbon atoms which may be substituted by one or more aromatic groups, alicyclic groups having 3 to 6 carbon atoms, halogen atoms, hydroxyl groups or amino groups. An alicyclic group may be a group having 3 to 6 carbon atoms which may be substituted by one or more aromatic groups, aliphatic groups, halogen atoms, hydroxyl groups or amino groups.

According to a preferred embodiment, the iodonium compound of formula (XIII) is a diaryl iodonium salt. Examples of useful diaryl iodonium salt include di(4-tertbutylphenyl)-iodonium (DTPI) hexafluorophosphate, DTPI tetrafluoroborate, DTPI hexafluoroantimonate, DTPI hexafluoroarsenate, (4-methylphenyl)[4-(2-methylpropyl) phenyl] iodonium hexafluoroantimonate, (4-methylphenyl) [4-(2-methylpropyl) phenyl] iodonium tetrafluoroborate, diphenyliodonium (DPI) tetrafluoroborate, di(4-methylphenyl)iodonium (Me2-DPI) tetrafluoroborate, phenyl-4-methylphenyliodonium tetrafluoroborate, di(4-heptylphenyl)iodonium tetrafluoroborate, di(3-nitrophenyl)iodonium hexafluorophosphate, di(4-chlorophenyl)iodonium hexafluorophosphate, di(naphthyl)iodonium tetrafluoroborate, di(4-trifluoromethylphenyl)iodonium tetrafluoroborate, DPI hexafluorophosphate, Me2-DPI hexafluorophosphate; DPI hexafluoroarsenate, di(4-phenoxyphenyl)iodonium tetrafluoroborat, phenyl-2-thienyliodonium hexafluorophosphate, 3,5-dimethylpyrazolyl-4-phenyliodonium hexafluorophosphate, DPI hexafluoroantimonate, 2,2'-DPI tetrafluoroborate, di(2,4-dichlorophenyl)iodonium hexafluorophosphate, di(4-bromophenyl)iodonium hexafluorophosphate, di(4-methoxyphenyl)iodonium hexafluorophosphate, di(3-carboxyphenyl)iodonium hexafluorophosphate, di(3-methoxycarbonylphenyl)iodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, and DPI hexafluorophosphate.

Particularly preferred iodonium compounds of formula (XIII) include diaryl iodonium salts such as di(4-tert-butylphenyl)-iodonium (DTPI) hexafluorophosphate, diphenyliodonium (DPI) hexafluorophosphate, di(4-methylphenyl) iodonium (Me2-DPI) hexafluorophosphate, diaryliodonium hexafluoroantimonate, (4-methylphenyl)[4-(2-methylpropyl) phenyl] iodonium hexafluoroantimonate, (4-methylphenyl)[4-(2-methylpropyl)phenyl]iodonium hexafluorophosphate (Irgacure® 250, commercial product available from BASF SE), (4-methylphenyl)[4-(2-methylpropyl) phenyl] iodonium tetrafluoroborate, 4-octyloxyphenyl phenyliodonium hexafluoroantimonate, 4-(2-hydroxytetradecyloxyphenyl)phenyliodonium hexafluoroantimonate, and 4-(1-methylethyl)phenyl 4-methylphenyliodonium tetrakis (pentafluorophenyl)borate.

According to a particularly preferred embodiment, the iodonium compounds of formula (XIII) are selected from the group consisting of diaryliodonium hexafluorophosphates, wherein di(4-tert-butylphenyl)-iodonium (DTPI) hexafluorophosphate, DPI hexafluorophosphate, di(4-methylphenyl)iodonium (Me2-DPI) and 4-methylphenyl)[4-(2-methylpropyl)phenyl]iodonium hexafluorophosphate (Irgacure® 250, commercial product available from BASF SE) are most preferred.

According to a preferred embodiment, the dental composition contains the iodonium compound of the following formula (XIII) as the further component (a3), preferably in the form of a di(4-tert-butylphenyl)-iodonium (DTPI), diphenyl iodonium (DPI) or di(4-methylphenyl)iodonium (Me2-DPI) compound, most preferably di(4-tert-butylphenyl)-iodonium (DTPI), in an amount from 0.001 to 2 percent by weight based on the total weight of the composition.

A preferred sulfonium compound of the formula (XIV) is S-(phenyl)thianthrenium hexafluorophosphate of the following formula:

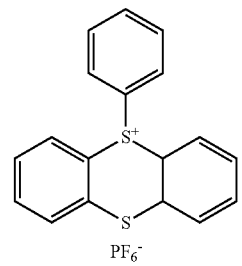

The phosphonium compound of formula (XV) may be a tetrakis-(hydroxymethyl)-phosphonium (THP) salt or a tetrakis-(hydroxymethyl)-phosphonium hydroxide (THPOH) salt, wherein the anion $A^-$ is selected from the group consisting of formate, acetate, phosphate, sulphate, fluoride, chloride, bromide and iodide.

In a salt of a compound of any one of formula (XIII) to (XV), the anion may be an anion selected from halogenides such as chloride, bromide and iodide, hexafluorophosphate, tetrafluoroborate, tetraphenylborate, hexafluoroantimonate and trifluoromethylsulfonate. The use of (a1) a sensitizer compound of formula (I) and (a2) the coinitiator compound of formula (IV) together with (a3) an optional iodonium-, sulfonium or phosphonium salt provides for a synergistic effect, in particular in the case of iodonium salts.

Preferably, the initiator system (a) comprises a combination of components (a1), (a2) and (a3). More preferably, the initiator system (a) comprises:
    (a1) a sensitizer compound of formula (I),
    (a2) a coinitiator compound of formula (IV), and optionally additionally a coinitiator being an 1,2 diketone photoinitiator, and
    (a3) a iodonium salt, a sulfonium salt or a phosphonium salt.

According to a particularly preferred embodiment, initiator system (a) comprises
    (a1) a sensitizer compound of formula (I), preferably selected from the group consisting of tert-butyl (tert-butyldimethylsilyl)glyoxylate) (DKSi), benzoyldiphenylmethylsilane (BDMSi) and benzoyltrimethylsilane (BTMSi), most preferably DKSi,
    (a2) a coinitiator compound of formula (IV), and optionally additionally camphor quinone (CQ), and
    (a3) a diphenyliodonium (DPI) salt, preferably a di(4-tert-butylphenyl)-iodonium (DTPI) salt, most preferably DTPI hexafluorophosphate.

Owing to synergistic effects between components (a1), (a2) and (a3), a higher conversion rate of the compounds having a polymerizable double bond (a) and more advantageous kinetics in terms of the polymerization time can be obtained compared with an initiator system consisting of (a1). Furthermore, an initiator system comprising components (a1), (a2) and (a3) is particularly suitable for polymerizing relatively thin films of up to 0.1 mm, such as adhesive films, as well as for relative thick samples having a thickness of about 1 to 2 mm or more, such as fillings and prosthetics. Besides, an initiator system comprising components (a1), (a2) and (a3) provides for good bleaching, that is, colorless polymers are obtained. When camphor quinone (CQ) is used as additional coinitiator, for the initiator system comprising components (a1), (a2) and (a3), the aforementioned effects are significantly improved compared to a conventional initiator system consisting of camphor quinone (CQ) as polymerisation initiator in combination with components (a2) and (a3).

Preferably, the initiator system further comprises
(a4) an aromatic tertiary phosphine compound of the following formula (XI):

wherein
Z''' is a group of the following formula (XII)

wherein
R$^{20}$ represents a substituted or unsubstituted hydrocarbyl group;
Ar represents a substituted or unsubstituted aryl or heteroaryl group;
R$^{19}$ is a substituted or unsubstituted hydrocarbyl group or a group L'Z$^{iv}$, wherein
L' is a substituted or unsubstituted divalent hydrocarbyl group which may contain a linkage selected from an ether linkage, a thioether linkage, an ester linkage, an amide linkage, and a urethane linkage and
Z$^{iv}$ has the same meaning as Z''', whereby Z''' and Z$^{iv}$ may be the same or different;
wherein the group R$^{19}$ and Ar may be substituted by one or more groups selected from a hydroxyl group, an oxo group, a —NR$^{21}$R$^{22}$ group (wherein R$^{21}$ and R$^{22}$, which may be the same or different, are selected from a hydrogen atom and C$_{1-6}$ alkyl groups), a carboxyl group, and a group having a polymerizable double bond, and
R$^{19}$ and L' may be substituted by one or more groups selected from a hydroxyl group, an oxo group, a —NR$^{21}$R$^{22}$ group (wherein R$^{21}$ and R$^{22}$, which may be the same or different, are selected from a hydrogen atom and C$_{1-6}$ alkyl groups), a carboxyl group, and a group having a polymerizable double bond.

In the aromatic tertiary phosphine compound of the formula (XI), moieties R$^{20}$, Ar, L', R$^{19}$, Z''' and Z$^{iv}$ may be defined as follows:

For R$^{20}$, the monovalent hydrocarbyl group may be an alkyl group, a cycloalkyl group, a cycloalkylalkyl group, an arylalkyl group or an aryl group.

Ar represents a substituted or unsubstituted aryl or heteroaryl group. An aryl group may be selected from a phenyl group, a naphtyl group, a tolyl group, a xylyl group, and a styryl group. A heteroaryl group may be a pyridyl group.

L' is a substituted or unsubstituted divalent hydrocarbyl group which may contain a linkage selected from an ether linkage, a thioether linkage, an ester linkage, an amide linkage, and a urethane linkage. For L', the divalent hydrocarbyl group may be an alkyldiyl group, a cycloalkyldiyl group, a cycloalkylalkyl-diyl group, an arylalkyl-diyl group or an aryldiyl group. In a cycloalkylalkyl-diyl, one valency may be bonded to each of the cycloalkyl moiety or the alkyl moiety, or both valencies may be bonded to either the cycloalkyl moiety or the alkyl moiety. In a arylalkyl-diyl group, each of the aryl moiety or the alkyl moiety may be monovalent respectively, or either the aryl moiety or the alkyl moiety is divalent, while the other moiety is nonvalent. In a cycloalkylalkyl-diyl, each of the cycloalkyl moiety or the alkyl moiety may be monovalent respectively, or either the cycloalkyl moiety or the alkyl moiety is divalent, while the other moiety is nonvalent.

The following definitions apply both for the monovalent and the divalent hydrocarbyl group, therefore, for the definition of the divalent hydrocarbyl group, the suffixes "diyl" and "-diyl" are bracketed.

An alkyl(diyl) group may be straight-chain or branched C$_{1-20}$ alkyl(diyl) group, typically a C$_{1-8}$ alkyl(diyl) group. Examples for a C$_{1-6}$ alkyl(diyl) group can include linear or branched alkyl(diyl) groups having 1 to 6 carbon atoms, preferably 1 to 4 carbon atoms, for example, methyl(diyl), ethyl(diyl), n-propyl(diyl), isopropyl(diyl), n-butyl(diyl), isobutyl(diyl), sec-butyl(diyl), tert-butyl(diyl), n-pentyl (diyl), isopentyl(diyl) and n-hexyl(diyl).

A cycloalkyl(diyl) group may be a C$_{3-20}$ cycloalkyl(diyl) group. Examples of the cycloalkyl(diyl) group can include those having 3 to 14 carbon atoms, for example, cyclopropyl (diyl), cyclobutyl(diyl), cyclopentyl(diyl) and cyclohexyl (diyl). A cycloalkylalkyl(diyl) group can include those having 4 to 20 carbon atoms.

A cycloalkylalkyl(-diyl) group can include a combination of a linear or branched alkyl(diyl) group having 1 to 6 carbon atoms and a cycloalkyl(diyl) group having 3 to 14 carbon atoms. Examples of the cycloalkylalkyl(-diyl) group can for example, include methylcyclopropyl(-diyl) methylcyclobutyl(-diyl), methylcyclopentyl(-diyl), methylcyclohexyl(-diyl), ethylcyclopropyl(-diyl), ethylcyclobutyl(-diyl), ethylcyclopentyl(-diyl), ethylcyclohexyl(-diyl), propylcyclopropyl(-diyl), propylcyclobutyl(-diyl), propylcyclopentyl(-diyl), propylcyclohexyl(-diyl).

An arylalkyl(-diyl) group may be a C$_{7-20}$ arylalkyl(-diyl) group, typically a combination of a linear or branched alkyl(diyl) group having 1 to 6 carbon atoms and an aryl(-diyl) group having 6 to 10 carbon atoms. Specific examples of an arylalkyl(-diyl) group are a benzyl(-diyl) group or a phenylethyl(-diyl) group.

An aryl(diyl) group can include aryl(diyl) groups having 6 to 10 carbon atoms. Examples of the aryl(diyl) group are phenyl(diyl) and naphtyl(diyl). Aryl(diyl) groups may contain 1 to 3 substituents. Examples of such substituents can include halogen atoms, a cyano group, a hydroxy group, an amino group, C$_{1-6}$ alkyl groups and C$_{1-6}$ alkoxy groups. Here, illustrative of the halogen atoms can be fluorine, chlorine, bromine and iodine. The C$_{1-4}$ alkyl(diyl) groups are, for example, methyl(diyl), ethyl(diyl), n-propyl(diyl), isopropyl(diyl) and n-butyl(diyl). Illustrative of the C$_{1-4}$ alkoxy(diyl) groups are, for example, methoxy(diyl), ethoxy (diyl) and propoxy(diyl). The alkyl(diyl) moieties in these substituents may be linear, branched or cyclic.

Preferably, the hydrocarbyl group is an aryl(diyl) group selected from a phenyl(diyl) group and a naphthyl(diyl) group, which groups may optionally be substituted by one to three groups selected from halogen atoms, a cyano group, an amino group, a hydroxy group, C$_{1-6}$ alkyl groups and C1-6 alkoxy groups, or wherein the hydrocarbyl group is a non-aromatic hydrocarbyl group selected from a straight chain or branched alkyl group, a straight chain or branched alkenyl group, or a straight chain or branched alkynyl group.

The C$_{1-8}$ alkyl(diyl) group and the C$_{3-14}$ cycloalkyl(diyl) group may optionally be substituted by one or more members of the group selected from a C$_{1-4}$ alkyl group, C$_{1-4}$ alkoxy group, a phenyl group, and a hydroxy group. Examples for a C$_{1-4}$ alkyl group can include linear or branched alkyl groups having 1 to 4 carbon atoms, for example, methyl, ethyl, n-propyl, isopropyl, n-butyl, isobutyl, sec-butyl, tert-butyl. Examples for an C$_{1-4}$ alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

Moreover, in formula (XI), any of the hydrocarbyl group may be substituted by one or more groups selected from halogen atoms, a cyano group, an amino group or a hydroxy group. Accordingly, in the hydrocarbyl groups some or all hydrogen atoms are replaced by halogen atoms (e.g., fluoro, bromo, chloro), for example, halo-substituted alkyl groups such as chloromethyl, chloropropyl, bromoethyl and trifluoropropyl, and cyanoethyl.

In case the hydrocarbyl group contains an alkyl(diyl) chain, one or more carbon atoms in the alkyl(diyl) chain may be replaced by an oxygen atom, a sulfur atom, an amide group, an ester group, or a urethane group. In case the hydrocarbyl group is an alkyl group having more than one carbon atom, the alkyl group contains an alkylene. Accordingly, in case the hydrocarbyl group is an n-hexyl group, any of the carbon atoms of the alkylene chain excluding the terminal methyl group may be replaced by an oxygen atom, a sulfur atom, an amide group, an ester group, a urethane group or an NH group. Therefore, the following groups may be given as specific examples in case of one or more oxygen atoms:

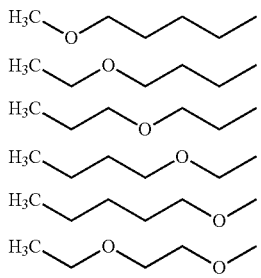

In formula (XI), group $R^{20}$ and/or Ar as well as $R^{19}$ and/or may be substituted with a polymerizable double bond, preferably a carbon-carbon double bond. Examples of polymerizable carbon-carbon double bonds include vinyl, conjugated vinyl, allyl, acryl, methacryl and styryl. Preferably, the polymerizable double bond is selected from the group consisting of methacryl, acryl and styryl. More preferably, the double bond is styryl.

Preferably, $R^{20}$ and Ar independently are aromatic hydrocarbyl groups selected from a phenyl group, a naphtyl group, a tolyl group, a xylyl group, and a styryl group.

As regards $R^{19}$, this moiety is preferably an aryl group, which may be substituted by one or more groups selected from a hydroxyl group, an amino group, a —$NR^{21}R^{22}$ group (wherein $R^{21}$ and $R^{22}$, which may be the same or different, are selected from $C_{1-6}$ alkyl groups), a carboxyl group, and a group having a polymerizable double bond. Alternatively, $R^{19}$ is preferably a group L'$Z^{iv}$ wherein $Z^{iv}$ and Z''' are the same.

More preferably, $R^{19}$ is a $C_{1-6}$ alkyl group or a $C_{1-6}$ alkenyl group, which groups may be substituted by one or more groups selected from a hydroxyl group, an amino group, a —$NR^{21}R^{22}$ group (wherein $R^{21}$ and $R^{22}$, which may be the same or different, are selected from $C_{1-6}$ alkyl groups), a carboxyl group, and a group having a polymerizable double bond. The group having a polymerizable double bond may be vinyl group, an allyl group, a (meth) acryloyloxy group or a (meth) acryloylamido group.

Even more preferably, the aromatic phosphine compound is a compound of formula (XI) wherein Z''' is a group of the following formula (XII'):

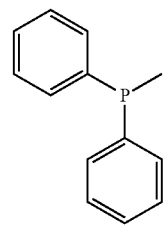

Specific examples for a compound of formula (XI) include triphenyl phosphine (TPP), 4-(diphenylphosphino) styrene (DPPS), 4-(diphenylphosphino)benzoic acid, 4-(diphenylphosphino) benzoic acid, 3-(diphenylphophonino) propionic acid, (4-(diphenylphosphino) N,N'-dimethylaniline, 2,2'-bis(diphenylphosphino)benzophenone (BDPPEP), bis[2-(diphenylphosphino)phenyl]ether (BD-PPE), (4-Hydroxyphenyl)diphenylphosphine, allyldiphenylphosphine. Preferably, the compound of formula (XI) is triphenyl phosphine (TPP) or 4-(diphenylphosphino)styrene (DPPS), more preferably 4-(diphenylphosphino)styrene (DPPS).

Aromatic tertiary phosphine compounds of formula (XI) may provide for both an advantageous efficiency in terms of a higher polymerisation rate and a higher final conversion rate compared to a dental composition comprising an initiator system without an aromatic tertiary phosphine compound of formula (XI). Advantageously, the polymeriation rate may be adjusted within a range which still provides for corrections when applying the dental composition to a patient's tooth or when forming a prosthesis. Although photopolymerization is achieved at a higher polymerisation and conversion rate, owing to the present initiator system, undesired side reaction resulting e.g. in discoloration of the cured dental composition can be effectively suppressed. Besides, by adding an aromatic tertiary phosphine compound of formula (XI) to the present initiator system, a yellow coloration of the dental composition eventually formed already before light curing can efficiently be reduced/decreased. That is, there is a photo-bleaching effect which provides for an advantageous effective reduction/decrease of yellow discolorations of the dental composition, while the initiator system furthermore provides for an advantageous polymerization and conversation rate throughout the whole course of time of the photopolymerization.

The present initiator system is not only advantageous for relatively thin films of up to 0.1 mm such as adhesive films, but also particularly suitable for polymerizing relative thick samples of a dental composition having a thickness of about 1 to 2 mm or more, such as fillings and prosthetics.

Without wishing to be bound to theory, it is believed that a synergistic effect due to the combination of (a1) the sensitizer compound of formula (I) and (a2) the coinitiator together with (a3) the aromatic tertiary phosphine of formula (XI) is provided according to the present invention.

A further positive effect associated with the application of tertiary phosphines of formula (XI) is that owing to the tertiary phosphines of formula (XI), the present compositions may exhibit an advantageous storage stability, that is the compositions keep the above characteristics of an advantageous efficiency in terms of a higher polymerisation rate and a higher final conversion rate even after a long storage time, e.g. about 2 month.

From the above listed aromatic tertiary compounds of formula (XI), 4-(diphenylphosphino)styrene (DPPS) is particularly preferred, since this compound may provide for particularly improved photo-bleaching results compared to the already advantageous results obtained with triphenyl phosphine (TPP). Besides, DPPS may be particularly suitable for initiating polymerization of thick samples of about 1 to 2 mm thickness. Besides, DPPS not only may provide for an improved conversion rate, but with DPPS, the conversion rate of the dental composition may be maintained even after a storage time of 2 weeks or more.

Preferably, in the present dental composition, the initiator system comprises component (a1), (a2), (a3) and (a4) in a molar ratio ((a1):(a2):(a3):(a4)) of 1: (0.0 to 3.0):(0.0 to 3.0):(0.0 to 3.0), more preferably 1: (0.1 to 2.0):(0.1 to 2.0):(0.1 to 2.0), even more preferably 1:(0.2 to 1.0):(0.2 to 1.0):(0.2 to 1.0). It is preferred that in the aforementioned molar ratio, the amount of the aromatic tertiary phosphine (a4) is 0.1 or higher. Because, when the amount of the aromatic tertiary phosphine (a4) is less than 0.1, then the conversion rate of the compounds having a polymerizable double bond, and the reaction rate of the polymerization reaction (in the following termed "polymerization rate") may be low. By means of the addition of the optional coinitiator (a2) and/or the optional (a3) iodonium salt, sulfonium salt or phosphonium salt, both conversion rate and polymerization rate can be further advantageously adjusted.

Besides of (a) the coinitiator compound of formula (IV), the dental composition may further comprise an additional coinitiator (a5). The dental composition may comprise one or more additional coinitiator(s) (a5).

The additional coinitiator (a5) may be selected from compounds having a Si—H or Ge—H bond, photoinitiators other than compound of formula (I), and electron donors.

The additional coinitiator (a5) may be a compound having a Si—H or Ge—H bond. Preferably, compounds having a Si—H or Ge—H bond are trihydrocarbylsilanes or trihydrocarbylgermanes in which the three hydrocarbyl groups have the same meaning as defined for $R_1$, $R_2$ and $R_3$. More preferably, the compound having a Si—H or Ge—H bond is triphenylsilicium hydride ($Ph_3SiH$) or triphenylgermanium hydride ($Ph_3GeH$), most preferably triphenylgermanium hydride ($Ph_3GeH$).

The additional coinitiator (a5) may be a sensitizer other than the sensitizer compound of formula (I). Such a sensitizer may for example be added to improve the matching of the emission spectrum of dental LED with the absorption of the photo-initiating system. For example, if sensitizer compound of formula (I) does not or not sufficiently absorb light within the range of 450 to 500 nm, it is preferred to add a sensitizer having a good absorbtion within this range.

An additional coinitiator (a5) in the form of a sensitizer other than sensitizer compound of formula (I) may be in the form of a Norrish type I or type II sensitizer.

The Norrish type I sensitizer may be selected from the group consisting of a triazine derivate, 2,4-6-trimethylbenzoyl-diphenylphosphine oxide (Irgacure® TPO), 2,4-6-trimethylbenzoyl-diphenylphosphinate (Irgacure® TPO-L, TPO-L), bis(2,4-6-trimethylbenzoyl)-phenylphosphineoxide (Irgacure® BAPO-X). Preferably, the Norrish type I sensitizer is a triazine derivative, preferably tris(trihaloalkyl)-triazine, more preferably tris(trihalomethyl)-triazine, even more preferably tris(trichloromethyl)-triazine and in particular 2,4,6-tris(trichloromethyl)-1,3,5-triazine.

Typical Norrish type II sensitizers are e.g a 1,2-diketone or a 1,3 diketone. Examples of suitable 1,2-diketones are camphor quinone, benzil, 2,2'-3 3'- and 4,4'-dihydroxylbenzil, 2,3-butanedione, 2,3-pentanedione, 2,3-hexanedione, 3,4-hexanedione, 2,3-heptanedione, 3,4-heptanedione, 2,3-octanedione, 4,5-octanedionefuril, biacetyl, 1,2-cyclohexanedione, 1,2-naphthaquinone, and acenaphthaquinone. Examples of suitable 1,3-diketones are dibenzoyl methane, benzoyl acetone and acetyl propionyl methane.

Preferably, the additional coinitiator (a5) is a Norrish type II sensitizer, more preferably a 1,2-diketone, most preferably camphor quinone.

By means of adding a sensitizer such as camphor quinone as an additional coinitiator (a5), the matching of the absorption of initiator system comprising (a) the sensitizer compound of formula (I) with the emission spectrum of an irradiation source may be improved compared to a conventional initiator system based on a conventional Norrish type I or II sensitizer.

The additional coinitiator (a5) may be an electron donor. Preferred electron donors include, for example, amines, amides, ethers, thioethers, ureas, thioureas, ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. Particularly preferred donors contain an electron donor atom such as a nitrogen, oxygen, phosphorus, or sulfur atom, and an abstractable hydrogen atom bonded to a carbon or silicon atom alpha to the electron donor atom.

For example, electron donors in the form of amine compounds are typically tertiary amines selected from the group consisting of triethanolamine, 4-N,N-dimethylaminobenzonitrile, methyl N,N-dimethylaminobenzoate, ethyl N,N-dimethylaminobenzoate (EDB), N,N-dimethylaminoethyl methacrylate and isoamyl 4-N,N-dimethylaminobenzoate, N,N-dimethylaniline, N,N-dimethyltoluidine, N,N-diethanoltoluidine, dimethylaminoanisole, 1 or 2-dimethylaminonaphthalene.

It is known that amine compounds, in particular aromatic amine compounds, may give rise to discoloration problems upon curing, since the amine compounds may partially decompose and/or react, which results in an undesired yellowing or even browning of the cured dental composition. In particular, aromatic amine compounds are problematic in view of discoloration.

Therefore, in case additional coinitiator (a5) is an amine compound, a non-aromatic amine compound is preferred. More preferably, the non-aromatic amine compound is triethanolamine or 4-N,N-dimethylaminoethyl methacrylate.

Most preferably, the present dental composition does not contain an amine compound as additional coinitiator (a5).

It is preferred that the additional coinitiator (a5) is a compound having a Si—H or Ge—H bond, optionally in combination with a sensitizer other than the sensitizer compound of formula (I).

It was surprisingly found that owing to (a2) the coinitiator compound of formula (IV), which significantly improves the capability of the (a) initiator system to promote polymerization rate and conversion rate of the polymerization upon curing, it may be dispensed with an additional coinitiator (a5).

Therefore, it is preferred that the present dental composition does not contain an additional coinitiator (a5).

Most preferably, the present dental composition does not contain any of (a3) iodonium salt, sulfonium salt and phosphonium salt, (a4) aromatic tertiary phosphine compound of formula (XI) or (a5) additional coinitiator, that is, the initiator system (a) essentially consists of (a1) the sensitizer compound of formula (I) and the coinitiator compound of formula (IV).

(b) Polymerizable Compounds Having at Least One Polymerizable Double Bond

The present dental composition may further comprise (b) one or more polymerizable compounds having at least one polymerizable double bond.

It is preferred that the coinitiator compound of formula (IV) is also comprised in the dental composition as a (b) polymerizable compound having at least one polymerizable double bond. For this purpose, compound of formula (IV) is preferably provided in an amount larger that the above indicated molar ratio in the initiator system of component (a1) and (a2) of 1: (0.0 to 3.0), in order to provide a significant amount of compound(s) of formula (IV) to be incorporated in the polymer of the cured dental composition.

Preferably, compounds of formula (IV) are provided as (b) polymerizable compound in which Z' and/or Z" represent >N—R° with R° being a group of formula (VII).

For use as both (a2) coinitiator and (b) polymerizable compound, it is preferred that the total amount of compound (s) of formula (IV) in the entire dental composition is at least 5% by weight, more preferably 10 to 50% by weight, even more preferably 12 to 40% by weight, and most preferably 15 to 30% by weight.

Since compound(s) of formula (IV) significantly improve the polymerization performance of the initiator system (a), it may be preferred to limit the amount of compound of formula (IV) within the dental composition when using it as both (a2) coinitiator and (b) polymerizable compound, in order to prevent a too exothermic polymerization. A too exothermic polymerization may cause an insufficient heat dissipation within a sample of dental composition upon curing, which may result in undesired partial degradation of the cured polymer. Such too highly exothermic polymerization may be avoided by limiting the total amount of compound(s) of formula (IV) in the entire dental composition to at most 70%, more preferably at most 60% by weight, even more preferably at most 45%, and most preferably at most 30%. Alternatively or additionally, too highly exothermic polymerization may be avoided by a better heat dissipation provided for example by suitably selecting the thickness of the dental composition sample to be cured. Preferably, the thickness is less than 1 mm, more preferably less than 0.5 mm.

Furthermore, the one or more polymerizable compounds having a polymerizable double bond may preferably be polymerizable N-substituted alkyl acrylic or acrylic acid amide monomers or a (meth)acrylate compounds.

A polymerizable N-substituted alkyl acrylic or acrylic acid amide monomer may be preferably selected from compounds of the following formulae (A), (B) and (C):

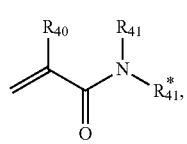
(A)

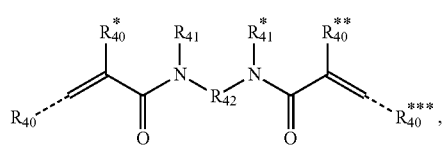
(B)

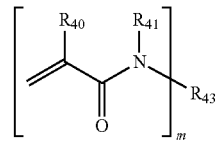
(C)

wherein $R_{40}$, $R^*_{40}$, $R^{}_{40}$, $R^{*}_{40}$ independently represent a hydrogen atom, —COOM, a straight chain or branched $C_1$ to $C_{18}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M, a $C_3$ to $C_{18}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M, or a $C_5$ to $C_{18}$ aryl or $C_3$ to $C_{18}$ heteroaryl group which may be substituted by —COOM, —PO$_3$M, —O—PO$_3$M$_2$ or —SO$_3$M, $R_{41}$ and $R^*_{41}$ independently represent a hydrogen atom, a straight chain or branched $C_1$ to $C_{18}$ alkyl group or $C_2$ to $C_{18}$ alkenyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M, a $C_3$ to $C_{18}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M, or a $C_5$ to $C_{18}$ aryl or $C_3$ to $C_{18}$ heteroaryl group which may be substituted by —COOM, —PO$_3$M, —O—PO$_3$M$_2$ or —SO$_3$M, $R_{42}$ represents a divalent substituted or unsubstituted organic residue having from 1 to 45 carbon atoms, whereby said organic residue may contain from 1 to 14 carbonyl groups or heteroatoms selected from oxygen, nitrogen and sulphur; preferably $R_{42}$ is a $C_1$ to $C_{18}$ alkylene group, which may contain 1 to 6 carbonyl groups or heteroatoms selected from oxygen, nitrogen and sulfur, and which may be substituted by a hydroxyl group, a $C_{6-14}$ aryl group, —COOM, —PO$_3$M, —O—PO$_3$M$_2$ or —SO$_3$M, wherein in said $C_1$ to $C_{18}$ alkylene group and said $C_2$ to $C_{18}$ alkenylene group, from 1 to 6 —CH$_2$-groups may be replaced by a —N—(C=O)—CR$_Z$=CH$_2$ group wherein $R_Z$ is a hydrogen atom or a $C_1$ to $C_{18}$ alkyl group, a substituted or unsubstituted $C_3$ to $C_{18}$ cycloalkyl group, a substituted or unsubstituted $C_4$ to $C_{18}$ aryl or heteroaryl group, a substituted or unsubstituted $C_5$ to $C_{18}$ alkylaryl or alkylheteroaryl group, a substituted or unsubstituted $C_7$ to $C_{30}$ aralkyl group, and a substituted or unsubstituted $C_2$ to $C_{45}$ mono-, di- or polyether group having from 1 to 14 oxygen atoms, $R_{43}$ represents a saturated di- or multivalent substituted or unsubstituted $C_2$ to $C_{18}$ hydrocarbon group, a saturated di- or multivalent substituted or unsubstituted cyclic $C_3$ to $C_{18}$ hydrocarbon group, a di- or multivalent substituted or unsubstituted $C_4$ to $C_{18}$ aryl or heteroaryl group, a di- or multivalent substituted or unsubstituted $C_5$ to $C_{18}$ alkylaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen atoms, and m is an integer, preferably in the range from 1 to 10, wherein M of any one $R_{40}$, $R^*_{40}$, $R^{}_{40}$, $R^{*}_{40}$, $R_{41}$, $R^*_{41}$, $R_{42}$ and $R_{43}$, which M are independent from each other, each represent a hydrogen atom or a metal atom.

For $R_{40}$, $R^*_{40}$, $R^{}_{40}$ and $R^{*}_{40}$, the straight chain or branched $C_1$ to $C_{18}$ alkyl group may e.g. be methyl, ethyl, n-propyl, i-propyl, n-butyl, isobutyl, tert-butyl, sec-butyl, pentyl or hexyl. For $R_{41}$ and $R^*_{41}$, the $C_{1-18}$ alkyl group or $C_{2-18}$ alkenyl group may e.g. be eth(en)yl, n-prop(en)yl, i-prop(en)yl, n-but(en)yl, isobut(en)yl, tert-but(en)yl sec-but(en)yl, pent(en)yl or hex(en)yl.

For $R_{40}$, $R^*_{40}$, $R^{}_{40}$, $R^{*}_{40}$, $R_{41}$ and $R^*_{41}$, an aryl group may, for example, be a phenyl group or a naphthyl group, and a $C_{3-14}$ heteroaryl group may contain 1 to 3 heteroatoms selected from nitrogen, oxygen and sulfur.

In formula (B), the dotted bond indicates that $R_{40}$ and $R^{***}_{40}$ may be in cis or trans configuration relative to CO.

Preferably, in formula (B), $R_{40}$, $R^*_{40}$, $R^{}_{40}$ and $R^{*}_{40}$ independently represent a hydrogen atom, —COOM, a straight chain or branched $C_{1-16}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M, a $C_{3-6}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M, a $C_{6-14}$ aryl or $C_{3-14}$ heteroaryl group which may be substituted by —COOM, —PO$_3$M, —O—PO$_3$M$_2$ or —SO$_3$M. More preferably, in formula (B), $R_{40}$, $R^*_{40}$, $R^{}_{40}$ and $R^{*}_{40}$ independently represent a hydrogen atom, a straight chain or branched $C_{1-8}$ alkyl group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. Even more preferably, $R_{40}$, $R^*_{40}$, $R^{}_{40}$ and $R^{*}_{40}$ independently represent a hydrogen atom, a straight chain or branched $C_{1-4}$ alkyl group which may be substituted by a cyclohexyl group or a phenyl group, or a cyclohexyl group which may be substituted by a $C_{1-4}$ alkyl group. Most preferably, $R_{40}$, $R^*_{40}$, $R^{}_{40}$ and $R^{*}_{40}$ independently represent a hydrogen atom or a straight chain or branched $C_{1-4}$ alkyl group.

Preferably, in formula (B), $R_{41}$ and $R^*_{41}$ independently represent a hydrogen atom, a straight chain or branched $C_{1-16}$ alkyl group or $C_{2-16}$ alkenyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M, a $C_{3-6}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M, a $C_{6-14}$ aryl or $C_{3-14}$ heteroaryl group which may be substituted by —COOM, —PO$_3$M, —O—PO$_3$M$_2$ or —SO$_3$M. More preferably, $R_{41}$ and $R^*_{41}$ independently represent a hydrogen atom, a straight chain or branched $C_{1-10}$ alkyl or $C_{2-10}$ alkenyl group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. Even more preferably, $R_{41}$ and $R^*_{41}$ independently represent is a hydrogen atom, a straight chain or branched $C_{1-10}$ alkyl group or $C_{2-10}$ alkenyl group which may be substituted by a cyclohexyl group or a phenyl group, or a cyclohexyl group which may be substituted by a $C_{1-4}$ alkyl group. Yet even more preferably, $R_{41}$ and $R^*_{41}$ represent an unsubstituted $C_{1-10}$ alkyl group or $C_{2-10}$ alkenyl group, still even more preferably an unsubstituted $C_{2-6}$ alkyl group or $C_{3-6}$ alkenyl group, and most preferably an ethyl group or an allyl group.

Particular preferred mono- or bis- or (meth)acrylamides and poly[(meth) acrylamides] of formulae (A), (B) and (C) have the following structural formulae:

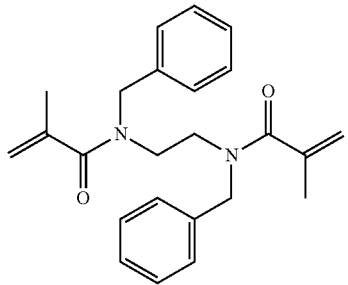
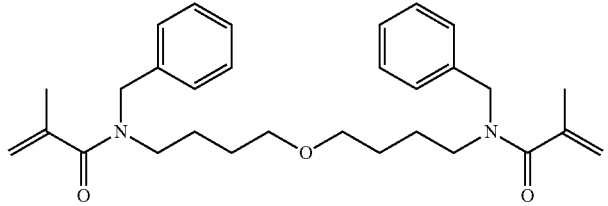
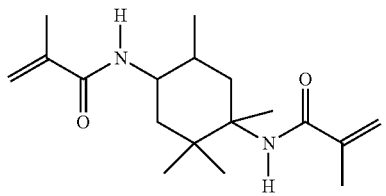
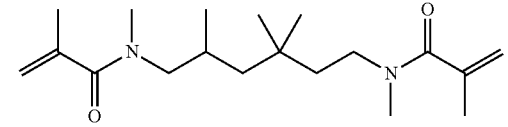
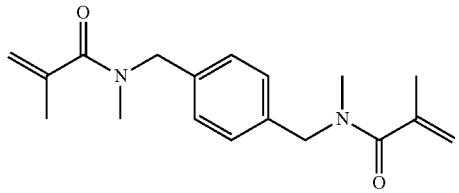
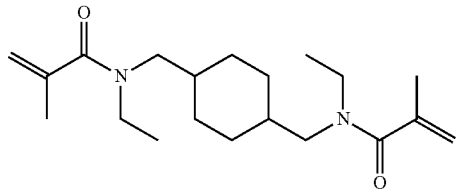

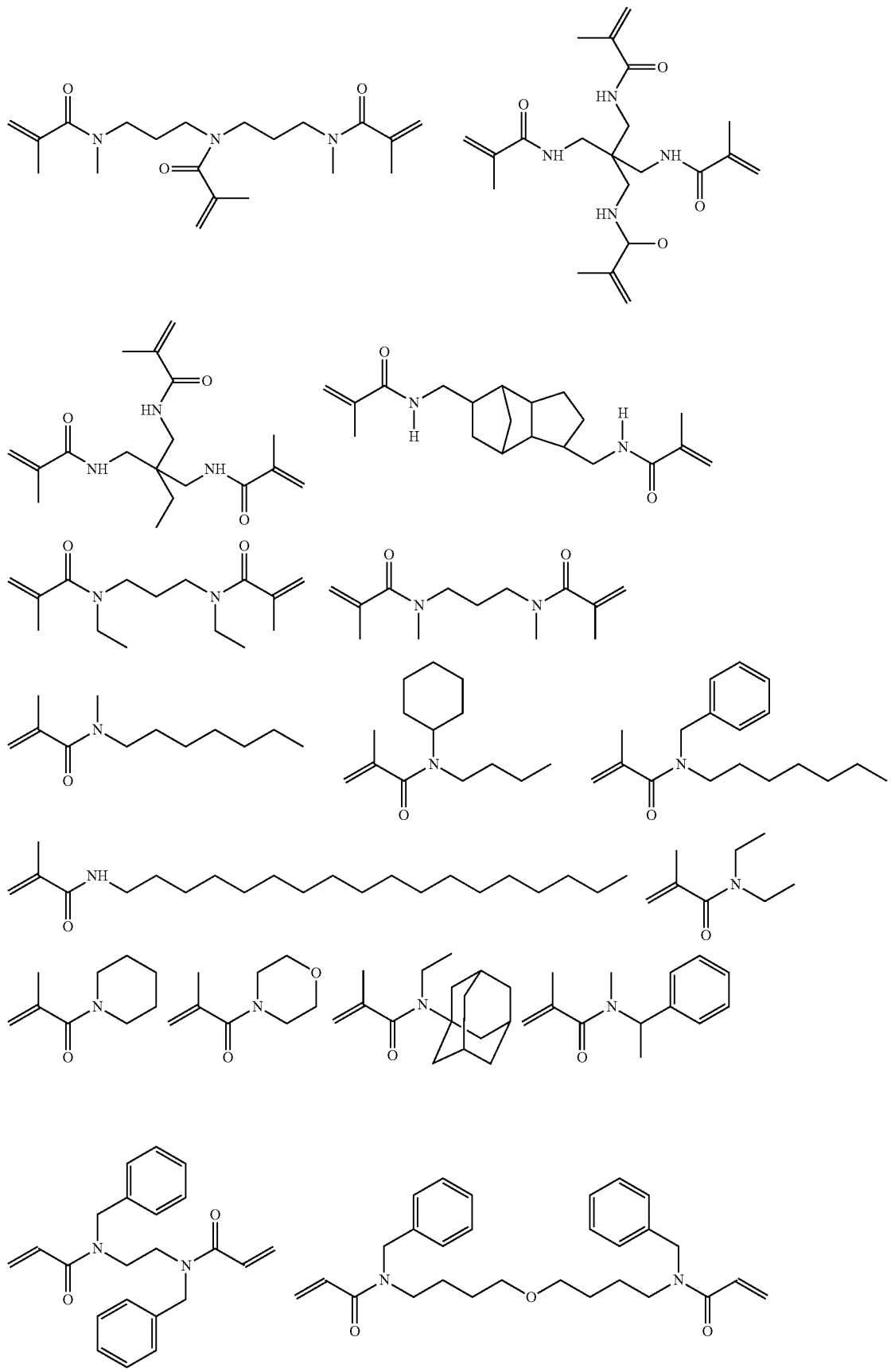

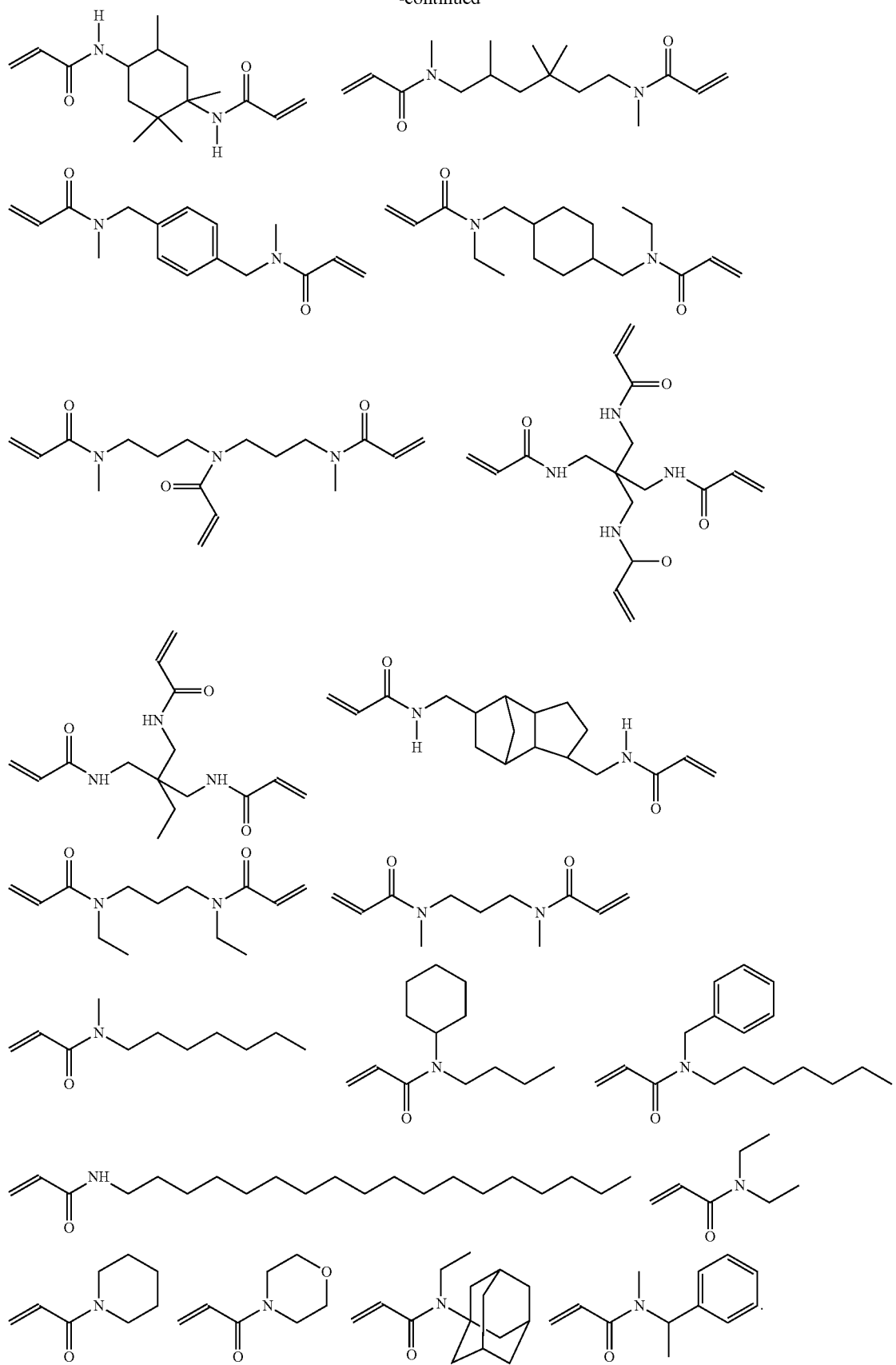

Most preferred is the bis-(meth)acrylamide N,N'-diethyl-1,3-bisacrylamido-propan (BADEP) having the structural formula

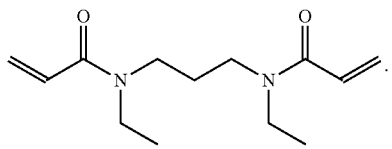 [SMILES: C=CC(=O)N(CC)CCCN(CC)C(=O)C=C]

Other suitable examples of polymerizable compounds having a polymerizable double bond are isopropenyl oxazoline, vinyl azalactone, vinyl pyrrolidone, styrene, divinylbenzene, urethane acrylates or methacrylates, epoxy acrylates or methacrylates and polyol acrylates or methacrylates.

A (meth)acrylate compound may be selected from the group of methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, diglycidyl methacrylate of bis-phenol A ("BisGMA"), di-mono- or polyethoxydyl methacrylate of bis-phenol A ("ethoxyBisGMA"), 11,14-dioxa-2,9-diazaheptadec-16-enoicacid, 4,4,6,16 (or 4,6,6,16)-tetramethyl-10,15-dioxo-,2-[(2-methyl-1-oxo-2-propen-1-yl)oxy]ethyl ester (UDMA), glycerol mono- and di-acrylate, glycerol mono- and dimethacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxyethyl hexamethylene dicarbamate, di-2-methacryloyloxyethyl trimethylhexamethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcydohexane dicarbamate, methylene-bis-2-methacryloxyethyl-4-cyclohexyl carbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]

propane, and 2,2'-bis[3(4-phenoxy)-2-hydroxypropane-1-acryalte]propane, may be mentioned. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates.

It is preferred to select polymerizable compounds having a polymerizable double bond with the proviso that they do not contain ester groups, or at least only ester groups which do not significantly hydrolyze in aqueous media at pH 3 at room temperature within one month. Thereby, an advantageous stability of an acidic dental composition, that is a composition having a pH of less than 7, in terms of shelf-life stability of the uncured dental composition as well as stability after curing in the mouth of a patient is ensured. Therefore, particularly preferred are polymerizable compounds having a polymerizable double bond which do not comprise an ester group. That is, for acidic dental compositions, (meth)acrylates are preferably excluded.

It is preferred that at least one of the polymerizable compounds having at least one polymerizable double bond has an acidic group. This acidic group is preferably selected from a carboxylic acid group, a sulfonic acid ester group, a phosphonic acid ester group and a phosphoric acid ester group.

Phosphoric acid ester group containing polymerizable compounds having at least one polymerizable double bond preferably have the following formula (D):

(D)

wherein the moieties Y independent from each other represent a hydrogen atom or a moiety of the following formulae (Y*), (Y) or (Y*):

(Y*)

-continued

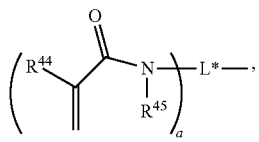
(Y**)

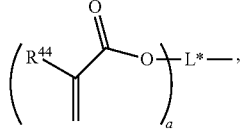
(Y***)

wherein

Z, is COOR$^\alpha$, COSR$^\beta$, CON(R$^\alpha$)$_2$, CONR$^\alpha$ R$^\beta$, or CONHR$^\alpha$, wherein R$^\alpha$ and R$^\beta$ independently represent a hydrogen atom, a C$_{1-18}$ alkyl group optionally substituted by a C$_{3-8}$ cycloalkyl group, an optionally substituted C$_{3-8}$ cycloalkyl group, an optionally substituted C$_{4-18}$ aryl or heteroaryl group, an optionally substituted C$_{5-18}$ alkylaryl or alkylheteroaryl group, or an optionally substituted C$_{7-30}$ aralkyl group, whereby two R$^\alpha$ residues may form together with the adjacent nitrogen atom to which they are bound a 5- to 7-membered heterocyclic ring which may contain further nitrogen atoms or an oxygen atoms, and whereby the optionally substituted groups may be substituted by 1 to 5 C$_{1-5}$ alkyl group(s);

R$^{44}$ and R$^{45}$ independently represent a hydrogen atom, an optionally substituted C$_{1-18}$ alkyl group, an optionally substituted C$_{3-18}$ cycloalkyl group, an optionally substituted C$_{5-18}$ aryl or heteroaryl group, an optionally substituted C$_{5-18}$ alkylaryl or alkylheteroaryl group, an optionally substituted C$_{7-30}$ aralkyl group, whereby the optionally substituted groups may be substituted by 1 to 5 C$_{1-5}$ alkyl group(s);

L' represents an (a+b)-valent organic residue (whereby b is 1 when Y in formula (D) is within the round brackets) containing 2 to 45 carbon atoms and optionally heteroatoms such as oxygen, nitrogen and sulfur atoms, the carbon atoms including a+b carbon atoms selected from primary and secondary aliphatic carbon atoms, secondary alicyclic carbon atoms, and aromatic carbon atoms, each of the a+b carbon atoms linking a phosphate or a moiety of any one of formula (Y*), (Y) and (Y*); a is an integer of from 1 to 10, preferably 1 to 5; b is an integer of from 1 to 10, preferably 1 to 5; provided that at least one Y is not hydrogen. The preparation of such compounds wherein Y=Y* is known from EP-A 1 548 021.

Furthermore, the polymerizable monomer having one or more acidic groups may be selected from:
1) phosphonic acid group containing polymerizable acidic compounds of the following formula (E):

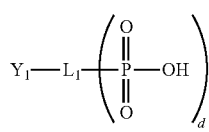
(E)

wherein
the moiety Y$_1$ represents a moiety of the following formulae (Y$_1$*), (Y$_1$) or (Y$_1$*):

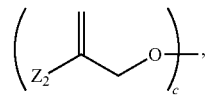
(Y$_1$*)

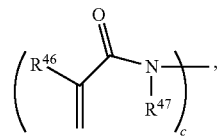
(Y$_1$**)

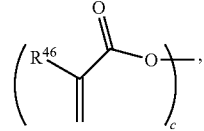
(Y$_1$***)

Z$_2$ independently has the same meaning as defined for Z$_1$;
R$^{46}$ and R$^{47}$ independently have the same meaning as defined for R$^{44}$ and R$^{45}$;
L$_1$ represents a (c+d) valent organic residue containing 2 to 45 carbon atoms and optionally heteroatoms such as oxygen, nitrogen and sulfur, the carbon atoms including c+d carbon atoms selected from primary and secondary aliphatic carbon atoms, secondary alicyclic carbon atoms, and aromatic carbon atoms, each of the c+d carbon atoms linking a phosphonate or a moiety of any one of formula (Y$_1$*), (Y$_1$) and (Y$_1$*); and c and d independently represent integers of from 1 to 10; and/or 2) sulfonic acid group containing polymerizable acidic compounds of the following formula (F):

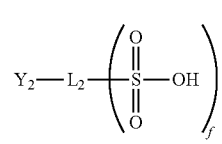
(F)

wherein
the moiety Y$_2$ represents a moiety of the following formulae (Y$_2$*), (Y$_2$) or (Y$_2$*):

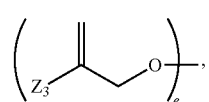
(Y$_2$*)

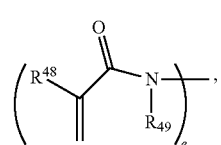
(Y$_2$**)

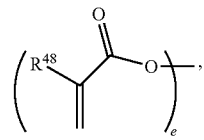
(Y$_2$***)

$Z_3$ independently has the same meaning as defined for $Z_1$;

$R^{48}$ and $R^{49}$ independently have the same meaning as defined for $R^{44}$ and $R^{45}$;

$L_2$ represents an (e+f) valent organic residue containing 2 to 45 carbon atoms and optionally heteroatoms such as oxygen, nitrogen and sulfur atoms, the carbon atoms including e+f carbon atoms selected from primary and secondary aliphatic carbon atoms, secondary alicyclic carbon atoms, and aromatic carbon atoms, each of the e+f carbon atoms linking a sulphonate or a moiety of any one of formula $(Y_2^*)$, $(Y_2^{})$ and $(Y_2^{*})$; and e and f independently represent an integer of from 1 to 10.

It is preferred to select compounds of formula (D), (E) and (F) with the proviso that they do not contain ester groups, or at least only ester groups which do not significantly hydrolyze in aqueous media at pH 3 at room temperature within one month, such as the phosphoric acid ester group of compounds of formula (D). Thereby, an advantageous stability of an acidic dental composition, that is a composition having a pH of less than 7, in terms of shelf-life stability of the uncured dental composition as well as stability after curing in the mouth of a patient is ensured. Therefore, particularly preferred are compounds of formula (D) excluding the moiety of formula $Y^{***}$ and the moiety of formula $Y^*$ wherein $Z_1$ is $COOR^\alpha$ or $COSR^\beta$, compounds of formula (E) excluding the moiety of formula $Y_1^{***}$ and the moiety of formula $Y_1^*$ wherein $Z_2$ is $COOR^\alpha$ or $COSR^\beta$ as well as compounds of formula (F) excluding the moiety of formula $Y_2^{***}$ and the moiety of formula $Y_2^*$ wherein $Z_3$ is $COOR^\alpha$ or $COSR^\beta$.

From the phosphoric acid ester group containing polymerizable compound having at least one polymerizable double bond, compounds of formula (D') characterized by one of the following formulae are particularly preferred:

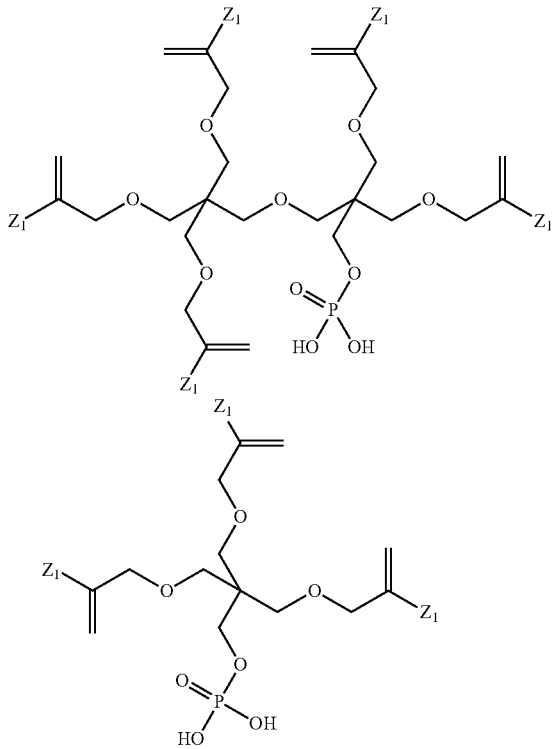
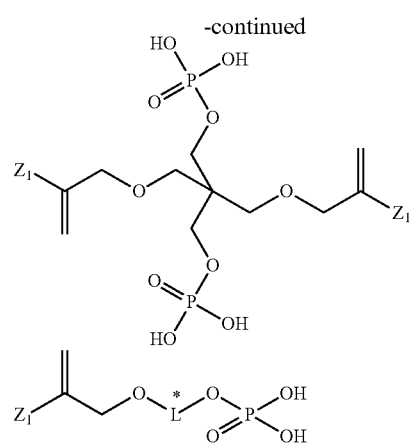

wherein $Z_1$ is defined as above, and $L^*$ is an optionally substituted alkylene group. More preferably, $Z_1$ is methyl, and $L^*$ is a $C_4$ to $C_{16}$ alkylene group. Even more preferably, $L^*$ is a $C_8$ to $C_{12}$ alkylene group.

From the sulfonic acid group containing polymerizable compound having at least one polymerizable double bond, compounds of formula (F') characterized by one of the following formulae are particularly preferred:

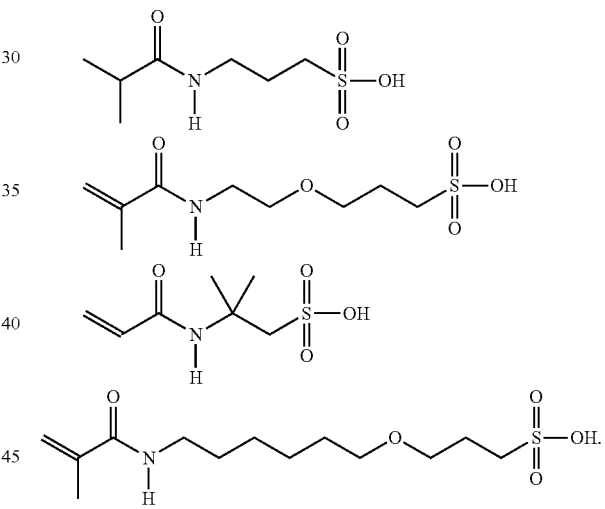

In a particularly preferred embodiment, according to (b), the dental composition according to the present invention contains one or more polymerizable compounds having at least one (meth)acryl moiety and optionally one or more polymerizable compounds having a polymerizable double bond and an acidic group, more preferably one or more polymerizable compounds of formula (A), (B) or (C) described above and optionally one or more polymerizable compounds of formula (D), (E) or (F) described above.

Carboxylic acid group containing polymerizable compounds having at least one polymerizable double bond may be selected e.g. from acrylic acid and methacrylic acid.

Preferably, the one or more compounds having a polymerizable double bond each contain one or two radical-polymerizable groups.

It is preferable that a blending ratio of the one or more polymerizable compounds having a polymerizable double bond to the entire dental composition is 5 to 80% by weight. More preferably, the blending ratio is 10 to 60% by weight.

Further Components

Optionally, the dental compositions of the present invention may further comprise a stabilizer, a solvent and/or a particulate filler.

The dental composition may comprise one or more stabilizer(s).

The term "stabilizer" as used herein means any compound capable of preventing polymerizable compounds contained in the dental composition from spontaneous polymerization during storage. However, the stabilizer does not disturb or prevent intended polymerisation curing of the dental composition during application.

For example, the stabilizer may be a conventional stabilizer selected from the group consisting of hydroquinone, hydroquinone monomethylether, tert-butyl-hydroquinone, tert-butylhydroxyanisol, propyl gallate and 2,6-di-tert-butyl-p-cresol. From these conventional stabilizers, 2,6-di-tert-butyl-p-cresol is preferred.

Preferably, the stabilizer is a compound of the following formula (XVI) and/or (XVII):

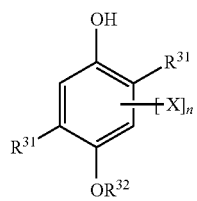

(XVI)

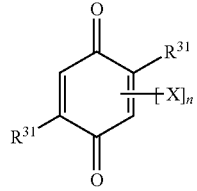

(XVII)

wherein
the $R^{31}$, which may be the same or different, independently represent a branched $C_{3-8}$ alkyl group or alkenyl or a $C_{3-8}$ cycloalkyl or cycloalkenyl group,
$R^{32}$ represents a hydrogen atom, $C_{1-6}$ alkyl or $C_{2-6}$ alkenyl group, or a $C_{1-6}$ fluoroalkyl or $C_{2-6}$ fluoroalkenyl group,
X represents a group selected from a $C_{1-8}$ alkyl group or a $C_{3-8}$ cycloalkyl group, and
n is 0, 1 or 2.

The class of stabilizers of formula (XVI) and/or (XVII) may provide for full or at least substantial avoidance of discoloration upon storage and/or during photocuring. In particular, this class of stabilizers provides for a surprising stabilizing effect in an acidic aqueous mixture so that a dental composition having a pH of less than 7 may be provided which has no or substantially no discoloration upon storage and an excellent storage stability due to an improved resistance against premature polymerization.

More preferably, the stabilizer is a compound of formula (XVI) and/or (XVII) wherein the $R^{31}$, which may be the same or different, independently represent a branched $C_{3-8}$ alkyl group or a $C_{3-8}$ cycloalkyl group, and $R^{32}$ represents a hydrogen atom, $C_{1-6}$ alkyl group or a $C_{1-6}$ fluoroalkyl group, and n is 0 or 1. Even more preferably, the stabilizer is a compound of formula (XVI) and/or (XVII) wherein the $R^{31}$, which may be the same or different, independently represent a branched $C_{3-8}$ alkyl group and $R^{32}$ represents a hydrogen atom or a $C_{1-6}$ alkyl group, and n is 0. Most preferably, the stabilizer is a compound of the following formulae (XVIa), (XVIb) or (XVIIa):

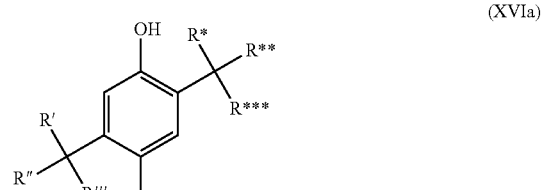

(XVIa)

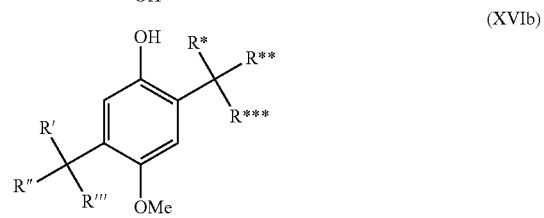

(XVIb)

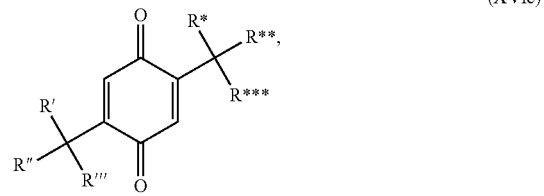

(XVIc)

wherein R', R", R''', R*, R and R*, which may be the same or different, independently represent a methyl or an ethyl group. It is particularly preferred that the stabilizer of formulae (XVIa), (XVIb) or (XVIIa) is a compound of the following formulae:

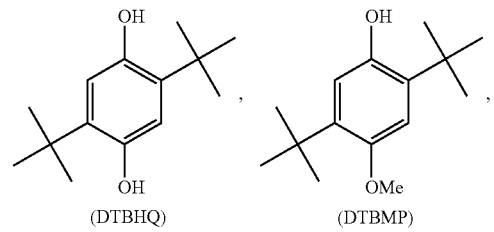

(DTBHQ)    (DTBMP)

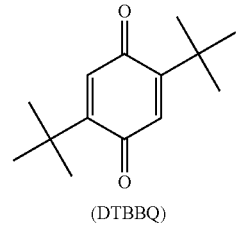

(DTBBQ)

preferably DTBHQ.

The stabilizer DTBHQ is particularly preferred, since from experimental testings it appears that this stabilizer provides the best results in view of the discoloration problematic, i.e. there is no or almost no discoloration of the dental composition upon storage at 50° C. for 30 days.

Discoloration upon storage and/or during photocuring may be determined according to ISO 7491:2000(en).

The dental composition according to the invention contains the stabilizer in an amount of 0.001 to 1 percent by weight, preferably 0.005 to 0.8 percent by weight based on the total weight of the composition. When the amount of the stabilizer is below the above indicated lower limit of 0.001, then storage stability of the dental composition might be insufficient, since the amount of stabilizer is too small to provide a stabilizing effect. However, when the amount of stabilizer is above the maximum threshold of 1 percent by weight, then the applicability of the dental composition might be negatively affected, since higher amounts of stabilizer may disturb or even substantially prevent intended polymerisation curing of the dental composition during application.

Suitable solvents may be selected from water, alcohols such as methanol, ethanol, propanol (n-, i-), butanol (n-, iso-, tert.-), ketones such as acetone or the like.

The dental composition of the present invention may preferably comprise 5 to 75 percent by weight based on the total weight of the composition of a solvent.

Suitable particulate fillers may be selected from fillers currently used in dental compositions. The filler should be finely divided and preferably has a maximum particle diameter less than about 100 µm and an average particle diameter less than about 10 µm. The filler may have a unimodal or polymodal (e.g., bimodal) particle size distribution.

The filler can be an inorganic material. It can also be a crosslinked organic material that is insoluble in the polymerizable resin, and is optionally filled with inorganic filler. The filler can be radioopaque. Examples of suitable particulate inorganic fillers are naturally-occurring or synthetic materials such as quartz, nitrides such as silicon nitride, glasses derived from, for example Ce, Sb, Sn, Zr, Sr, Ba and Al, colloidal silica, feldspar, borosilicate glass, kaolin, talc, titania, and zinc glass, and submicron silica particles such as pyrogenic silicas. Examples of suitable non-reactive organic filler particles include filled or unfilled pulverized polycarbonates or polyepoxides. Preferably the surface of the filler particles is treated with a coupling agent in order to enhance the bond between the filler and the matrix. The use of suitable coupling agents include gamma-methacryloxypropyltrimethoxysilane, gamma-mercaptopropyltriethoxysilane, gamma-aminopropyltrimethoxysilane, and the like.

The particulate filler may also be a filler obtainable by a process for the preparation of composite filler particles, comprising:

(a) coating a particulate filler having a median particle size (D50) of from 1 to 1200 nm with a coating composition containing a film-forming agent forming a coating layer on the surface of the particulate filler, said coating layer displaying reactive groups on the surface of the coating layer, said reactive groups being selected from addition polymerizable groups and step-growth polymerizable groups, thereby forming a coated particulate filler; subsequently or concurrently (b) agglomerating the coated particulate filler, optionally in the presence of a further crosslinking agent and optionally in the presence of a further particulate filler not displaying reactive groups, for providing a granulation of the coated particulate filler wherein the granulation contains the coated particulate filler particles and the optional further particulate filler particles separated from and connected to each other by at least one coating layer, whereby the at least one coating layer may be crosslinked by crosslinking groups obtained by reacting the reactive groups and optionally a further crosslinking agent;

(c) optionally milling, classifying and/or sieving the granulation of the coated particulate filler; and (d) optionally further crosslinking the granulation of the coated particulate filler; for providing composite filler particles having a median particle size (D50) of from 1 to 70 µm, wherein reactive groups are transformed into crosslinking groups obtained by reacting reactive groups and optionally a further crosslinking agent, and wherein the particulate filler is the main component by volume of the composite filler particles as further described in EP-A 2 604 247.

The dental composition of the present invention may preferably comprise 0.1 to 85 percent by weight based on the total weight of the composition of particulate filler.

The dental compositions of the present invention may further contain preservatives, pigments, free radical scavengers, reactive and nonreactive diluents, coupling agents to enhance reactivity of fillers, rheology modifiers, and surfactants.

Suitable preservatives may be selected from reducing agents such as vitamin C, inorganic sulfides and polysulfides and the like.

Particular Preferred Embodiment

According to a particularly preferred embodiment, the dental composition according to the invention comprises
(a) an initiator system comprising
(a1) a sensitizer compound of the following formula (I'):

$$X'\!-\!R' \qquad (I)$$

wherein
X' is a group of the following formula (II'):

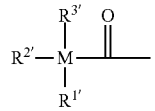

(II')

wherein
M is Si or Ge, preferably Si;
$R^{1'}$ and $R^{2'}$ are independently selected from the group consisting of a straight chain or branched $C_{1-4}$ alkyl group, and a phenyl or benzoyl group optionally substituted with one substituent selected from the group consisting of a halogen atom, a nitro group, a $C_{1-4}$ alkoxy group and a —$NR^xR^y$ group wherein $R^x$ and $R^y$ independently from each other represent a $C_{1-4}$ alkyl group, and
$R^{3'}$ is a straight chain or branched $C_{1-4}$ alkyl group, or a phenyl group optionally substituted with one substituent selected from the group consisting of a halogen atom, a nitro group, a $C_{1-4}$ alkoxy group and a —$NR^xR^y$ group wherein $R^x$ and $R^y$ independently from each other represent a $C_{1-4}$ alkyl group,
R' (i) has the same meaning as X', whereby the sensitizer compound of formula (I') may be symmetrical or unsymmetrical; or
(ii) a group of the following formula (III'):

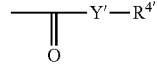

(III')

wherein
Y' represents a single bond, an oxygen atom or a group NR", wherein R" has the same meaning as $R^{1'}$ and is selected independently therefrom;
$R^{4'}$ has the same meaning as $R^{3'}$ and is selected independently therefrom, or represents a trihydrocarbylsilyl group, a mono(hydrocarbylcarbonyl)dihydrocarbylsilyl group or a bi(hydrocarbylcarbonyl)monohydrocarbylsilyl)group, wherein the hydrocarbyl and hydrocarbylcarbonyl groups have the same meaning as $R^{1'}$, $R^{2'}$ and $R^{3'}$ and is selected independently therefrom, or (iii) when M is Si, R may be a substituted or unsubstituted hydrocarbyl group having the same meaning as defined for $R^{3'}$ and being selected independently therefrom;

preferably the compound of formula (I) is selected from the group consisting of tert-butyl (tert-butyldimethylsilyl)glyoxylate) (DKSi), benzoyldiphenylmethylsilane (BDMSi), benzoyltrimethylsilane (BTMSi), 4-chlorophenyl(trimethylsilyl)methanone, 3-chlorophenyl(trimethylsilyl)-methanone, 4-nitrophenyl(trimethylsilyl)methanone, 3-nitrophenyl-(trimethylsilyl) methanone, N, N-dimethylamino (tert-butyldimethylsilyl)glyoxamide, N,N-dimethylamino (tert-butyldimethylgermyl)glyoxamide and tert-butyl (trimethylgermyl)glyoxylate (TKGe); most preferably from the group consisting of tert-butyl (tert-butyldimethylsilyl)-glyoxylate) (DKSi), benzoyldiphenylmethylsilane (BDMSi), benzoyltrimethylsilane (BTMSi), tert-butyl (tert-butyldimethylsilyl)-glyoxylate) and tert-butyl (trimethylgermyl)glyoxylate (TKGe); and (a2) a coinitiator compound of the following formula (IV'):

X'-L'-X" (IV')

wherein
X' represents a group of the following formula (V') or (VI'):

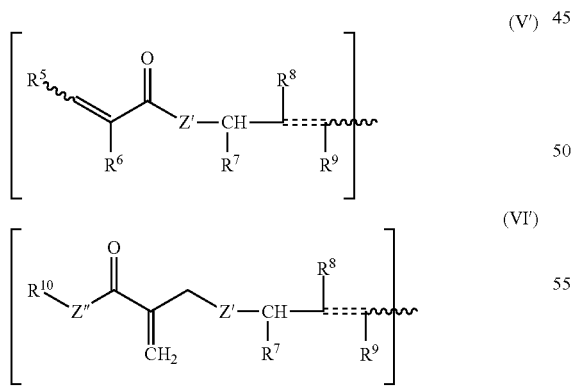

wherein
the dotted lines represent
  a double bond or a triple bond, whereby in case a triple bond is present, $R^8$ and $R^9$ are absent, preferably a double bond;
the jagged line(s) indicate(s) that formula (V') and (VI') include any (E) or (Z) isomer, Z' and Z", independently represent an oxygen atom or >N—R°,
wherein
R° is a group of the following formula (VII'):

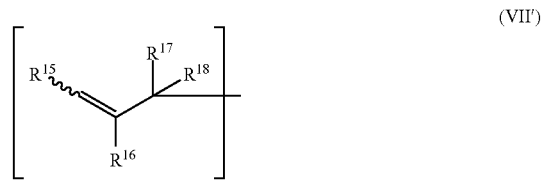

wherein
the jagged line indicates that formula (VII') includes any (E) or (Z) isomer,
$R^{15}$ represents a hydrogen atom or a straight-chain $C_{1-4}$ alkyl or $C_{2-4}$ alkenyl group or a branched or cyclic $C_{3-6}$ alkyl or alkenyl group, preferably a hydrogen atom or a straight-chain $C_{1-4}$ or branched $C_{3-6}$ alkyl group,
$R^{16}$ represents a hydrogen atom;
$R^{17}$ and $R^{18}$
which may be the same or different, independently represent a hydrogen atom or a straight-chain $C_{1-4}$ alkyl or $C_{2-4}$ alkenyl group or a branched or cyclic $C_{3-6}$ alkyl or alkenyl group, preferably a hydrogen atom or a straight-chain $C_{1-4}$ or branched $C_{3-6}$ alkyl group, or $R^{17}$ and $R^{18}$ represent together an oxygen atom forming a carbonyl group together with the adjacent carbon atom;
$R^5$ represents a hydrogen atom;
$R^6$ represents a hydrogen atom or a straight-chain $C_{1-4}$ or branched $C_{3-6}$ alkyl group, which group may be substituted by at least one moiety selected from the group consisting of a hydroxyl group, a $C_{1-6}$ alkoxy group and an acidic group, preferably by a $C_{1-6}$ alkoxy group;
$R^7$ represents a hydrogen atom or a straight-chain $C_{1-4}$ alkyl or $C_{2-4}$ alkenyl group or a branched or cyclic $C_{3-6}$ alkyl or alkenyl group, preferably a hydrogen atom or a straight-chain $C_{1-4}$ or branched $C_{3-6}$ alkyl group;
$R^8$ and $R^9$,
which may be the same or different, independently represent a hydrogen atom or a straight-chain $C_{1-4}$ or branched $C_{3-6}$ alkyl group, preferably $R^4$ and $R^5$ respectively represent a hydrogen atom;
$R^{10}$ represents a hydrogen atom or a straight-chain $C_{1-4}$ alkyl or $C_{2-4}$ alkenyl group or a branched or cyclic $C_{3-6}$ alkyl or alkenyl group, preferably a straight-chain $C_{1-4}$ or branched or cyclic $C_{3-6}$ alkyl group, which group may be substituted by a $C_{1-6}$ alkoxy group;
X" represents a moiety of the following formula (VIII') or (IX'):

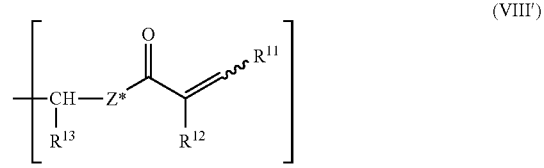

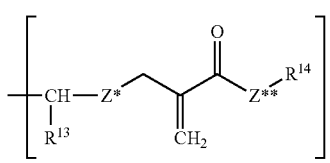

wherein
the jagged line indicates that formula (VIII') includes any (E) or (Z) isomer,
Z* and Z**, which may be the same or different, independently represent an oxygen atom or >N—R˙, wherein
R˙ has the same meaning as defined above for R°;
$R^{11}$ is a hydrogen atom;
$R^{12}$ represents a hydrogen atom or a straight-chain $C_{1-4}$ or branched $C_{3-6}$ alkyl group, which group may be substituted by at least one moiety selected from the group consisting of a hydroxyl group, a thiol group, a $C_{1-6}$ alkoxy group and an acidic group, preferably by a $C_{1-6}$ alkoxy group;
$R^{13}$ represents a hydrogen atom or a straight-chain $C_{1-4}$ alkyl or $C_{2-4}$ alkenyl group or a branched or cyclic $C_{3-6}$ alkyl or alkenyl group, preferably a hydrogen atom or a straight-chain $C_1$-4 or branched $C_{3-6}$ alkyl group;
$R^{14}$ represents a hydrogen atom or a straight-chain $C_{1-4}$ alkyl or $C_{2-4}$ alkenyl group or a branched or cyclic $C_{3-6}$ alkyl or alkenyl group, preferably a hydrogen atom or a straight-chain $C_{1-4}$ or branched $C_{3-6}$ alkyl group;
whereby $R^8$ and R°, and/or $R^{15}$ and $R^{17}$ may represent together an alkylene or alkenylene group forming together with the bridging atoms to which they are linked a 3- to 6-membered saturated or unsaturated ring;
whereby $R^{13}$ and R˙, and/or $R^{15}$ and $R^{17}$, may represent together an alkylene or alkenylene group forming together with the bridging atoms to which they are linked a 3- to 6-membered saturated or unsaturated ring; and
whereby $R^7$ and $R^{13}$ may represent an alkylene or alkenylene group forming together with the bridging atoms to which they are linked a 4- to 6-membered unsaturated ring; and
L˙ which may be present or absent, represents, when present, a divalent linker group of formula (X')

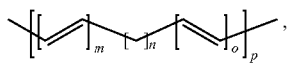

wherein m is 0, n is 0 or 1 and o is 0 or 1, and p is 1, and when L˙ is absent, X' and X" are bonded directly by a single bond;
preferably, L˙ is a single bond;
wherein if X' represents a group of formula (V), X" is a group of formula (VIII), and if X' represents a group of formula (VI), X" is a group of formula (IX), and (a3) optionally a iodonium salt, preferably a diaryl iodonium salt, more preferably a diaryl iodonium hexafluorophosphate, even more preferably a hexafluorophosphate salt of DTPI, DPI, Me2-DPI and/or 4-methylphenyl[4-(2-methylpropyl)phenyl] iodonium, most preferably DTPI hexafluorophosphate.

The present invention further relates to an initiator system consisting essentially of (a1) a sensitizer compound of the formula (I) as described above, and (a2) a coinitiator wherein a C—H bond dissociation energy is less than 95 Kcal/mol, preferably less than 90 Kcal/mol, more preferably less than 84 Kcal/mol, still more preferably less than 82 Kcal/mol, most preferably less than 80 Kcal/mol. It is preferred that the coinitiator is a compound of formula (IV) as described above.

The initiator system may be used for the preparation of a dental composition, preferably of a dental composition according to the invention as described above.

The invention will now be further illustrated by the following Examples.

Example 1: Preparation of Acylsilanes

General Procedure for the Preparation of Acylsilanes.[1]

A 10 mL screw-capped glass tube with a magnetic stir bar was charged with 0.054 g dichloro($\eta^3$-allyl)dipalladium(II) (0.3 mmol), 0.1 g Triethylphosphit (0.6 mmol) under $N_2$. Hexametyldisilane (0.96 g, 6.6 mmol) was added, and the mixture was stirred for 5 min at room temperature. After that, 6 mmol benzoylchloride was added slowly to the yellow solution. The reaction mixture was heated at 110° C. for 2.5 h. After cooling to room temperature, the reaction mixture was purified by column chromatography using the indicated eluent, without any preceding purification step.

[1] Yamamoto, K.; Suzuki, S.; Tsuji, J. Tetrahedron Lett. 1980, 21, 1653.

For example, phenyl(trimethylsilyl)methanone was prepared as follows:

The title compound was prepared according to the general procedure using 0.84 g benzoylchloride (6 mmol), 0.054 g dichloro($\eta^3$-allyl)dipalladium(II) (0.3 mmol), 0.1 g Triethylphosphit (0.6 mmol) and 0.96 g Hexametyldisilane (6.6 mmol). The crude product was purified by column chromatography and received as clear yellow oil.

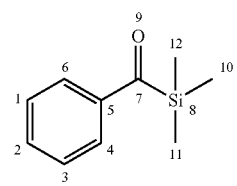

$^1$H-NMR [ppm]: (300 MHz, $CDCl_3$) δ 7.85-7.82 (m, 2H, Pos. 4, 6), δ 7.57-7.44 (m, 4H, Pos. 1, 2, 3), δ 0.38 (s, 9H, Pos. 10, 11, 12)

$^{13}$C-NMR [ppm]: (75 MHz, $CDCl_3$) δ 235.94 (Pos. 7); δ 141.48 (Pos. 5); δ 132.84 (Pos. 2); δ 128.80 (Pos. 4, 6); δ 127.63 (Pos. 1, 3); δ-1.21 (Pos. 10, 11, 12)

The above described general procedure for the preparation of acylsilanes was successfully carried out for the preparation of further acylsilanes, as described in priority application EP EP 15 188 969, namely for 4-chlorophenyl (trimethylsilyl)methanone, 3-chlorophenyl(trimethylsilyl)

methanone, 4-nitrophenyl(trimethylsilyl)methanone and 3-nitrophenyl(trimethylsilyl)methanone.

Example 2: Preparation of Germyglyoxylates

General Procedure for the Preparation of Germyiglyoxylates:

Germylglyoxylates can be synthesized according to the general procedure depicted in Scheme 3.

Specifically, according to this general procedure, a tert-butyl (trimethylgermyl)glyoxylate (TKGe) having the structural formula

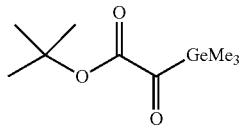

was synthesized.

IR spectrum (BaF$_2$ pellet): glyoxylate peak at 1720 cm$^{-1}$.

Remarkably, this compound exhibits a good light absorption property in the 400-500 nm range with an extinction coefficient of about 120 M$^{-1}$ cm$^{-1}$ at 470 nm.

Examples 3 and 4: Photopolymerisation Testing with Different Photoinitiator Systems Materials Camphor quinone (CQ) was obtained from Aldrich and used as representative Norrish type II system.

Ethyldimethylaminobenzoate (EDB) was obtained from Aldrich.

Bisphenol A-glycidyl methacrylate (BisGMA) and triethyleneglycol dimethacrylate (TEGDMA) were obtained from Sigma-Aldrich and used with the highest purity available.

Di(4-tert-butylphenyl)-iodonium (DTPI) hexafluorophosphate was obtained from Lambsom, trade name Speed-Cure® 938.

N,N'-diallyl-1,4-bisacrylamido-(2E)-but-2-en (BAABE), BisGMA, diethoxydyl methacrylate of bisphenol A (ethoxy-BisGMA), UDMA, a blend of BisGMA/BAABE, ethoxy-BisGMA/BAABE, and BisGMA/TEGDMA was used as benchmark matrix for the initiator system according to the present invention.

(a1) Sensitizer compounds of formula (I):

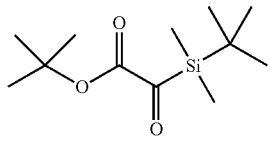 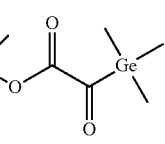

DkSi      TKGe (a2) coinitiator compound of formula (IV):

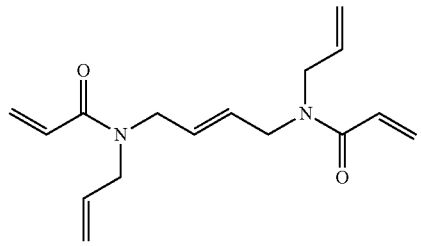

BAABE (a3) iodonium salt

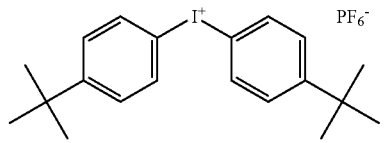

DTPI conventional sensitizer compound for comparison and/or additional coinitiator compounds:

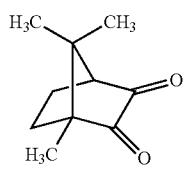

Camphorquinone (CQ)

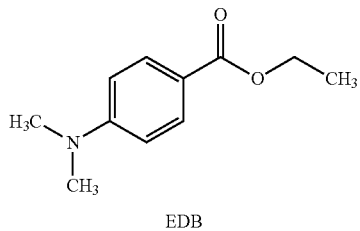

EDB (b) polymerizable compounds having at least one polymerizable double bond:

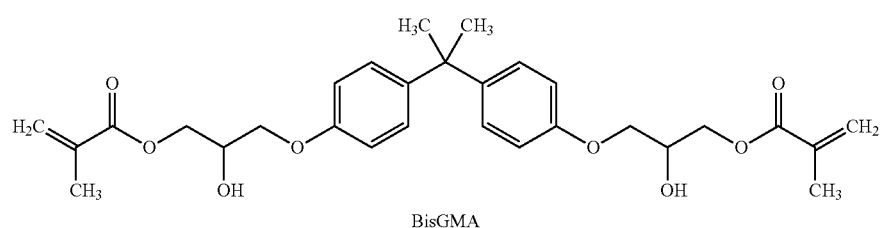

BisGMA

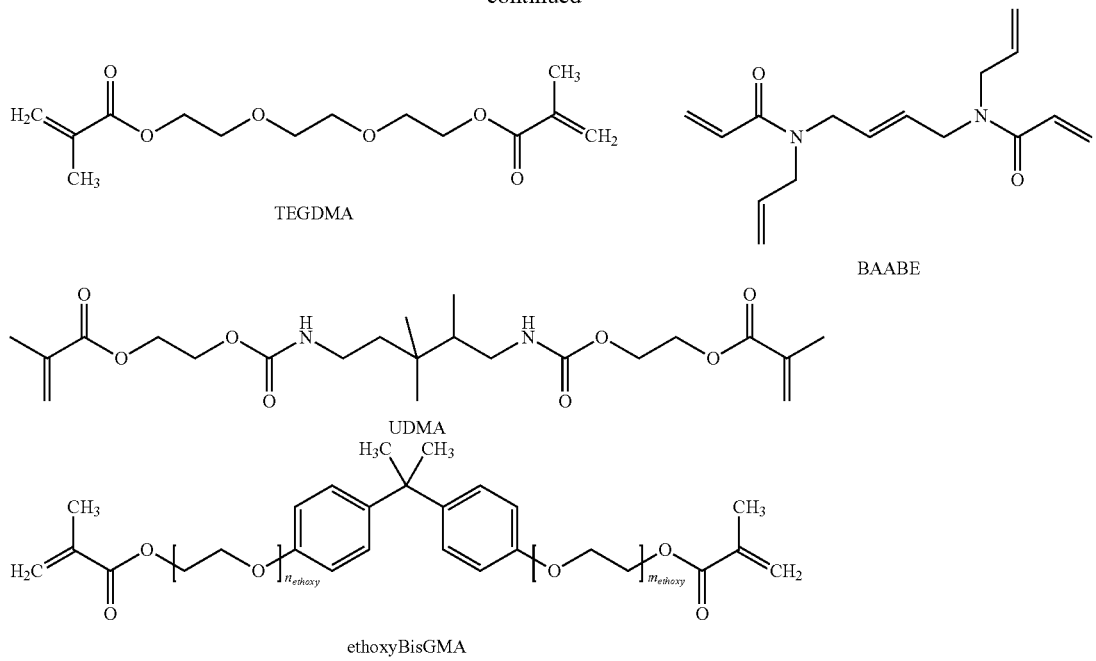

Scheme 9

Chemical structures of compounds applied in the photopolymerisation testings

Compounds of formula (IV) can be readily prepared, as described in the priority application EP 16 170 375 e.g. for N,N'-bisacryloyl-N,N'-bisallyl-2,4-pent-2-endiamine and N,N'-bisacryloyl-N,N'-bispropyl-1,4-but-2-endiamine.

Irradiation Source

For the irradiation of the photocurable samples, blue dental LED centered at 477 nm (SmartLite® Focus from Dentsply) was used. The emission spectrum of this irradiation source is given in FIG. 1. In the photopolymerization profiles of FIGS. 3, 4, 7 to 9 and 12 to 16, the applied surface power density was 300 mW/cm$^{-2}$ at the surface of the irradiated sample.

Photopolymerization Experiments:

For the photopolymerization experiments, the conditions are given in the figure captions, wherein the indication "%" for blends such as BisGMA/BAABE, ethoxyBisGMA/BAABE, and BisGMA/TEGDMA means the blending ratio in mass-%. Furthermore, for the compounds DKSi, TKGe, CQ, DTPI and EDB, the indication "% w/w" means the % by weight of these compounds relative to the total weight of the sample.

The photo-sensitive compositions were deposited on a BaF$_2$ pellet under air (thickness: about 20 μm and 250 μm for thin samples, 1.4 mm for thick samples) for irradiation with blue dental LED centered at 477 nm (SmartLite® Focus).

For the polymerization profiles of FIGS. 3, 4, 7 to 9 and 12 to 16, the evolution of the double bond content during the polymerization of the compounds BAABE, BisGMA, ethoxyBisGMA, TEGDMA, UDMA alone or in combination was continuously followed by real time FTIR spectroscopy (JASCO FTIR 4100) at about 1630 cm$^{-1}$. In the IR spectra of FIG. 5, for BAABE, and FIGS. 10 and 11 for BisGMA/BAABE, the evolution of the double bond content before and after polymerization was followed at about 6122 and 6148 cm$^{-1}$. Furthermore, in the IR spectra of FIG. 6, for BAABE, the content of allylic C—H before and after polymerization was followed at about 3010 and 3080 cm$^{-1}$ (cf. FIG. 6).

Figure 3:
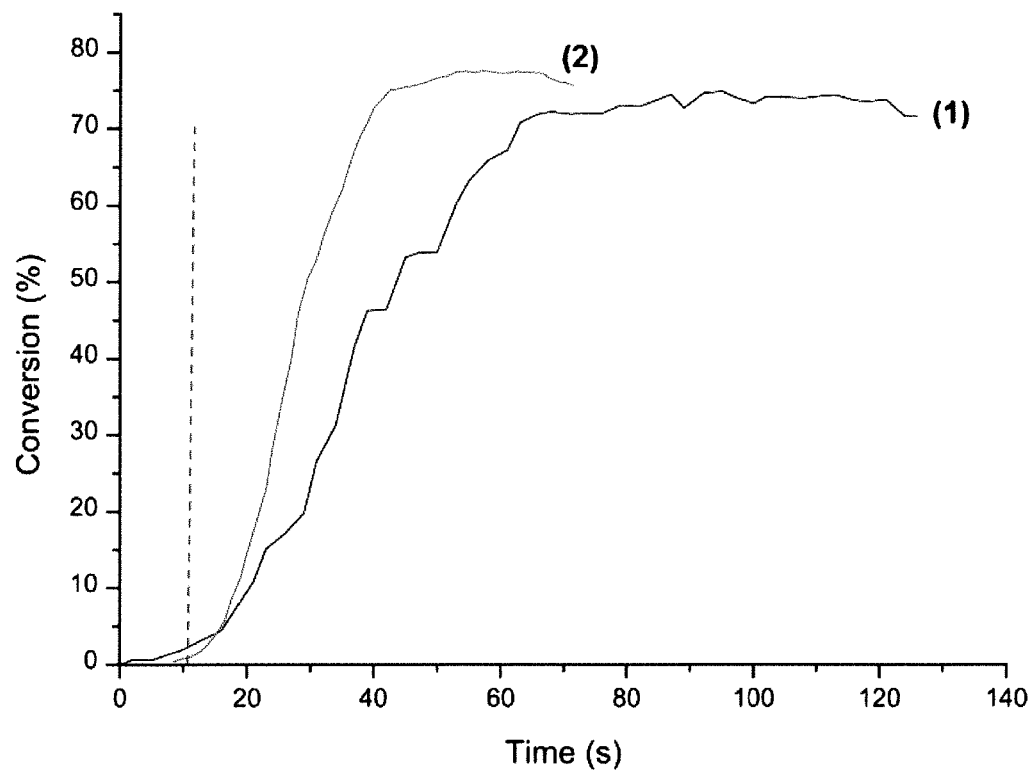
FIG. 3 shows the photopolymerization profile of N,N'-diallyl-1,4-bisacrylamido-(2E)-but-2-en (BAABE) polymerized in samples of 1.4 mm thickness under air upon the exposure to dental LED at 477 nm (SmartLite® Focus) in the presence of the following sensitizers:
  curve (1): Camphor quinone (CQ) 2% w/w; and
  curve (2): Tert-butyl (tert-butyldimethylsilyl)glyoxylate) (DKSi) 2% w/w.
Figure 4:
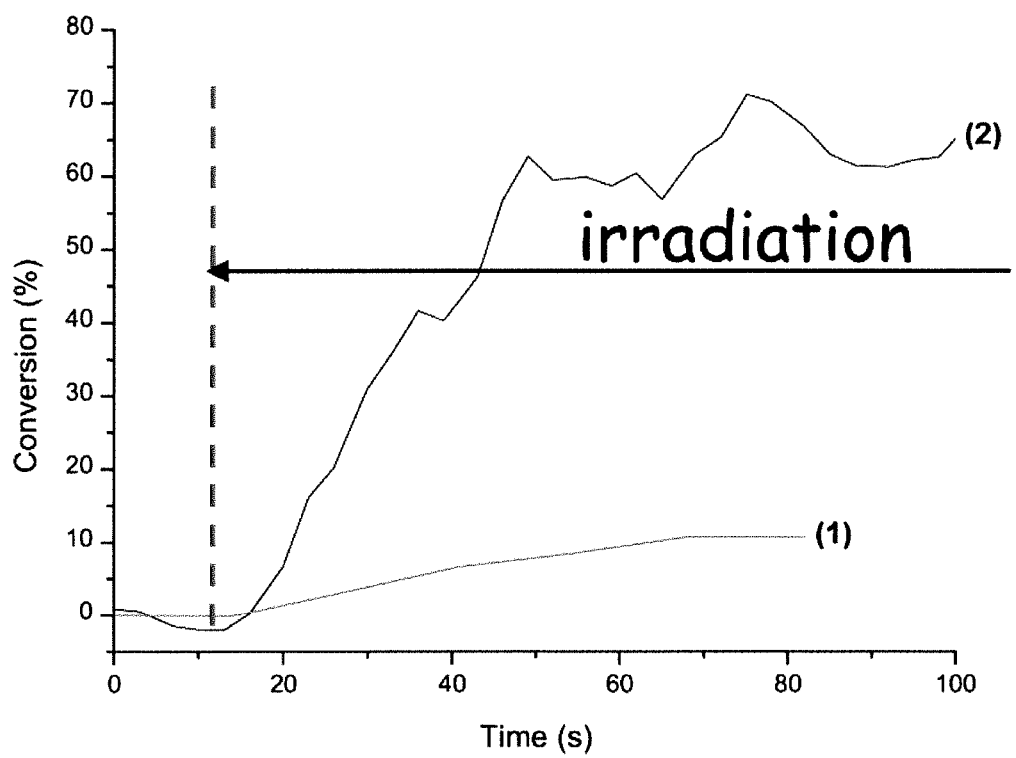
FIG. 4 shows the photopolymerization profile of bisphenol A-glycidyl methacrylate (BisGMA) and triethyleneglycol dimethacrylate (TEGDMA) polymerized in samples of 1.4 mm thickness under air upon the exposure to dental LED at 477 nm (SmartLite® Focus) in the presence of the following sensitizers:
  Curve (1): CQ 1.2% w/w; and
  curve (2): DKSi 1.8% w/w.
Figure 13:
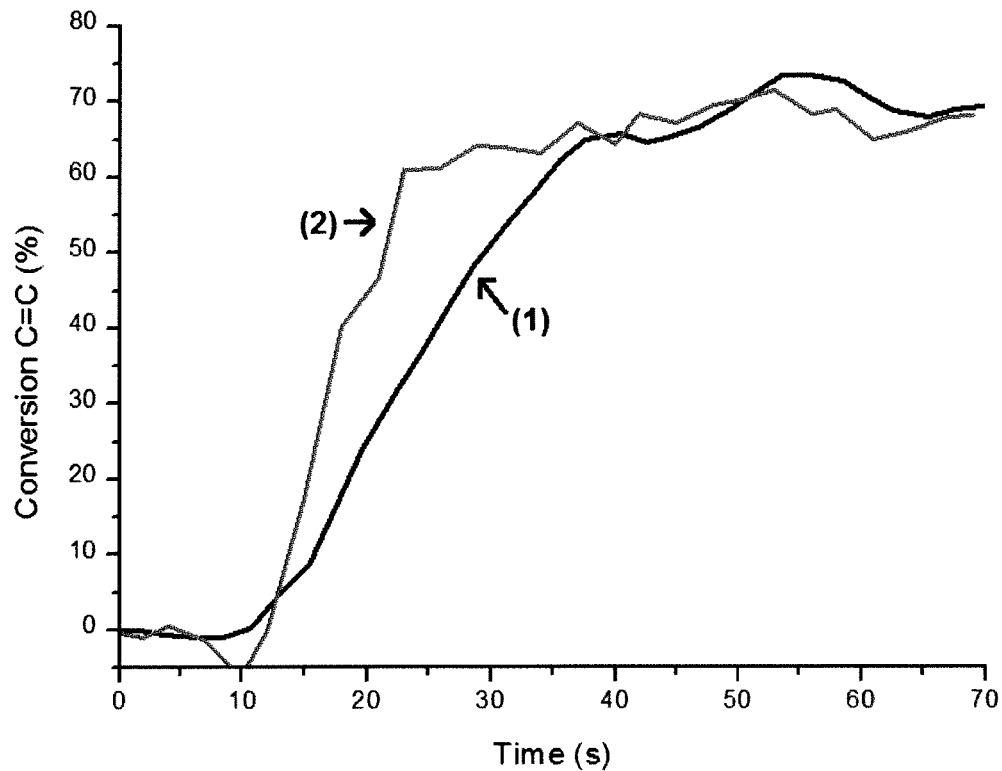
FIG. 13 shows the photopolymerization profiles of samples of 1.4 mm thickness under air upon the exposure to dental LED at 477 nm (300 mW/cm$^2$; SmartLite® Focus) for the following compositions:
  Curve (1): DKSi (1.2% w/w) in TEGDMA/BisGMA (30/70%), and
  curve (2): DKSi (1%) in BAABE/BisGMA (30/70%).
Figure 14:
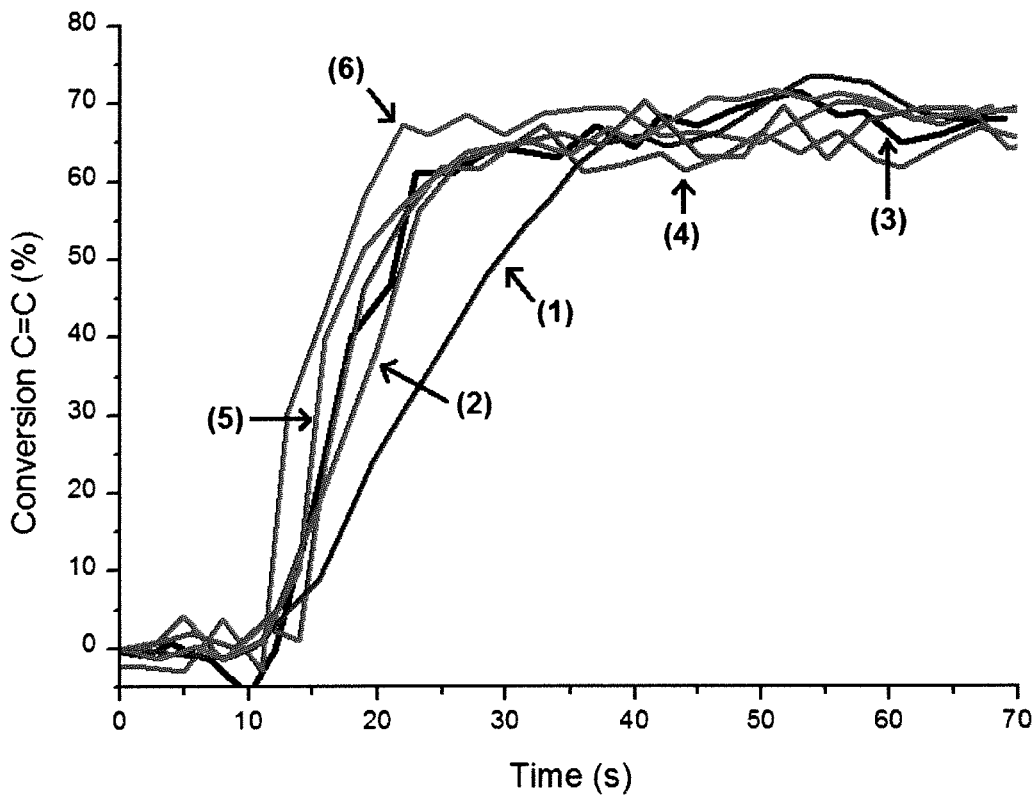
FIG. 14 shows the photopolymerization profiles of samples of 1.4 mm thickness under air upon the exposure to dental LED at 477 nm (300 mW/cm$^2$; SmartLite® Focus) for the following compositions:
  Curve (1): DKSi (1.2% w/w) in TEGDMA/BisGMA (30/70%),
  curve (2): CQ/EDB (1.2%/1.2% w/w) in TEGDMA/BisGMA (30/70%),
  curve (3): DKSi (1% w/w) in BAABE/BisGMA (30/70%),
  curve (4): DKSi (1% w/w) in BAABE/BisGMA (40/60%),
  curve (5): DKSi (1% w/w) in BAABE/BisGMA (23/77%), and
  curve (6): DKSi/di(4-tert-butylphenyl)-iodonium (DTPI) hexafluorophosphate (1%/1% w/w) in BAABE/BisGMA (40/60%).
Figure 15:
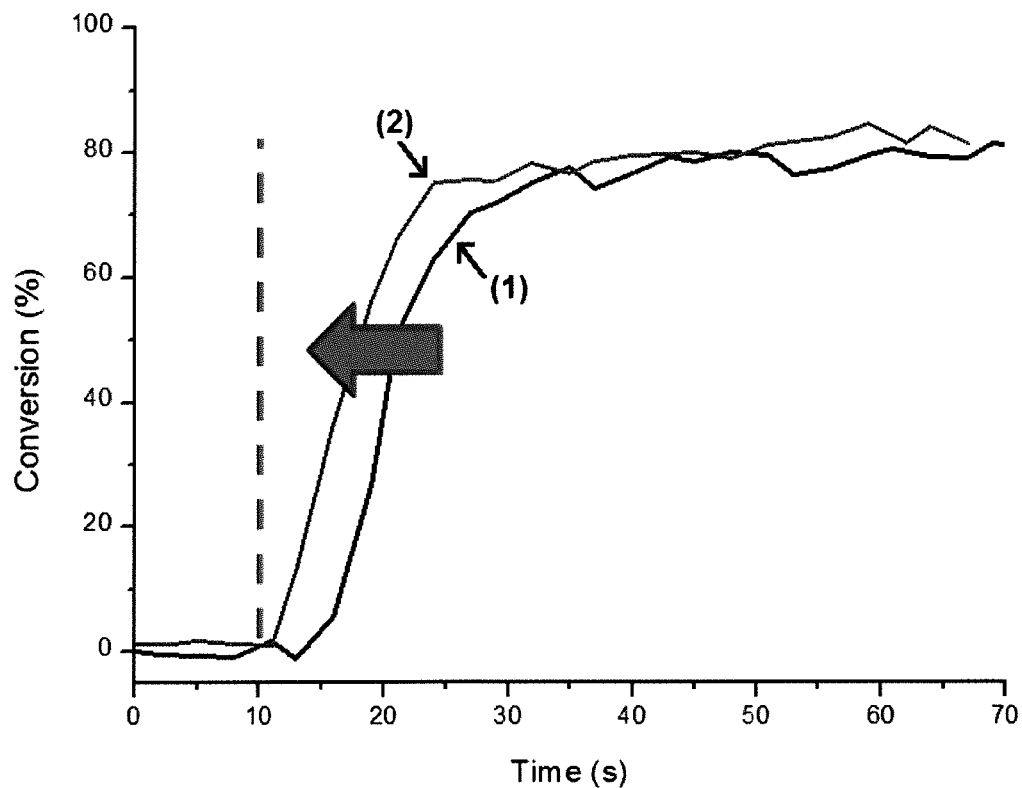
FIG. 15 shows the photopolymerization profiles of samples of 1.4 mm thickness under air upon the exposure to dental LED at 477 nm (300 mW/cm$^2$; SmartLite® Focus) for the following compositions:
  Curve (1): DKSi (1.5% w/w) in diethoxydyl methacrylate of bisphenol A (ethoxyBisGMA), and
  curve (2): DKSi (1.2% w/w) in BAABE/ethoxyBisGMA (15/85).

In the polymerization profiles depicted in FIGS. 3, 4, 7 to 9 and 12 to 16, the irradiation with the dental LED starts at t=10 s, which is for example indicated in FIGS. 3, 4 and 15 by a vertical dotted line.

Example 3: Photopolymerization Testing of an Initiator System Comprising a Glyoxylate Silyl Compound Tert-butyl (tert-butyldimethylsilyl)glyoxylate (DKSi) was tested as (a1) a sensitizer compound of formula (I) with N,N'-diallyl-1,4-bisacrylamido-(2E)-but-2-en (BAABE) as a coinitiator compound of formula (IV).

Further silyl compounds have been successfully tested as sensitizer compound in the priority application EP 15 188 969, namely benzoyldiphenylmethylsilane (BDMSi) and benzoyltrimethylsilane (BTMSi).

Figure 2:
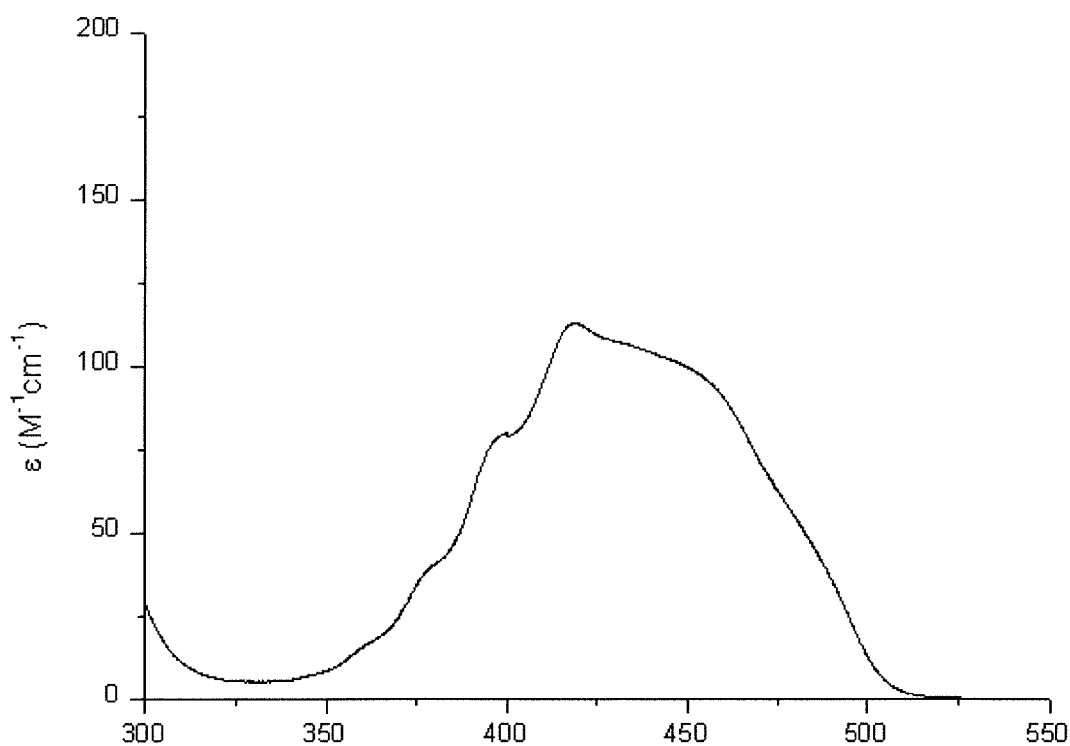
FIG. 2 shows the UV-VIS absorption spectrum of tert-butyl (tert-butyldimethylsilyl)-glyoxylate) (DKSi) in toluene.

As can be gathered from FIG. 2, DKSi has a good absorption within the 450 to 500 nm range. Therefore, DKSi is well adapted for blue light irradiation.

It was surprisingly found that with DKSi as sensitizer compound, the polymerization profile for polymerizing BAABE was improved compared with a polymerization by camphor quinone (CQ) as the sensitizer (cf. FIG. 3). FIG. 4 shows that without BAABE, with CQ, there is no or almost no polymerization for a blend of BisGMA/TEGDMA, while DKSi also provides good polymerization performance for the blend BisGMA/TEGDMA.

From the polymerization curves shown in FIGS. 3 and 4, it is understood that BAABE not only represents a polymerizable compound, but also serves as a coinitiator significantly improving the polymerization performance of the sensitizer compound, in particular of a sensitizer compound of formula (I) such as DKSi.

Figure 5:
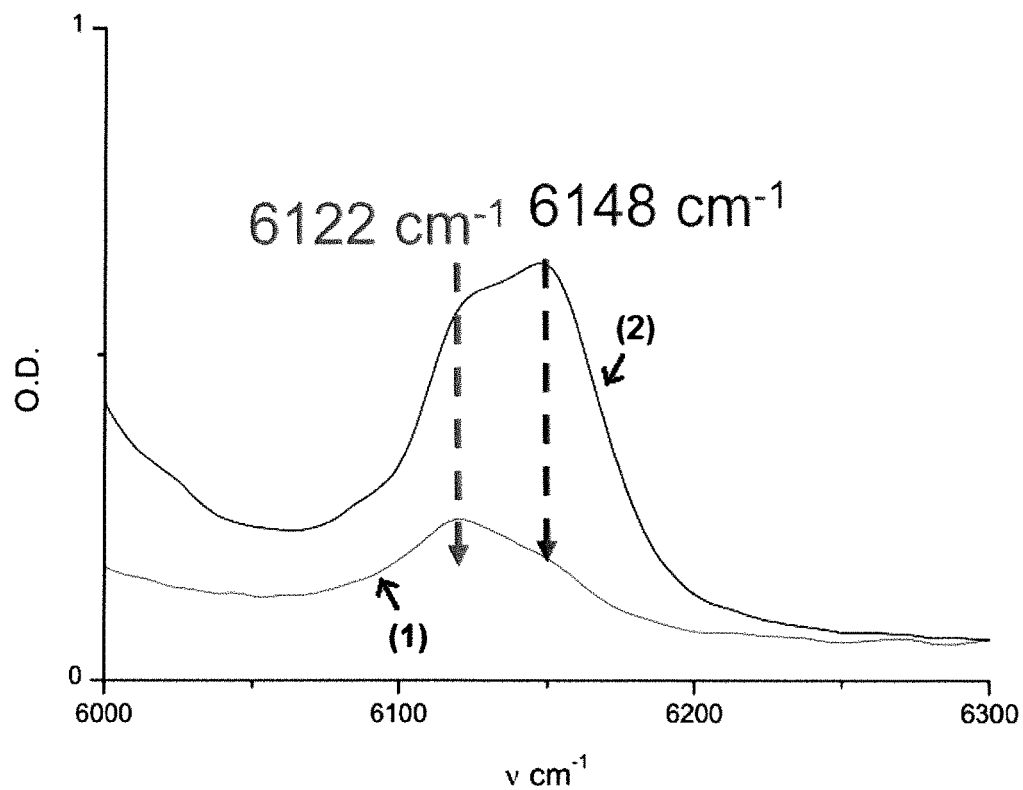
FIGS. 5 and 6 show IR-spectra before and after the polymerization of BAABE with 2% w/w CQ and of BAABE with 2% w/w DKSi polymerized in thin samples of 1.4 mm thickness under air upon the exposure to dental LED at 477 nm described for FIG. 3.
Figure 6:
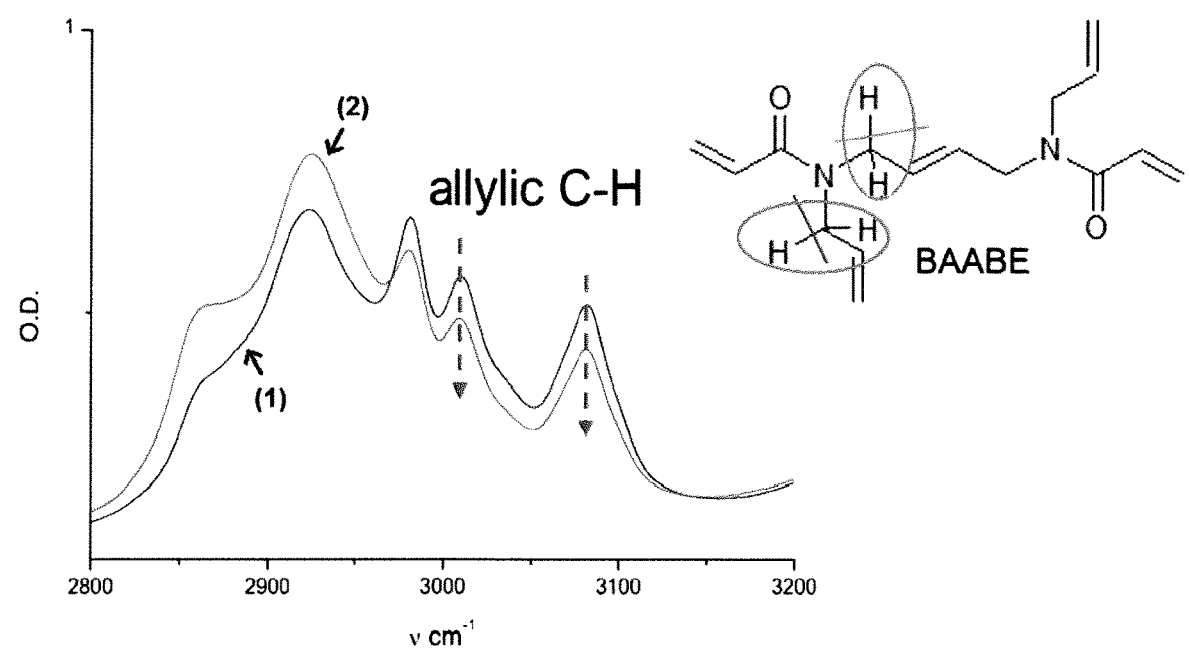

This finding is confirmed by FIGS. 5 and 6 which show that in BAABE, not only the overall C=C content is reduced, which can be seen from the peaks of about 6.122 and 6.148 cm$^{-1}$ (cf. FIG. 5). Rather, also a reduced content of allylic C—H at the peaks of about 3010 and 3080 cm$^{-1}$ was found (cf. FIG. 6). This confirms that there is a H-abstraction from the allylic C—H, which renders possible to initiate a coinitiation reaction.

For the polymerization shown in FIG. 3, it was found that in the relatively thick sample of 1.4 mm, the dissipation of the polymerization heat may not be sufficient. That is, when using BAABE alone not only as coinitiator but also as polymerizable compound having at least one polymerizable double bound, for dental application where the dental composition is used in thick samples, there may be the risk of degradation of the final polymer due to insufficient dissipation of the polymerization heat. However, this problem can be easily be circumvented, either by reducing the amount of BAABE as polymerizable compound by diluting it with other components such as fillers, solvents and/or polymerizable compounds, and/or by applying the composition as a thin film.

Figure 7:
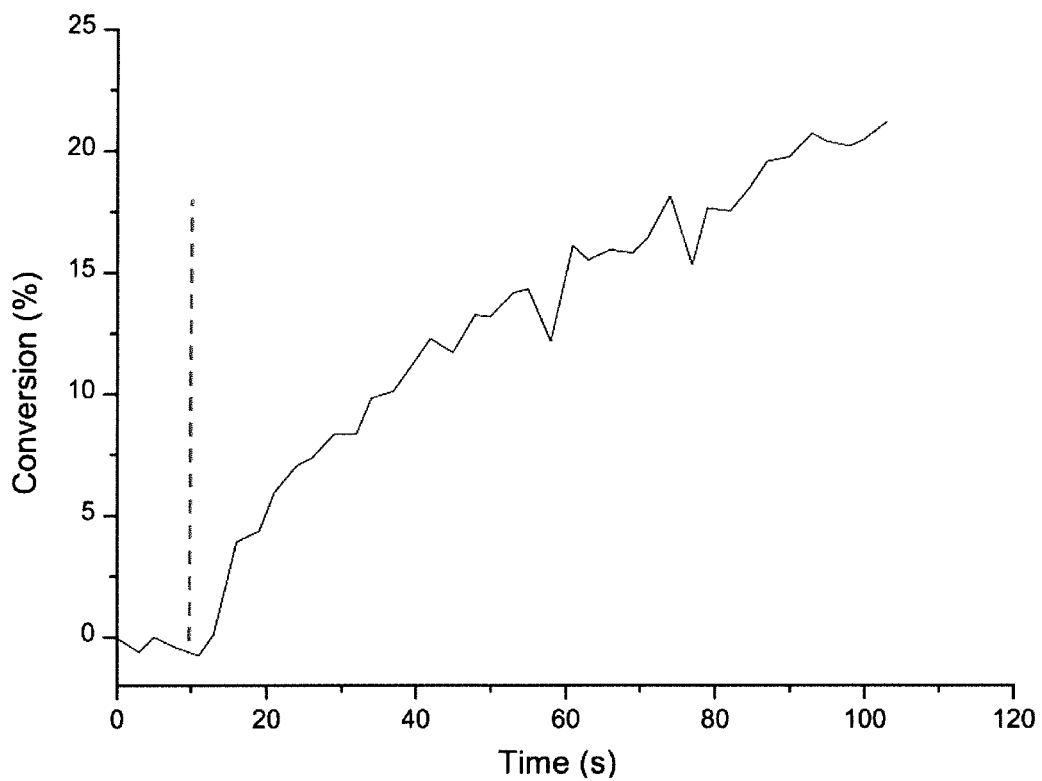
FIGS. 7 and 8 show the photopolymerization profiles of BAABE polymerized with 2% w/w DKSi under air upon the exposure to dental LED at 477 nm (SmartLite® Focus) in samples of different thickness.
Figure 8:
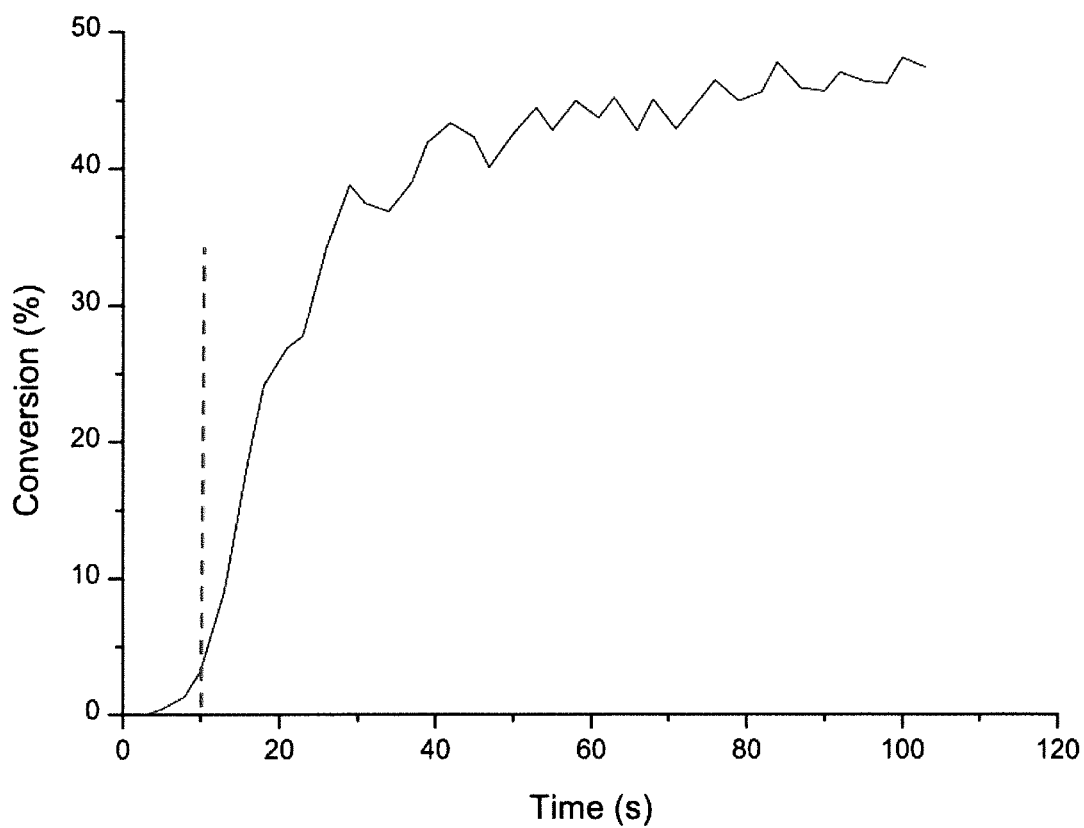

FIGS. 7 and 8 show that by reducing the thickness of the sample, the polymerization rate and conversion rate can be suitably adjusted. FIG. 7 shows that with a thin film of 20 µm, polymerization rate is significantly decreased compared with the polymerization of the thick sample of 1.4 mm shown in FIG. 3. FIG. 8 shows that with a thin film of 200 µm, polymerization rate is significantly increased compared with the thin sample of 20 µm (cf. FIG. 7). The polymerizations shown in FIGS. 7 and 8 with thinner samples show that the polymerization rate can be advantageously adjusted by suitably setting the thickness of the sample to be polymerized. In the cured samples obtained with the polymerizations shown in FIGS. 7 and 8, there is no degradation of the cured polymer, and thus there is no discoloration of the polymer.

Figure 9:
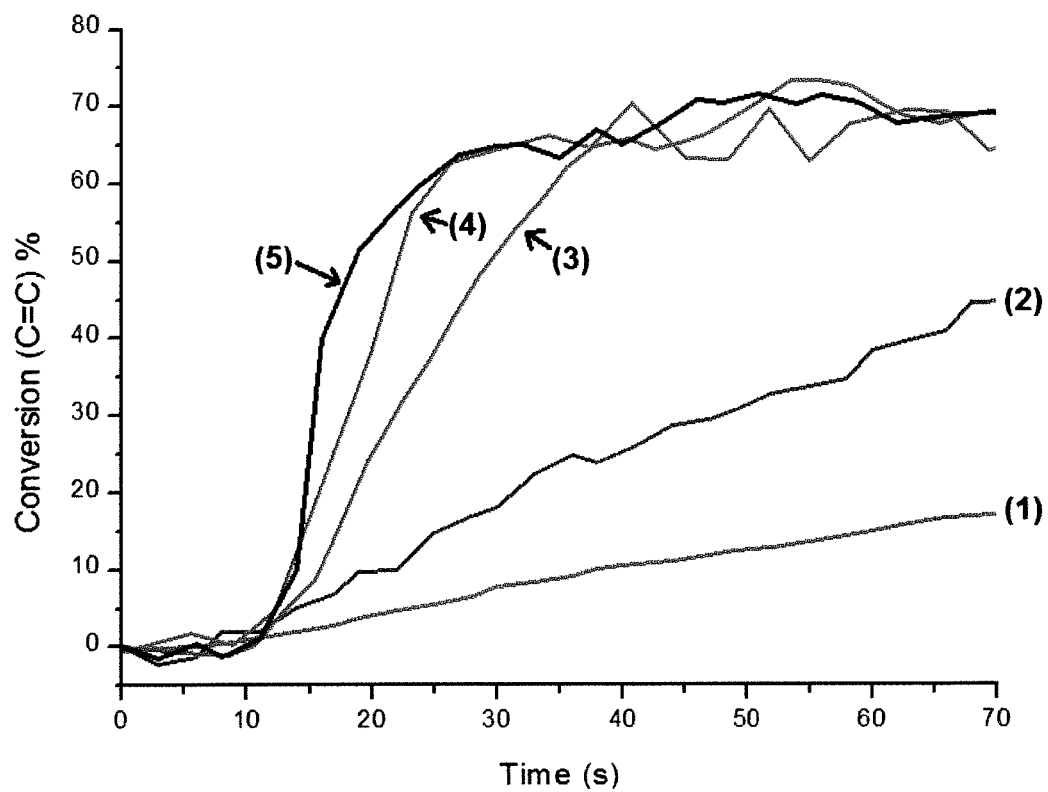
FIG. 9 shows the photopolymerization profiles of samples of 1.4 mm thickness under air upon the exposure to dental LED at 477 nm (300 mW/cm$^2$; SmartLite® Focus) for the following compositions:
  Curve (1): CQ (1% w/w) in BisGMA;
  curve (2): CQ (1% w/w) in BisGMA/BAABE (77/23%);
  curve (3): DKSi (1.2% w/w) in BisGMA/TEGDMA (70/30%)
  curve (4): CQ/ethyl N,N-dimethylaminobenzoate (EDB) (1.2/1.2% w/w) in BisGMA/TEGDMA (70/30%); and
  curve (5): DKSi (1% w/w) in BisGMA/BAABE (77/23%).

Furthermore, it was surprisingly found that an initiator system (a) consisting of (a1) the sensitizer compound of formula (I) in the form of DKSi and (a2) the coinitiator compound of formula (IV) in the form of BAABE (cf. FIG. 9, curve (5)) has an improved polymerization performance compared with an initiator system consisting of DKSi (cf. FIG. 9, curve (3)) or a conventional initiator system containing CQ and optionally a coinitiator in the form of the amine compound ethyl dimethylaminobenzoate (EDB) (cf. FIG. 9, curves (1), (2) and (4)). In particular, it is remarkable that the initiator system DKSi/BAABE provided for a polymerization performance which was significantly improved compared to the conventional system CQ/EDB in terms of both polymerization rate and conversion (cf. FIG. 9, curve (5) versus curve (4). That is, owing to the highly efficient initiator system of (a1) the sensitizer compound of formula (I) and (a2) the coinitiator compound of formula (IV), it can be dispensed with the conventional coinitiators, in particular in the form of amine compounds such as EDB. Coinitiator compounds in the form of amine compounds, specifically aromatic amine compounds, may give rise to discoloration problems, since the cured polymer suffers of yellowing/browning due to decomposition and/or side reactions of the amine compounds. Besides, from FIG. 9, it is derivable that a (a2) a coinitiator compound of formula (IV) such as BAABE not only improves polymerization performance of (a1) a sensitizer compound of formula (I), but also of a conventional sensitizer compound such as CQ, even when the conventional sensitizer compound is used in an amount of only 1% w/w (cf. FIG. 9, curves (1) and (2)).

Figure 10:
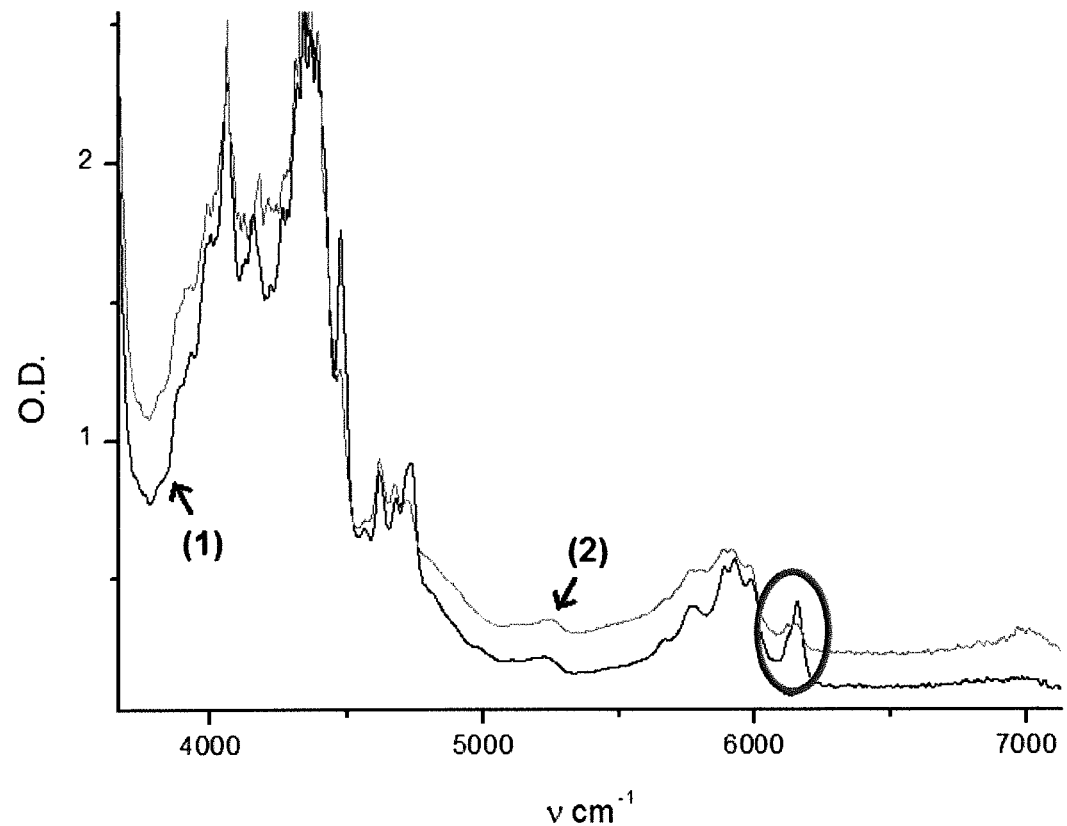
FIGS. 10 and 11 show IR-spectra before and after the polymerization of a mixture of BisGMA/BAABE (77/23%) with 1% w/w DKSi or 1% CQ described for FIG. 8.
Figure 11:
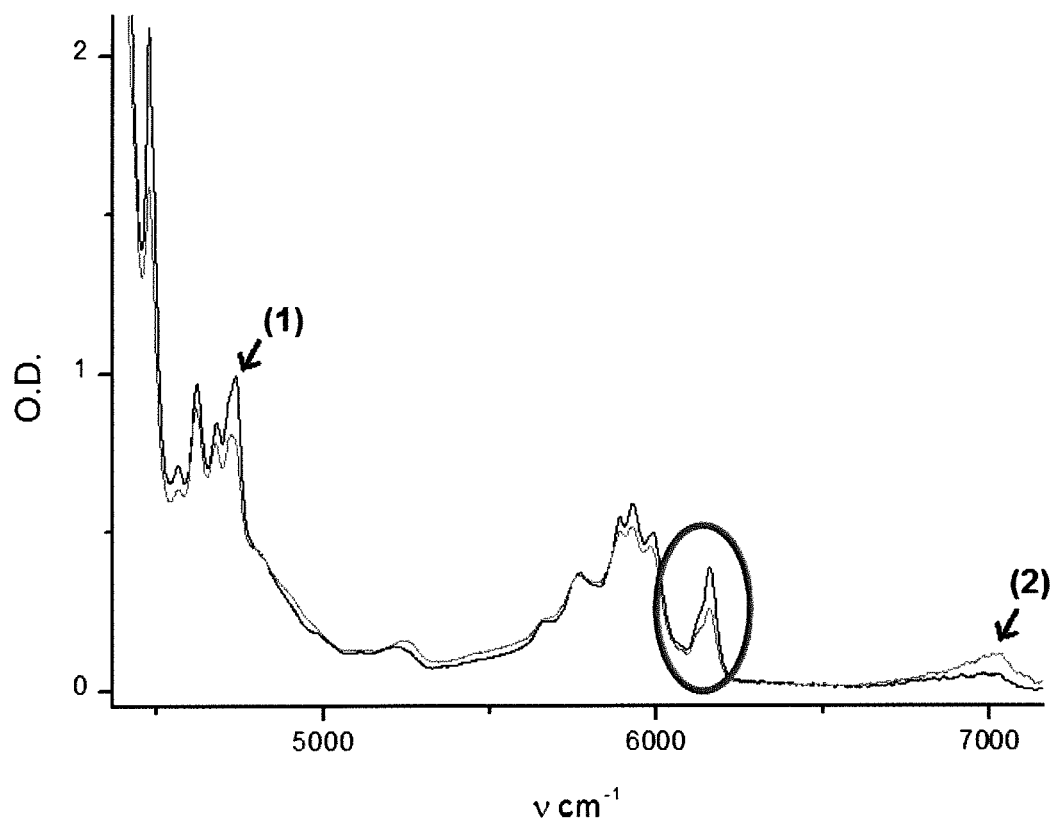

FIGS. 10 and 11 show that BAABE is a better coinitiator for DKSi compared to CQ, because together with DKSi, the overall C═C content of BAABE as polymerizable compound is significantly reduced, as can be seen from the encircled peak of the acrylamide function at about 6122 and 6148 cm$^{-1}$.

Figure 12:
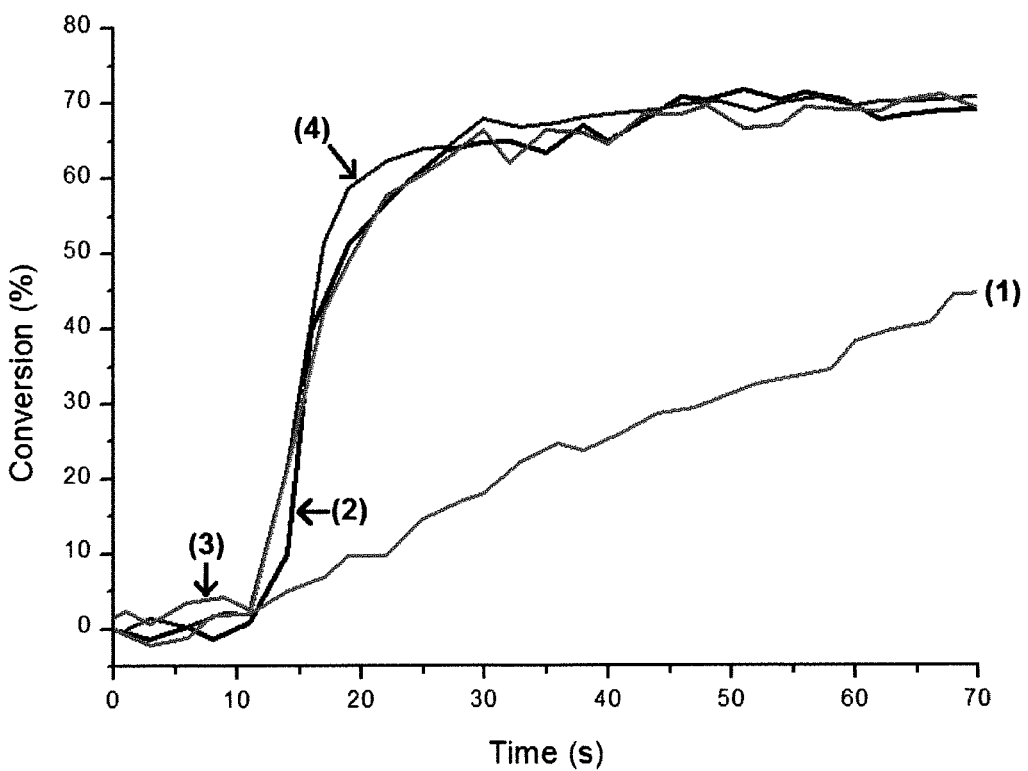
FIG. 12 shows the photopolymerization profiles of a blend of BisGMA/BAABE (77/23%) polymerized in samples of 1.4 mm thickness under air upon the exposure to dental LED at 477 nm (300 mW/cm$^2$; SmartLite® Focus) with the following different sensitizers, optionally in addition with EDB:
  Curve (1): CQ (1% w/w),
  curve (2): DKSi (1% w/w),
  curve (3): DKSi/EDB (1%/1% w/w), and
  curve (4): CQ/EDB (1%/1% w/w).

FIG. 12 shows that in the polymerization of the blend BisGMA/BAABE (77/23%), the polymerization profiles of the initiator system DKSi/BAABE and DKSi/BAABE/EDB are very similar (cf. FIG. 12, curves (3) and (4)). This is remarkable and supports that the presence of an additional amine such as EDB is not required. For CQ, the situation is different: The presence of EDB significantly improves the performance the initiator system CQ/BAABE (cf. curves (1) and (2)). In conclusion, for the initiator system CQ/BAABE, the co-initiator behavior of BAABE is less pronounced than EDB, while for DKSi, BAABE is a powerful co-initiator rendering possible to dispense with an additional coinitiator such as EDB.

FIG. 13 shows that in BisGMA, DKSi/BAABE leads to a higher polymerization rate than DKSi/TEGDMA, showing the advantages of the initiator system BAABE/DKSi. In particular, TEGMA representing a polymerizable compound which does not fall under formula (IV) cannot serve as a coinitiator, since TEGMA does not have a sufficient C—H acidity (and thus not a sufficiently low BDE) at the hydrogen adjacent to its carboxyl groups.

In FIG. 14, it can be seen that the different amine-free initiator systems DKSi/BAABE and DKSi/BAABE/DTPI lead to polymerization profiles which are similar compared to the reference system CQ/BAABE/EDB. The initiator system DKSi/BAABE/DTPI is the most efficient system (cf. FIG. 14, curve (6)). When replacing BAABE by TEGDMA, a much lower polymerization rate is found, which further supports the coinitiator behavior of compounds of formula (IV) such as BAABE (cf. FIG. 14, curves (1) and (5)). Furthermore, for different BAABE contents (23-40% w/w), excellent polymerization profiles were found for the initiator system comprising DKSi (curves (1), (3), (4) and (5)).

In FIG. 15, it is shown that the polymerization profile of ethoxyBisGMA in the presence of DKSi as sensitizer is significantly improved by the presence of BAABE. In particular, a reduction of the inhibition time, which may be ascribed to the presence oxygen, is found in presence of BAABE.

Example 4: Photopolymerization Testing of an Initiator System Comprising a Glyoxylate Germyl Compound Tert-butyl (trimethylgermyl)glyoxylate (TKGe) was tested as (a1) a sensitizer compound of formula (I) together with 4,4,6,16 (or 4,6,6,16)-tetramethyl-10, 15-dioxo-,2-[(2-methyl-1-oxo-2-propen-1-yl)oxy]ethyl ester (UDMA) as polymerizable compound.

Figure 16:
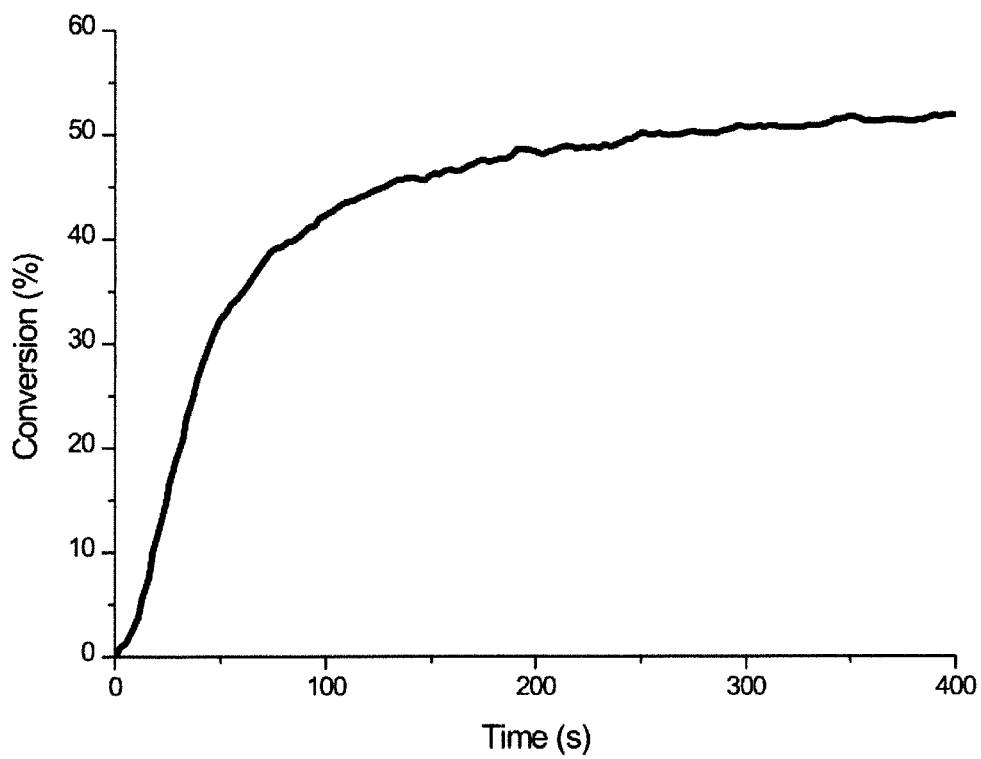
FIG. 16 shows the photopolymerization profile of UDMA polymerized with 2% w/w tert-butyl (trimethylgermyl)glyoxylate (TKGe) under air upon the exposure to dental LED at about 470 nm (300 mW/cm$^2$; SmartLite® Focus) in samples of a thickness of 1.4 mm.

FIG. 16 shows that the germylglyoxylate exhibits a good photoinitiating ability upon blue LED which is comparable to silylglyoxylates.

Example 5: Molecular Modelling

In the field of polymer chemistry, it is known that homopolymerization of allyl monomers is sluggish due to a radical degradative chain transfer. From V. P. Zubov et al., Journal of Macromolecular Science: Part A—Chemistry, 1979, vol. 13, issue 1, pages 111-131, it is known that the difference in the polymerizability of a series of allyl monomers, e. g. vinylacetic acid, allyl acetate, dimethylvinylcarbinol, diallyl ether, allyl alcohol, dimethyl-allylamine, diallylamine, and allylamine is related to the polar effects of the functional groups, whose influence determines the relative stability of the C—H bond at the α-position of the allyl group, and thus the rate of the chain transfer to the monomer (degradative chain transfer) as the result of this effect. That is, the C—H bond at the α-position of the allyl group of a monomer is decisive for the reactivity of an allyl monomer.

Figure 17:
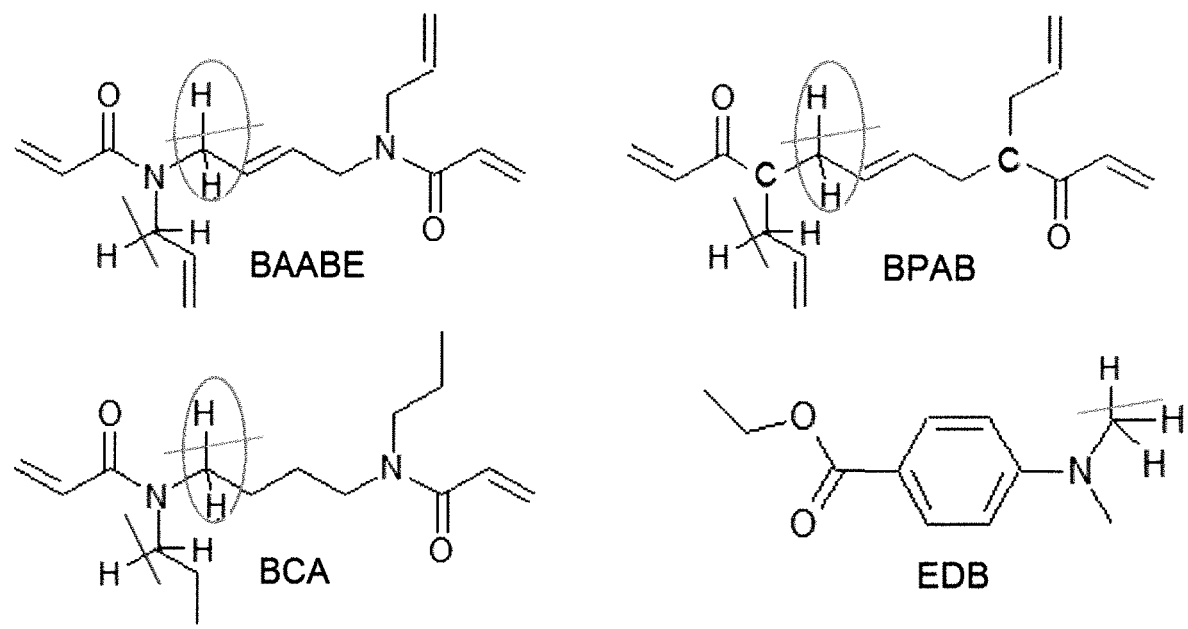
FIG. 17 shows the structural formulae of BAABE, N,N'-di-n-propyl-1,4-bisacrylamido-(2E)-but-2-en (BPAB), a BAABE analog in which the nitrogen atoms of BAABE are replaced by carbon atoms (BCA), and EDP, for which molecular modelling was carried out. In the structural formulae, it is indicated which C—H bonds may be cleaved.

Therefore, molecular modelling was carried out to calculate the bond dissociation energy (BDE) of the C—H bonds both of the C—H bond in the moiety linking the two nitrogen atoms and the C—H bond of the allyl group N—CH—CH=CH$_2$ for BAABE as a representative for a coinitiator compound of formula (IV). For comparison, BDE of the C—H bonds in BPAB, BCA and EDB was calculated. These compounds are shown with indication of the investigated C—H bonds in FIG. 17.

Molecular modelling was carried out with reference software Gaussian 09. The results are listed in Table 1 below.

TABLE 1

Results of the molecular modelling calculations

| Compound: | BDE of the C—H bond encircled in FIG. 13 [kcal/mol] | BDE of C—H bond of allyl or other group [kcal/mol] |
|---|---|---|
| BAABE | 79.88 | 81.31 |
| BPAB | 96.23 | 97.43**) |
| BCA | 86 | 88 |
| EDB | — | 96.69*) |

*)EDB has no allyl group, but only the C—H bond in α-position to its nitrogen atom
**)BPAP has no allyl group From the above calculation results, the following conclusions can be drawn:
- In BAABE, the C—H bond in the moiety linking the two nitrogen atoms has a lower BDE than the CH-bond of the allyl group, and thus the C—H bond in the linking moiety more readily donates a proton than the allyl group;
- the C—H bond BDE of BAABE is lower than for EDB, that is, BAABE is a better H-donor than EDB; and
- the comparison of BAABE and BCA shows that a heteroatom such as the nitrogen atom in BAABE is particular advantageous to significantly decrease BDE of the C—H bonds.

In conclusion, the above experimental examples support that compounds of formula (IV) such as BAABE represent highly efficient coinitiators for sensitizer compounds of formula (I) such as DKSi. Furthermore, owing to the coinitiators of formula (IV), conventional coinitiators in the form of amine compounds, which may give rise to discoloration problems, may be avoided. With the present initiator system comprising a sensitizer compound of formula (I) such as DKSi and a coinitiator compound of formula (IV) such as BAABE, excellent final conversions can be reached under air and for samples of different thicknesses upon irradiation with a blue dental LED. Moreover, for the present initiator system, the photobleaching properties were always found to be excellent.

The invention claimed is:

1. A dental composition comprising:
(a) an initiator system comprising:
(a1) a sensitizer compound of the following formula (I):

$$X-R \tag{I}$$

wherein
X is a group of the following formula (II):

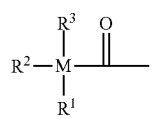

(II)

wherein
M is Si or Ge;
R$^1$ represents a substituted or unsubstituted hydrocarbyl or hydrocarbylcarbonyl group;
R$^2$ represents a substituted or unsubstituted hydrocarbyl or hydrocarbylcarbonyl group;
R$^3$ represents a substituted or unsubstituted hydrocarbyl group; and
R (i) has the same meaning as X, whereby the sensitizer compound of formula (I) may be symmetrical or unsymmetrical; or
(ii) is a group of the following formula (III):

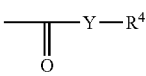

(III)

wherein
Y represents a single bond, an oxygen atom or a group NR', wherein R' represents a substituted or unsubstituted hydrocarbyl group;
R$^4$ represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group; or
(iii) when M is Si, R may be a substituted or unsubstituted hydrocarbyl group, and
(a2) a coinitiator compound of the following formula (IV):

$$X'\text{-L-}X'' \tag{IV}$$

wherein
X' represents a group of the following formula (V) or (VI):

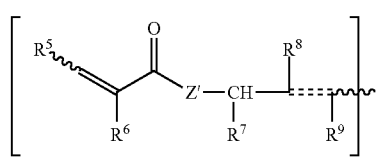

(V)

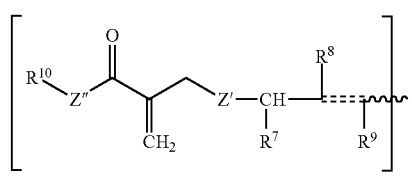

(VI)

wherein
the dotted lines represent
a double bond or a triple bond, whereby in case a triple bond is present, R$^8$ and R$^9$ are absent;

the jagged line(s) indicate(s) that formula (V) and (VI) include any (E) or (Z) isomer, Z' and Z", which may be the same or different, independently represent an oxygen atom, a sulfur atom or >N—R°, wherein R° is a hydrogen atom, a straight-chain, branched or cyclic alkyl or alkenyl group which group may be substituted by an alkoxy or acidic group, or a group of the following formula (VII):

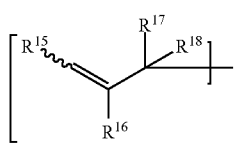
(VII)

wherein the jagged line indicates that formula (VII) includes any (E) or (Z) isomer, $R^{15}$ and $R^{16}$, which may be the same or different, independently represent a hydrogen atom or a straight-chain, branched or cyclic alkyl or alkenyl group, which group may be substituted by an alkoxy group or acidic group;

$R^{17}$ and $R^{18}$, which may be the same or different, independently represent a hydrogen atom or a straight-chain, branched or cyclic alkyl or alkenyl group, which group may be substituted by an alkoxy or acidic group, or $R^{17}$ and $R^{18}$ represent together an oxygen atom forming a carbonyl group together with the adjacent carbon atom;

$R^5$ and $R^6$, which may be the same or different, independently represent a hydrogen atom or a straight-chain, branched or cyclic alkyl or alkenyl group, which group may be substituted by at least one moiety selected from the group consisting of a hydroxyl group, an alkoxy group and an acidic group;

$R^7$ represents a hydrogen atom or a straight-chain, branched or cyclic alkyl or alkenyl group, which group may be substituted by an alkoxy or acidic group;

$R^8$ and $R^9$, which may be the same or different, independently represent a hydrogen atom, a straight-chain, branched or cyclic alkyl or alkenyl group, which group may be substituted by an alkoxy or acidic group;

$R^{10}$ represents a hydrogen atom or a straight-chain, branched or cyclic alkyl or alkenyl group, which group may be substituted by an alkoxy group;

X" represents a moiety selected from the group consisting of a hydroxyl group, a thiol group, an alkoxy group and an acidic group, or a moiety of the following formula (VIII) or (IX):

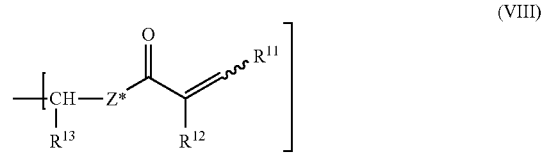
(VIII)

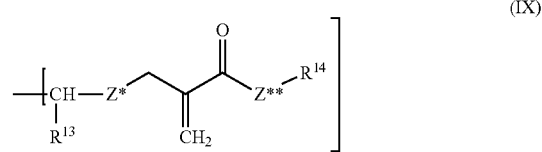
(IX)

wherein the jagged line indicates that formula (VIII) includes any (E) or (Z) isomer, Z* and Z**, which may be the same or different, independently represent an oxygen atom, a sulfur atom or >N—R*, wherein R* is a hydrogen atom, a straight-chain, branched or cyclic alkyl or alkenyl group which group may be substituted by an alkoxy or acidic group, or R* independently is a group of the formula (VII) as defined for R°;

$R^{11}$ and $R^{12}$ which may be the same or different, independently represent a hydrogen atom, a straight-chain, branched or cyclic alkyl or alkenyl group, which group may be substituted by at least one moiety selected from the group consisting of a hydroxyl group, a thiol group, an alkoxy group and an acidic group;

$R^{13}$ represents a hydrogen atom or a straight-chain, branched or cyclic alkyl or alkenyl group, which group may be substituted by an alkoxy or acidic group;

$R^{14}$ represents a hydrogen atom or a straight-chain, branched or cyclic alkyl or alkenyl group, which group may be substituted by an alkoxy group;

or alternatively, any two residues of $R^5$, $R^6$, $R^7$, $R^8$, $R^9$, $R^{10}$, $R°$, $R^{11}$, $R^{12}$, $R^{13}$, $R^{14}$, $R^*$, and if present, $R^{15}$, $R^{16}$, $R^{17}$ and $R^{18}$ may represent together an alkylene or alkenylene group, which may be substituted by an alkoxy group, an acidic group or a —NR▲R▼ group wherein R▲ and R▼ independently from each other represent a hydrogen atom or an alkyl group; or any two residues of $R^5$, $R^6$, $R^7$, $R^8$, $R^9$, $R^{10}$, $R°$, $R^{11}$, $R^{12}$, $R^{13}$, $R^{14}$, $R^*$, and if present, $R^{15}$, $R^{16}$, $R^{17}$ and $R^{18}$, which are not geminal or vicinal groups, may represent together a single bond, wherein said single bond or said optionally substituted alkylene or alkenylene group form together with the bridging atoms to which the residues are linked a 3- to 8-membered saturated or unsaturated ring, wherein the polymerizable compound of formula (II) may comprise one or more of said 3- to 8-membered saturated or unsaturated ring(s); and L which may be present or absent, represents, when present, a divalent linker group, and when absent X' and X" are bonded directly by a single bond.

2. The dental composition according to claim 1, wherein in the coinitiator compound of formula (IV), L is a group of the following formula (X)

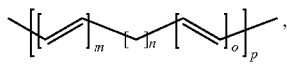 (X)

wherein
m, n and o, which may be the same or different are integers of from 0 to 3; and p is 0, 1 or 2.

3. The dental composition according to claim 1, wherein the sensitizer compound of formula (I) is tert-butyl (tert-butyldimethylsilyl)glyoxylate (DKSi).

4. The dental composition according to claim 1, wherein the coinitiator compound of formula (IV) has an allyl group and/or a C—H bond having a C—H bond dissociation energy of less than 95 Kcal/mol.

5. The dental composition according to claim 1, which does not contain an aromatic amine compound.

6. The dental composition according to claim 1, which further comprises
(b) one or more polymerizable compounds having at least one polymerizable double bond.

7. The dental composition according to claim 1, wherein the initiator system comprises component (a1) and (a2) in a molar ratio ((a1):(a2) of 1:(0.0 to 3.0)).

8. The dental composition according to claim 1, which further comprises a solvent and/or a particulate filler.

9. The dental composition according to claim 1, which further comprises one or more components selected from
(a3) an iodonium salt, a sulfonium salt or a phosphonium salt.

10. The dental composition according to claim 9, wherein the iodonium salt is selected from diphenyliodonium hexafluorophosphate or (4-methylphenyl)[4-(2-methylpropyl)phenyl]iodonium hexafluorophosphate.

11. The dental composition according to claim 1, which further comprises
(a4) an aromatic tertiary phosphine compound of the following formula (XI):

$$Z'''—R^{19} \qquad (XI)$$

wherein
$Z'''$ is a group of the following formula (XII)

$$R^{20}(Ar)P— \qquad (XII)$$

wherein
$R^{20}$ represents a substituted or unsubstituted hydrocarbyl group;
Ar represents a substituted or unsubstituted aryl or heteroaryl group;
$R^{19}$ is a substituted or unsubstituted hydrocarbyl group or a group $L'Z^{iv}$, wherein
L' is a substituted or unsubstituted divalent hydrocarbyl group which may contain a linkage selected from an ether linkage, a thioether linkage, an ester linkage, an amide linkage, and a urethane linkage and
$Z^{iv}$ has the same meaning as $Z'''$, whereby $Z'''$ and $Z^{iv}$ may be the same or different;
wherein the group $R^{19}$ and Ar may be substituted by one or more groups selected from a hydroxyl group, an oxo group, a —$NR^{21}R^{22}$ group (wherein $R^{21}$ and $R^{22}$, which may be the same or different, are selected from a hydrogen atom and $C_{1-6}$ alkyl groups), a carboxyl group, and a group having a polymerizable double bond, and
$R^{19}$ and L' may be substituted by one or more groups selected from a hydroxyl group, an oxo group, a —$NR^{21}R^{22}$ group (wherein $R^{21}$ and $R^{22}$, which may be the same or different, are selected from a hydrogen atom and $C_{1-6}$ alkyl groups), a carboxyl group, and a group having a polymerizable double bond.

12. The dental composition according to claim 1, wherein the dental composition is a dental restorative or dental prosthetic composition.

13. The dental composition according to claim 1, wherein the dental composition is a dental adhesive composition, a dental composite composition, a resin modified dental cement, a pit and fissure sealer, a desensitizer or a varnish.

14. Initiator system consisting essentially of
(a1) a sensitizer compound of the formula (I) as defined by claim 1, and
(a2) a coinitiator wherein a C—H bond dissociation energy is less than 95 Kcal/mol.

* * * * *